(12) United States Patent
Esfandyarpour et al.

(10) Patent No.: US 10,472,674 B2
(45) Date of Patent: *Nov. 12, 2019

(54) SYSTEMS AND METHODS FOR AUTOMATED REUSABLE PARALLEL BIOLOGICAL REACTIONS

(71) Applicant: GenapSys, Inc., Redwood City, CA (US)

(72) Inventors: Hesaam Esfandyarpour, Redwood City, CA (US); Mark Oldham, Emerald Hills, CA (US)

(73) Assignee: GENAPSYS, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/360,369

(22) Filed: Nov. 23, 2016

(65) Prior Publication Data

US 2017/0073750 A1   Mar. 16, 2017

Related U.S. Application Data

(63) Continuation of application No. 14/835,070, filed on Aug. 28, 2015, now Pat. No. 9,533,305, which is a
(Continued)

(51) Int. Cl.
| | |
|---|---|
| *C12Q 1/6874* | (2018.01) |
| *C12Q 1/6869* | (2018.01) |
| *G01N 27/414* | (2006.01) |
| *G01N 33/543* | (2006.01) |
| *C40B 60/10* | (2006.01) |
| *C12Q 1/6853* | (2018.01) |
| *C12Q 1/6848* | (2018.01) |
| *G01N 1/40* | (2006.01) |
| *B01L 3/00* | (2006.01) |
| *B01L 7/00* | (2006.01) |
| *B03C 1/28* | (2006.01) |

(Continued)

(52) U.S. Cl.
CPC ...... *C12Q 1/6874* (2013.01); *B01L 3/502738* (2013.01); *B01L 3/502761* (2013.01); *B01L 7/52* (2013.01); *B03C 1/286* (2013.01); *B03C 1/288* (2013.01); *B03C 1/30* (2013.01); *B03C 5/005* (2013.01); *B03C 5/022* (2013.01); *B03C 5/026* (2013.01); *C12Q 1/6848* (2013.01); *C12Q 1/6853* (2013.01); *C12Q 1/6869* (2013.01); *G01N 1/40* (2013.01); *G01N 27/4145* (2013.01); *G01N 27/4146* (2013.01); *G01N 33/5438* (2013.01); *B01L 2200/0652* (2013.01); *B01L 2200/0668* (2013.01); *B01L 2200/0689* (2013.01); *B01L 2200/10* (2013.01); *B01L 2300/0645* (2013.01); *B01L 2300/089* (2013.01); *B01L 2300/0816* (2013.01); *B01L 2300/0887* (2013.01); *B01L 2300/12* (2013.01); *B01L 2300/123* (2013.01); *B01L 2400/043* (2013.01); *B01L 2400/0415* (2013.01); *B01L 2400/0418* (2013.01); *B01L 2400/0421* (2013.01); *B01L 2400/0424* (2013.01); *B01L 2400/0427* (2013.01); *B01L 2400/0478* (2013.01); *B01L 2400/0655* (2013.01); *B03C 2201/26* (2013.01); *C40B 60/10* (2013.01); *G01N 2001/4038* (2013.01)

(58) Field of Classification Search
None
See application file for complete search history.

(56) References Cited

U.S. PATENT DOCUMENTS

| | | |
|---|---|---|
| 2,014,761 A | 9/1935 | Faust |
| 4,072,576 A | 2/1978 | Arwin et al. |

(Continued)

FOREIGN PATENT DOCUMENTS

| | | |
|---|---|---|
| CN | 1337580 A | 2/2002 |
| CN | 101120098 A | 2/2008 |

(Continued)

OTHER PUBLICATIONS

Lee et al., "Ion-Sensitive Field-Effect Transistor for Biological Sensing," Sensors 2009, 9:7111-7131. (Year: 2009).*
International Search Report and Written Opinion dated Nov. 16, 2017 for International PCT Patent Application No. PCT/US2017/43159.
Co-pending U.S. Appl. No. 15/655,616, filed Jul. 20, 2017.
Notice of Allowance dated Jul. 6, 2017 for U.S. Appl. No. 14/653,230.
Notice of Allowance dated Jul. 10, 2017 for U.S. Appl. No. 14/688,764.
Notice of Allowance dated Jul. 20, 2017 for U.S. Appl. No. 14/688,764.

(Continued)

*Primary Examiner* — Kaijiang Zhang
(74) *Attorney, Agent, or Firm* — Wilson Sonsini Goodrich & Rosati

(57) ABSTRACT

A method comprises magnetically holding a bead carrying biological material (e.g., nucleic acid, which may be in the form of DNA fragments or amplified DNA) in a specific location of a substrate, and applying an electric field local to the bead to isolate the biological material or products or byproducts of reactions of the biological material. For example, the bead is isolated from other beads having associated biological material. The electric field in various embodiments concentrates reagents for an amplification or sequencing reaction, and/or concentrates and isolates detectable reaction by-products. For example, by isolating nucleic acids around individual beads, the electric field can allow for clonal amplification, as an alternative to emulsion PCR. In other embodiments, the electric field isolates a nanosensor proximate to the bead, to facilitate detection of at least one of local pH change, local conductivity change, local charge concentration change and local heat. The beads may be trapped in the form of an array of localized magnetic field regions.

21 Claims, 34 Drawing Sheets

Related U.S. Application Data continuation of application No. 14/596,111, filed on Jan. 13, 2015, now Pat. No. 9,150,915, which is a continuation of application No. 13/632,513, filed on Oct. 1, 2012, now Pat. No. 8,969,002, which is a continuation of application No. 13/397,581, filed on Feb. 15, 2012, now abandoned, which is a continuation-in-part of application No. PCT/US2011/054769, filed on Oct. 4, 2011.

(60) Provisional application No. 61/389,484, filed on Oct. 4, 2010, provisional application No. 61/389,490, filed on Oct. 4, 2010, provisional application No. 61/443,167, filed on Feb. 15, 2011, provisional application No. 61/491,081, filed on May 27, 2011.

(51) Int. Cl.
  *B03C 5/00* (2006.01)
  *B03C 5/02* (2006.01)
  *B03C 1/30* (2006.01)

(56) References Cited

U.S. PATENT DOCUMENTS

| | | |
|---|---|---|
| 5,344,545 A | 9/1994 | Tsukada et al. |
| 5,407,799 A | 4/1995 | Studier et al. |
| 5,466,348 A | 11/1995 | Holm-Kennedy |
| 5,602,042 A | 2/1997 | Farber |
| 5,612,181 A | 3/1997 | Fourmentin-Guilbert |
| 5,795,782 A | 8/1998 | Church et al. |
| 5,834,197 A | 11/1998 | Parton |
| 6,046,097 A | 4/2000 | Hsieh et al. |
| 6,087,095 A | 7/2000 | Rosenthal et al. |
| 6,210,891 B1 | 4/2001 | Nyren et al. |
| 6,327,410 B1 | 12/2001 | Walt et al. |
| 6,632,655 B1 | 10/2003 | Mehta et al. |
| 6,833,246 B2 | 12/2004 | Balasubramanian |
| 6,870,235 B2 | 3/2005 | Abstreiter et al. |
| 6,953,958 B2 | 10/2005 | Baxter et al. |
| 7,081,192 B1 | 7/2006 | Wang et al. |
| 7,095,010 B2 | 8/2006 | Scherer et al. |
| 7,223,540 B2 | 5/2007 | Pourmand et al. |
| 7,238,536 B1 | 7/2007 | Schlenoff |
| 7,242,241 B2 | 7/2007 | Toumazou et al. |
| 7,270,981 B2 | 9/2007 | Armes et al. |
| 7,282,370 B2 | 10/2007 | Bridgham et al. |
| 7,291,496 B2 | 11/2007 | Holm-Kennedy |
| 7,312,085 B2 | 12/2007 | Chou et al. |
| 7,317,216 B2 | 1/2008 | Holm-Kennedy |
| 7,323,305 B2 | 1/2008 | Leamon et al. |
| 7,361,466 B2 | 4/2008 | Korlach et al. |
| 7,399,590 B2 | 7/2008 | Piepenburg et al. |
| 7,435,561 B2 | 10/2008 | Piepenburg et al. |
| 7,485,428 B2 | 2/2009 | Armes et al. |
| 7,615,382 B2 | 11/2009 | Wang et al. |
| 7,645,596 B2 | 1/2010 | Williams et al. |
| 7,649,358 B2 | 1/2010 | Toumazou et al. |
| 7,666,598 B2 | 2/2010 | Piepenburg et al. |
| 7,682,837 B2 | 3/2010 | Jain et al. |
| 7,686,929 B2 | 3/2010 | Toumazou et al. |
| 7,692,219 B1 | 4/2010 | Holm-Kennedy |
| 7,695,907 B2 | 4/2010 | Miyahara et al. |
| 7,763,427 B2 | 7/2010 | Piepenburg et al. |
| 7,824,890 B2 | 11/2010 | Hoser et al. |
| 7,835,871 B2 | 11/2010 | Kain et al. |
| 7,875,440 B2 | 1/2011 | Williams et al. |
| 7,888,013 B2 | 2/2011 | Miyahara et al. |
| 7,932,034 B2 | 4/2011 | Esfandyarpour et al. |
| 7,948,015 B2 | 5/2011 | Rothberg et al. |
| 8,023,113 B2 | 9/2011 | El Gamal et al. |
| 8,030,000 B2 | 10/2011 | Piepenburg et al. |
| 8,039,817 B2 | 10/2011 | Feng et al. |
| 8,062,848 B2 | 11/2011 | Goldstein et al. |
| 8,062,850 B2 | 11/2011 | Piepenburg et al. |
| 8,071,308 B2 | 12/2011 | Piepenburg et al. |
| 8,114,591 B2 | 2/2012 | Toumazou et al. |
| 8,128,796 B2 | 3/2012 | Ishige et al. |
| 8,129,118 B2 | 3/2012 | Weindel et al. |
| 8,137,569 B2 | 3/2012 | Harnack et al. |
| 8,152,991 B2 | 4/2012 | Briman et al. |
| 8,154,093 B2 | 4/2012 | Bradley et al. |
| 8,173,080 B2 | 5/2012 | Lebl et al. |
| 8,173,401 B2 | 5/2012 | Chang et al. |
| 8,179,296 B2 | 5/2012 | Kelly et al. |
| 8,257,925 B2 | 9/2012 | Brown et al. |
| 8,274,040 B2 | 9/2012 | Zhong et al. |
| 8,301,394 B2 | 10/2012 | Chen et al. |
| 8,315,817 B2 | 11/2012 | Kain et al. |
| 8,392,126 B2 | 3/2013 | Mann |
| 8,426,134 B2 | 4/2013 | Piepenburg et al. |
| 8,460,875 B2 | 6/2013 | Armes et al. |
| 8,486,625 B2 | 7/2013 | Gunderson et al. |
| 8,518,670 B2 | 8/2013 | Goldstein et al. |
| 8,574,846 B2 | 11/2013 | Piepenburg et al. |
| 8,580,507 B2 | 11/2013 | Piepenburg et al. |
| 8,585,973 B2 | 11/2013 | Esfandyarpour |
| 8,637,253 B2 | 1/2014 | Piepenburg et al. |
| 8,649,011 B2 | 2/2014 | McCaffrey et al. |
| 8,673,560 B2 | 3/2014 | Leamon et al. |
| 8,778,848 B2 | 7/2014 | Lin et al. |
| 8,778,849 B2 | 7/2014 | Bowen et al. |
| 8,865,077 B2 | 10/2014 | Chiou et al. |
| 8,865,078 B2 | 10/2014 | Chiou et al. |
| 8,914,241 B2 | 12/2014 | Kain et al. |
| 8,969,002 B2 | 3/2015 | Esfandyarpour et al. |
| 9,045,796 B2 | 6/2015 | Gunderson et al. |
| 9,063,117 B2 | 6/2015 | Gourley |
| 9,150,915 B2 | 10/2015 | Esfandyarpour et al. |
| 9,184,099 B2 | 11/2015 | Baghbani-Parizi et al. |
| 9,187,783 B2 | 11/2015 | Esfandyarpour et al. |
| 9,188,594 B2 | 11/2015 | Fahmy et al. |
| 9,274,077 B2 | 3/2016 | Esfandyarpour et al. |
| 9,399,217 B2 | 7/2016 | Esfandyarpour et al. |
| 9,434,983 B2 | 9/2016 | Esfandyarpour |
| 9,533,305 B2 | 1/2017 | Esfandyarpour et al. |
| 9,689,835 B2 | 6/2017 | Liu et al. |
| 9,809,852 B2 | 11/2017 | Esfandyarpour et al. |
| 9,822,401 B2 | 11/2017 | Oberstrass et al. |
| 9,926,596 B2 | 3/2018 | Esfandyarpour et al. |
| 9,945,807 B2 | 4/2018 | Baghbani-Parizi et al. |
| 9,990,381 B2 | 6/2018 | Eltoukhy et al. |
| 10,059,982 B2 | 8/2018 | Esfandyarpour et al. |
| 10,093,975 B2 | 10/2018 | Esfandyarpour et al. |
| 10,100,356 B2 | 10/2018 | Esfandyarpour et al. |
| 10,125,393 B2 | 11/2018 | Esfandyarpour et al. |
| 10,260,095 B2 | 4/2019 | Esfandyarpour et al. |
| 10,266,892 B2 | 4/2019 | Esfandyarpour et al. |
| 2002/0132245 A1 | 9/2002 | Boles et al. |
| 2002/0148739 A2 | 10/2002 | Liamos et al. |
| 2003/0078314 A1 | 4/2003 | Johnson et al. |
| 2003/0209432 A1 | 11/2003 | Choong et al. |
| 2004/0014201 A1 | 1/2004 | Kim et al. |
| 2004/0023253 A1 | 2/2004 | Kunwar et al. |
| 2004/0033492 A1 | 2/2004 | Chen |
| 2004/0136866 A1 | 7/2004 | Pontis et al. |
| 2004/0197793 A1 | 10/2004 | Hassibi et al. |
| 2005/0009022 A1 | 1/2005 | Weiner et al. |
| 2005/0019784 A1 | 1/2005 | Su et al. |
| 2005/0032076 A1 | 2/2005 | Williams et al. |
| 2005/0084980 A1 | 4/2005 | Koo et al. |
| 2005/0098434 A1 | 5/2005 | Gundel et al. |
| 2005/0123937 A1 | 6/2005 | Thorp et al. |
| 2005/0129526 A1 | 6/2005 | Dukhin et al. |
| 2005/0200648 A1 | 9/2005 | Doak et al. |
| 2005/0218464 A1 | 10/2005 | Holm-Kennedy |
| 2006/0008824 A1 | 1/2006 | Ronaghi et al. |
| 2006/0105373 A1 | 5/2006 | Pourmand et al. |
| 2006/0147955 A1 | 7/2006 | Allawi et al. |
| 2006/0170931 A1 | 8/2006 | Guo et al. |
| 2006/0199193 A1 | 9/2006 | Koo et al. |
| 2006/0222569 A1 | 10/2006 | Barten et al. |
| 2007/0132043 A1 | 6/2007 | Bradley et al. |
| 2007/0184463 A1 | 8/2007 | Molho et al. |

(56) References Cited

U.S. PATENT DOCUMENTS

| | | |
|---|---|---|
| 2007/0275375 A1 | 11/2007 | Van Eijk et al. |
| 2008/0009420 A1 | 1/2008 | Schroth et al. |
| 2008/0032294 A1 | 2/2008 | Kawarada et al. |
| 2008/0032295 A1 | 2/2008 | Toumazou et al. |
| 2008/0161200 A1 | 7/2008 | Yu et al. |
| 2008/0166727 A1 | 7/2008 | Esfandyarpour et al. |
| 2008/0171325 A1 | 7/2008 | Brown et al. |
| 2008/0176817 A1 | 7/2008 | Zhou et al. |
| 2008/0187915 A1 | 8/2008 | Polonsky et al. |
| 2008/0241841 A1 | 10/2008 | Murakawa et al. |
| 2008/0286762 A1* | 11/2008 | Miyahara et al. ... C12Q 1/6825 435/29 |
| 2008/0302732 A1 | 12/2008 | Soh et al. |
| 2008/0318243 A1 | 12/2008 | Haga et al. |
| 2009/0000957 A1 | 1/2009 | Dubin et al. |
| 2009/0005259 A1 | 1/2009 | Drmanac |
| 2009/0026082 A1 | 1/2009 | Rothberg et al. |
| 2009/0029385 A1 | 1/2009 | Christians et al. |
| 2009/0032401 A1 | 2/2009 | Ronaghi et al. |
| 2009/0048124 A1 | 2/2009 | Leamon et al. |
| 2009/0127589 A1 | 5/2009 | Rothberg et al. |
| 2009/0166221 A1* | 7/2009 | Ishige et al. ......... C12Q 1/6825 205/777.5 |
| 2009/0170716 A1 | 7/2009 | Su et al. |
| 2009/0170724 A1 | 7/2009 | Balasubramanian et al. |
| 2009/0181385 A1 | 7/2009 | McKernan et al. |
| 2009/0191594 A1 | 7/2009 | Ohashi |
| 2010/0000881 A1 | 1/2010 | Franzen et al. |
| 2010/0035252 A1 | 2/2010 | Rothberg et al. |
| 2010/0072080 A1 | 3/2010 | Karhanek et al. |
| 2010/0078325 A1 | 4/2010 | Oliver |
| 2010/0105035 A1 | 4/2010 | Hashsham et al. |
| 2010/0112588 A1 | 5/2010 | Farinas et al. |
| 2010/0137143 A1 | 6/2010 | Rothberg et al. |
| 2010/0151479 A1 | 6/2010 | Toumazou et al. |
| 2010/0159461 A1 | 6/2010 | Toumazou et al. |
| 2010/0163414 A1 | 7/2010 | Gillies et al. |
| 2010/0167938 A1 | 7/2010 | Su et al. |
| 2010/0188073 A1 | 7/2010 | Rothberg et al. |
| 2010/0197507 A1 | 8/2010 | Rothberg et al. |
| 2010/0209922 A1 | 8/2010 | Williams et al. |
| 2010/0255595 A1* | 10/2010 | Toumazou et al. .. C12Q 1/6825 436/94 |
| 2010/0282617 A1 | 11/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0317531 A1 | 12/2010 | Balasubramanian et al. |
| 2010/0330570 A1 | 12/2010 | Vander Horn et al. |
| 2011/0008775 A1 | 1/2011 | Gao et al. |
| 2011/0039266 A1 | 2/2011 | Williams et al. |
| 2011/0117026 A1 | 5/2011 | Tseng et al. |
| 2011/0118139 A1 | 5/2011 | Mehta et al. |
| 2011/0123991 A1 | 5/2011 | Hoser |
| 2011/0159481 A1 | 6/2011 | Liu et al. |
| 2011/0171655 A1 | 7/2011 | Esfandyarpour et al. |
| 2011/0177498 A1 | 7/2011 | Clarke et al. |
| 2011/0183321 A1 | 7/2011 | Williams et al. |
| 2011/0195253 A1 | 8/2011 | Hinz et al. |
| 2011/0195459 A1 | 8/2011 | Hinz et al. |
| 2011/0201057 A1 | 8/2011 | Carr et al. |
| 2011/0201506 A1 | 8/2011 | Hinz et al. |
| 2011/0217697 A1 | 9/2011 | Rothberg et al. |
| 2011/0230375 A1 | 9/2011 | Rothberg et al. |
| 2011/0241081 A1 | 10/2011 | Rothberg et al. |
| 2011/0247933 A1 | 10/2011 | Rothberg et al. |
| 2011/0248319 A1 | 10/2011 | Rothberg et al. |
| 2011/0248320 A1 | 10/2011 | Rothberg et al. |
| 2011/0259745 A1 | 10/2011 | Dehlinger et al. |
| 2011/0263463 A1 | 10/2011 | Rothberg et al. |
| 2011/0287432 A1 | 11/2011 | Wong et al. |
| 2011/0287945 A1 | 11/2011 | Rothberg et al. |
| 2011/0294115 A1 | 12/2011 | Williams et al. |
| 2011/0311979 A1 | 12/2011 | Brown et al. |
| 2012/0013392 A1 | 1/2012 | Rothberg et al. |
| 2012/0014837 A1 | 1/2012 | Fehr et al. |
| 2012/0021918 A1 | 1/2012 | Bashir et al. |
| 2012/0034607 A1 | 2/2012 | Rothberg et al. |
| 2012/0037961 A1 | 2/2012 | Rothberg et al. |
| 2012/0040844 A1 | 2/2012 | Rothberg et al. |
| 2012/0045844 A1 | 2/2012 | Rothberg et al. |
| 2012/0052489 A1 | 3/2012 | Gordon et al. |
| 2012/0055811 A1 | 3/2012 | Rothberg et al. |
| 2012/0055813 A1 | 3/2012 | Rothberg et al. |
| 2012/0061239 A1 | 3/2012 | Elibol et al. |
| 2012/0061255 A1 | 3/2012 | Rothberg et al. |
| 2012/0061256 A1 | 3/2012 | Rothberg et al. |
| 2012/0061733 A1 | 3/2012 | Rothberg et al. |
| 2012/0065093 A1 | 3/2012 | Rothberg et al. |
| 2012/0071363 A1 | 3/2012 | Rothberg et al. |
| 2012/0085660 A1 | 4/2012 | Rothberg et al. |
| 2012/0088682 A1 | 4/2012 | Rothberg et al. |
| 2012/0094871 A1 | 4/2012 | Hinz et al. |
| 2012/0129173 A1 | 5/2012 | Piepenburg et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0135893 A1 | 5/2012 | Drmanac et al. |
| 2012/0138460 A1 | 6/2012 | Baghbani-Parizi et al. |
| 2012/0156728 A1 | 6/2012 | Li et al. |
| 2012/0157322 A1 | 6/2012 | Myllykangas et al. |
| 2012/0173159 A1 | 7/2012 | Davey et al. |
| 2012/0175252 A1 | 7/2012 | Toumazou et al. |
| 2012/0222496 A1 | 9/2012 | Mamigonians |
| 2012/0247977 A1 | 10/2012 | Rothberg et al. |
| 2012/0258456 A1 | 10/2012 | Armes et al. |
| 2012/0258499 A1 | 10/2012 | Piepenburg et al. |
| 2012/0264617 A1 | 10/2012 | Pettit |
| 2012/0295819 A1 | 11/2012 | Leamon et al. |
| 2012/0302454 A1 | 11/2012 | Esfandyarpour |
| 2012/0322054 A1 | 12/2012 | Rothberg et al. |
| 2012/0322113 A1 | 12/2012 | Erlander et al. |
| 2013/0005613 A1 | 1/2013 | Leamon et al. |
| 2013/0023011 A1 | 1/2013 | Leamon et al. |
| 2013/0059290 A1 | 3/2013 | Armes |
| 2013/0059762 A1 | 3/2013 | Leamon et al. |
| 2013/0090860 A1 | 4/2013 | Sikora et al. |
| 2013/0096013 A1 | 4/2013 | Esfandyarpour et al. |
| 2013/0109577 A1 | 5/2013 | Korlach et al. |
| 2013/0183211 A1 | 7/2013 | Senftleber |
| 2013/0203634 A1 | 8/2013 | Jovanovich et al. |
| 2013/0225421 A1 | 8/2013 | Li et al. |
| 2013/0231254 A1 | 9/2013 | Kawashima et al. |
| 2013/0281307 A1 | 10/2013 | Li et al. |
| 2014/0034497 A1 | 2/2014 | Davis et al. |
| 2014/0045701 A1 | 2/2014 | Esfandyarpour et al. |
| 2014/0057339 A1 | 2/2014 | Esfandyarpour et al. |
| 2014/0099674 A1 | 4/2014 | Piepenburg et al. |
| 2014/0106338 A1 | 4/2014 | Fischer et al. |
| 2014/0235457 A1 | 8/2014 | Esfandyarpour et al. |
| 2014/0272952 A1 | 9/2014 | May et al. |
| 2014/0329699 A1 | 11/2014 | Esfandyarpour |
| 2015/0148264 A1 | 5/2015 | Esfandyarpour et al. |
| 2015/0316502 A1 | 11/2015 | Mohanty et al. |
| 2015/0344943 A1 | 12/2015 | Oberstrass |
| 2015/0376681 A1 | 12/2015 | Gupta et al. |
| 2015/0376692 A1 | 12/2015 | Esfandyarpour et al. |
| 2016/0076097 A1 | 3/2016 | Esfandyarpour et al. |
| 2016/0077049 A1 | 3/2016 | Baghbani-Parizi et al. |
| 2016/0273032 A1 | 9/2016 | Esfandyarpour et al. |
| 2016/0340721 A1 | 11/2016 | Esfandyarpour |
| 2017/0065977 A1 | 3/2017 | Esfandyarpour et al. |
| 2017/0088575 A1 | 3/2017 | Ju et al. |
| 2017/0211141 A1 | 7/2017 | Gordon et al. |
| 2019/0017103 A1 | 1/2019 | Esfandyarpour |

FOREIGN PATENT DOCUMENTS

| | | |
|---|---|---|
| CN | 101405083 A | 4/2009 |
| CN | 101848757 A | 9/2010 |
| CN | 101918590 A | 12/2010 |
| CN | 102980922 A | 3/2013 |

(56) References Cited

FOREIGN PATENT DOCUMENTS

| | | |
|---|---|---|
| EP | 0676623 A2 | 10/1995 |
| EP | 1499738 B1 | 7/2008 |
| EP | 1992706 A2 | 11/2008 |
| EP | 2290096 A2 | 3/2011 |
| EP | 2336361 A2 | 6/2011 |
| EP | 2428588 A2 | 3/2012 |
| EP | 2287341 B1 | 2/2013 |
| EP | 1759012 B1 | 5/2013 |
| EP | 2660336 A1 | 11/2013 |
| JP | 2006512583 A | 4/2006 |
| JP | 2008525822 A | 7/2008 |
| JP | 2010517040 A | 5/2010 |
| JP | 2010517041 A | 5/2010 |
| JP | 2010518401 A | 5/2010 |
| WO | WO-0118246 A1 | 3/2001 |
| WO | WO-0137958 A2 | 5/2001 |
| WO | WO-0142508 A2 | 6/2001 |
| WO | WO-0227909 A2 | 4/2002 |
| WO | WO-02061146 A1 | 8/2002 |
| WO | WO-2005008450 A2 | 1/2005 |
| WO | WO-2005108612 A2 | 11/2005 |
| WO | WO-2005121363 A2 | 12/2005 |
| WO | WO-2007030505 A1 | 3/2007 |
| WO | WO-2007041619 A2 | 4/2007 |
| WO | WO-2007098049 A2 | 8/2007 |
| WO | WO-2008076406 A2 | 6/2008 |
| WO | WO-2008132643 A1 | 11/2008 |
| WO | WO-2009012112 A1 | 1/2009 |
| WO | WO-2009052348 A2 | 4/2009 |
| WO | WO-2009074926 A1 | 6/2009 |
| WO | WO-2009122159 A2 | 10/2009 |
| WO | WO-2009150467 A1 | 12/2009 |
| WO | WO-2010008480 A2 | 1/2010 |
| WO | WO-2010026488 A2 | 3/2010 |
| WO | WO-2010037085 A1 * | 4/2010 ............ B82Y 15/00 |
| WO | WO-2010041231 A2 | 4/2010 |
| WO | WO-2010047804 A1 | 4/2010 |
| WO | WO-2010075188 A2 | 7/2010 |
| WO | WO-2010138187 A1 | 12/2010 |
| WO | WO-2010141940 A1 | 12/2010 |
| WO | WO-2011106556 A2 | 9/2011 |
| WO | WO-2012047889 A2 | 4/2012 |
| WO | WO-2012166742 A2 | 12/2012 |
| WO | WO-2013082619 A1 | 6/2013 |
| WO | WO-2013119765 A1 | 8/2013 |
| WO | WO-2013188582 A1 | 12/2013 |
| WO | WO-2014012107 A2 | 1/2014 |
| WO | WO-2014043143 A1 | 3/2014 |
| WO | WO-2014152625 A1 | 9/2014 |
| WO | WO-2015089238 A1 | 6/2015 |
| WO | WO-2015138696 A1 | 9/2015 |
| WO | WO-2015161054 | 10/2015 |
| WO | WO-2018017884 | 1/2018 |
| WO | WO-2019060628 A1 | 3/2019 |

OTHER PUBLICATIONS

Notice of Allowance dated Jul. 31, 2017 for U.S. Appl. No. 14/119,859.
European Search Report dated Nov. 14, 2017 for European Patent Application No. EP15779780.4.
Notice of Allowance dated Dec. 8, 2017 for U.S. Appl. No. 14/119,859.
Office Action dated Dec. 18, 2017 for U.S. Appl. No. 15/028,899.
Smolina et al. End invasion of peptide nucleic acids (PNAs) with mixed-base composition into linear DNA duplexes. Nucleic Acids Research. vol. 33. No. 11. pp. e146-e146. Sep. 25, 2005.
Zanoli et al. Isothermal Amplification Methods for the Detection of Nucleic Acids in Microfluidic Devices. Biosensors. vol. 3. No. 1. pp. 18-43. Dec. 27, 2012.
Co-pending U.S. Appl. No. 13/397,581, filed Feb. 15, 2012.
U.S. Appl. No. 14/859,725 Notice of Allowance dated Jul. 27, 2018.
U.S. Appl. No. 15/028,899 Notice of Allowance dated Jul. 25, 2018.
U.S. Appl. No. 16/007,969 Office Action dated Aug. 15, 2018.
Bobrow et al. Fundamentals of Electrical Engineering, 1995, Holt, Rinehart and Winston, Inc.
Brown et al. AC electroosmotic flow in a DNA concentrator. Microfluid Nanofluid 2:513-523 (2006).
Cheng et al. Single-stranded DNA concentration by electrokinetic forces. J. Micro/Nanolith. MEMS MOEMS 8(2):021107 (Jun. 9, 2009). Abstract only.
Co-pending U.S. Appl. No. 15/950,005, filed Apr. 10, 2018.
Co-pending U.S. Appl. No. 15/896,572, filed Feb. 14, 2018.
Co-pending U.S. Appl. No. 16/007,829, filed Jun. 13, 2018.
Co-pending U.S. Appl. No. 16/007,969, filed Jun. 13, 2018.
Co-pending U.S. Appl. No. 16/039,016, filed Jul. 18, 2018.
Cui et al., "Nanowire Nanosensors for Highly Sensitive and Selective Detection of Biological and Chemical Species", Science, vol. 293, pp. 1289-1292 (2001).
EP14767683.7 Extended European Search Report dated Oct. 25, 2016.
Esfandyarpour. Nano-Biotechnology toward Diagnostic Industry: Obstacles and Opportunities. NSTI-Nanotech, vol. 4, p. 421 (2007). Abstract Only.
Examination Report dated Jun. 7, 2016 for Singapore Patent Application No. SG11201402760V.
Fritz et al. Electronic detection of DNA by its intrinsic molecular charge. PNAS 99(22):14142-14146 (2002).
Hsu et al. Wafer-scale silicon nanopillars and nanocones by Langmuir-Blodgett assembly and etching. Applied Physic Lett. 93:133109-1-133109-3 (2008).
Kuhr. Capillary Electrophoresis. Anal. Chem. 62:403R-414R (1990).
Lei et al. Electrokinetic DNA concentration in Microsystems. Sensors and Actuators. A 156(2) (2009). Abstract only.
Moser et al. Biosensor arrays for simultaneous measurement of glucose, lactate, glutamate, and glutamine. Biosens. & Bioelect. 17:297-302 (2002).
Parizi et al. A Semiconductor Nanobridge Biosensor for Electrical Detection of DNA Hybridization. IEEE Int'l SOI Conference, 2 pgs. (Oct. 6-9, 2008).
Parizi et al. An Internally Amplified Signal SOI Nano-bridge Biosensors for Electrical Detection of DNA Hybridization. IEEE Int'l SOI Conference, 2 pgs. (Oct. 5-8, 2009).
Parizi et al. BioFET for Detection of Biological Species. Stanford University, CIS (Computer-Information-System) Catalog, 1 sheet (2008).
Parizi et al. BioFET Sensor. CIS 2007—Stanford University, 33 pgs. (2007).
Parizi et al. Poster—An Internally Amplified Signal SOI Nanobridge Biosensor for Electrical Detection of DNA Hybridization or Sequence. Poster—1 sheet (Summer 2009).
Parizi et al. Poster BioFET Sensor. CIS 2007—Stanford University, 18 pgs. (2007).
Parizi et al. BioFET Sensor. CIS ADCOM Fall 2009 Stanford University, 28 pgs (Nov. 2009).
Pascault. A Finite Element Study of the DNA Hybridization Kinetics on the Surface of Microfluidic Devices. Thesis, M.S. Chem. Engineer., Worcester Polytechnic Institute, p. 1-148 (Apr. 2007).
PCT/US2014/069624 International Search Report dated May 22, 2015.
Poghossian et al. Possibilities and limitations of label-free detection of DNA hybridization with field-effect-based devices. Sensors and Actuators B 111-112:470-480 (2005).
Ramos et al. AC electric-field-induced fluid flow in microelectrodes. J Colloid Interface Sci 217:420-422 (1999).
U.S. Appl. No. 14/081,358 Notice of Allowance dated May 16, 2016.
U.S. Appl. No. 14/936,245 Notice of Allowance dated Sep. 22, 2017.
U.S. Appl. No. 14/936,245 Notice of Allowance dated Dec. 6, 2017.
Stein, D.; Deurvorst, Z.; van der Heyden, F. H. J.; Koopmans, W. J. A.; Gabel, A.; Dekker, C. Electrokinetic Concentration of DNA Polymers in Nanofluidic Channels. Nano Lett. 2010, 10, 765-772.
U.S. Appl. No. 15/028,899 Notice of Allowance dated Jun. 27, 2018.
U.S. Appl. No. 14/361,902 Notice of Allowance dated May 21, 2018.

(56) References Cited

OTHER PUBLICATIONS

U.S. Appl. No. 14/859,725 Notice of Allowance dated May 30, 2018.
U.S. Appl. No. 15/183,406 Office Action dated Jun. 21, 2018.
U.S. Appl. No. 15/230,048 Notice of Allowance dated Apr. 5, 2018.
Wilke et al. A micromachined capillary electrophoresis chip with fully integrated electrodes for separation and electochemical detection. Biosens. and Bioelect. 19:149-153 (2003).
Williams, et al. Etch rates for micromachining processing. Journal of Microelectromechanical Systems 5(4):761-778 (1996).
Co-pending U.S. Appl. No. 15/726,193, filed Oct. 5, 2017.
Co-pending U.S. Appl. No. 15/726,217, filed Oct. 5, 2017.
European Search Report dated Oct. 11, 2017 for European Patent Application No. EP14869402.9.
Notice of Allowance dated Sep. 8, 2017 for U.S. Appl. No. 14/653,230.
Office Action dated Sep. 1, 2017 for U.S. Appl. No. 14/361,902.
Office Action dated Oct. 23, 2017 for U.S. Appl. No. 14/859,725.
Peng et al. Interdigitated Array Electrodes with Magnetic Function as a Particle-Based Biosensor. Sensors, 2007 IEEE. pp. 1097-1100.
Rothberg, et al. An integrated semiconductor device enabling non-optical genome sequencing. Nature. Jul. 20, 2011; 475(7356); pp. 348-352. With Supplementary Information, 25 pages.
Saias et al. Design, modeling and characterization of microfluidic architectures for high flow rate, small footprint microfluidic systems. Lab Chip. Mar. 7, 2011;11(5):822-32.
Tamayol et al. Laminar Flow in Microchannels With Noncircular Cross Section. J. Fluids Eng 132(11), 111201 (Nov 3, 2010) (9 pages).
Andreotti, et al. Immunoassay of infectious agents. Biotechniques. Oct. 2003;35(4):850-9.
Bell, et al. Detection of Bacillus anthracis DNA by LightCycler PCR. J Clin Microbiol. Aug. 2002;40(8):2897-902.
Boo, et al. Electrochemical nanoneedle biosensor based on multiwall carbon nanotube. Anal Chem. Jan. 15, 2006;78(2):617-20.
Brouns, et al. Small CRISPR RNAs guide antiviral defense in prokaryotes. Science. Aug. 15, 2008;321(5891):960-4.
Cagnin, et al. Overview of electrochemical DNA biosensors: new approaches to detect the expression of life. Sensors (Basel). 2009;9(4):3122-48. doi: 10.3390/s90403122. Epub Apr. 24, 2009.
Carte, et al., Cas6 is an endoribonuclease that generates guide RNAs for invader defense in prokaryotes. Genes Dev. Dec. 15, 2008;22(24):3489-96.
Cho, et al. Bis-aptazyme sensors for hepatitis C virus replicase and helicase without blank signal. Nucleic Acids Res. Nov. 27, 2005;33(20):e177.
Daniels, et al. Label-Free Impedance Biosensors: Opportunities and Challenges. Electroanalysis. Jun. 2007;19(12):1239-1257.
Daniels, et al. Simultaneous Measurement of Nonlinearity and Electrochemical Impedance for Protein Sensing Using Two-Tone Excitation. 30th Annual International IEEE EMBS Conference. Vancouver, British Columbia, Canada, Aug. 20-24, 2008. 5753-5756.
Didion, et al., Invaders: Recognition of Double-Stranded DNA by Using Duplexes Modified with Interstrand Zippers of 2'-O-(Pyren-1-yl)methyl-ribonucleotides. Chembiochem. Sep. 2, 2013;14(13):1534-1538. doi: 10.1002/cbic.201300414. Epub 2013 Aug. 23, 2013.
Dimov, et al. Stand-alone self-powered integrated microfluidic blood analysis system (SIMBAS). Lab Chip. Mar. 7, 2011;11(5):845-50.
Edman, et al. Electric field directed nucleic acid hybridization on microchips. Nucleic Acids Res. Dec. 15, 1997; 25(24): 4907-14.
Ellington, et al. In vitro selection of RNA molecules that bind specific ligands. Nature. Aug. 30, 1990;346(6287):818-22.
Esfandyarpour, et al. 3D modeling of impedance spectroscopy for protein detection in nanoneedle biosensors. Proceedings of the COMSOL Conference 2007, Boston.
Esfandyarpour, et al. 3D Modeling of Impedance Spectroscopy for Protein Detection in Nanoneedle Biosensors. Proceedings of the International COMSOL Conference 2007, Boston, MA, USA, pp. 169-173 (Oct. 4-6, 2007).
Esfandyarpour, et al. A Novel Nanoneedle Biosensor for DNA Sequencing (abstract). Dec. 31, 2008. Available at http://www.nsti.org/Nanotech2008/showabstract.html?absno=1522.
Esfandyarpour, et al. Geometrical Optimization of Pyrophosphate Concentration in Thermosequencing Platform for DNA Sequencing. Proceedings of the COMSOL Conf. 2007, Boston.
European search report and search opinion dated Jan. 5, 2015 for EP Application No. 12792216.9.
European search report and search opinion dated Mar. 12, 2014 for EP Application No. 11831452.5.
European search report and search opinion dated Jul. 13, 2015 for EP Application No. 12852490.7.
Finn, et al. Efficient incorporation of positively charged 2', 3'-dideoxynucleoside-5'-triphosphates by DNA polymerases and their application in 'direct-load' DNA sequencing. Nucleic Acids Res. Aug. 15, 2003;31(16):4769-78.
Gao, et al. Silicon nanowire arrays for label-free detection of DNA. Anal Chem. May 1, 2007;79(9):3291-7. Epub Apr. 4, 2007.
Gardeniers, et al. Silicon micromachined hollow microneedles for transdermal liquid transport. Journal of Microelectromechanical Systems. 2003;12(6):855-862.
Guiducci, et al. A Biosensor for Direct Detection of DNA Sequences Based on Capacitance Measurements. ESSDERC 2002, pp. 479-482.
Haurwitz, et al. Sequence- and structure-specific RNA processing by a CRISPR endonuclease. Science. Sep. 10, 2010;329(5997):1355-8.
Hollis, et al. Structure of the gene 2.5 protein, a single-stranded DNA binding protein encoded by bacteriophage T7. Proc Natl Acad Sci U S A. Aug. 14, 2001;98(17):9557-62. Epub Jul. 31, 2001.
International search report and written opinion dated Feb. 26, 2013 for PCT/US2012/039880.
International search report and written opinion dated Mar. 19, 2013 for PCT/US2012/067645.
International search report and written opinion dated Apr. 13, 2012 for PCT/US2011/054769.
International search report and written opinion dated Aug. 21, 2014 for PCT Application No. PCT/US2014/027544.
International search report and written opinion dated Oct. 26, 2015 for PCT/US2015/026135.
Javanmard, et al. A microfluidic platform for electrical detection of DNA hybridization. Sens Actuators B Chem. May 20, 2011;154(1):22-27. Epub Mar. 30, 2010.
Javanmard, et al. Electrical Detection of Proteins and DNA Using Bioactivated Microfluidic Channels: Theoretical and Experimental Considerations. J Vac Sci Technol B Microelectron Nanometer Struct Process Meas Phenom. Nov. 2009;27(6):3099-3103.
Kaushik, et al. Lack of pain associated with microfabricated microneedles. Anesth Analg. Feb. 2001;92(2):502-4.
Kim, et al. Replication of DNA microarrays prepared by in situ oligonucleotide polymerization and mechanical transfer. Anal Chem. Oct. 1, 2007;79(19):7267-74.
Kitano, et al. Molecular structure of RNA polymerase and its complex with DNA. J Biochem. Jan. 1969;65(1):1-16.
Kunin, et al. Evolutionary conservation of sequence and secondary structures in CRISPR repeats. Genome Biol. 2007;8(4):R61.
Kurosaki, et al. Rapid and simple detection of Ebola virus by reverse transcription-loop-mediated isothermal amplification. J Virol Methods. Apr. 2007;141(1):78-83.
Lee, et al. Ion-sensitive field-effect transistor for biological sensing. Sensors (Basel). 2009;9(9):7111-31. doi: 10.3390/s90907111. Epub Sep. 7, 2009.
Lin, et al. Replication of DNA microarrays from zip code masters. J Am Chem Soc. Mar. 15, 2006;128(10):3268-72.
Liu, et al. Immobilization of DNA onto poly(dimethylsiloxane) surfaces and application to a microelectrochemical enzyme-amplified DNA hybridization assay. Langmuir. Jul. 6, 2004;20(14):5905-10.

(56) References Cited

OTHER PUBLICATIONS

Makarova, et al. A putative RNA-interference-based immune system in prokaryotes: computational analysis of the predicted enzymatic machinery, functional analogies with eukaryotic RNAi, and hypothetical mechanisms of action. Biol Direct. Mar. 16, 2006;1:7.
Manickam, et al. A CMOS Electrochemical Impedance Spectroscopy (EIS) Biosensor Array. IEEE Trans Biomed Circuits Syst. Dec. 2010;4(6):379-90. doi: 10.1109/TBCAS.2010.2081669.
Margulies, et al. Genome sequencing in microfabricated high-density picolitre reactors. Nature. Sep. 15, 2005;437(7057):376-80. Epub Jul. 31, 2005.
Notice of allowance dated Mar. 28, 2016 for U.S. Appl. No. 13/481,858.
Notice of Allowance dated May 12, 2017 for U.S. Appl. No. 14/653,230.
Notice of allowance dated May 19, 2016 for U.S. Appl. No. 13/481,858.
Notice of allowance dated Jun. 3, 2015 for U.S. Appl. No. 14/596,111.
Notice of allowance dated Jul. 1, 2015 for U.S. Appl. No. 13/824,129.
Notice of allowance dated Jul. 13, 2015 for U.S. Appl. No. 14/596,111.
Notice of allowance dated Aug. 25, 2015 for U.S. Appl. No. 14/596,111.
Notice of allowance dated Sep. 1, 2015 for U.S. Appl. No. 14/596,111.
Notice of allowance dated Nov. 21, 2014 for U.S. Appl. No. 13/632,513.
Notice of allowance dated Dec. 3, 2015 for U.S. Appl. No. 13/838,816.
Notice of allowance dated Dec. 15, 2015 for U.S. Appl. No. 13/838,816.
Notomi, et al. Loop-mediated isothermal amplification of DNA. Nucl Acids Res. Jun. 15, 2000; 28(12):E63.
Office action dated Jan. 28, 2014 for U.S. Appl. No. 13/838,816.
Office action dated Jan. 29, 2014 for U.S. Appl. No. 13/481,858.
Office action dated Jan. 30, 2015 for U.S. Appl. No. 13/481,858.
Office Action dated Feb. 14, 2017 for U.S. Appl. No. 14/653,230.
Office Action dated Mar. 4, 2016 for U.S. Appl. No. 14/081,358.
Office Action dated Apr. 5, 2017 for U.S. Appl. No. 14/859,725.
Office action dated Apr. 6, 2016 for U.S. Appl. No. 14/835,070.
Office action dated Apr. 9, 2015 for U.S. Appl. No. 14/596,111.
Office Action dated Apr. 24, 2017 for U.S. Appl. No. 14/119,859.
Office action dated May 1, 2015 for U.S. Appl. No. 13/824,129.
Office action dated Jul. 18, 2013 for U.S. Appl. No. 13/481,858.
Office action dated Jul. 23, 2014 for U.S. Appl. No. 13/824,129.
Office action dated Jul. 25, 2014 for U.S. Appl. No. 13/481,858.
Office action dated Sep. 2, 2014 for U.S. Appl. No. 13/632,513.
Office Action dated Oct. 5, 2015 for U.S. Appl. No. 14/081,358.
Office action dated Oct. 7, 2015 for U.S. Appl. No. 13/838,816.
Office action dated Nov. 5, 2013 for U.S. Appl. No. 13/632,513.
Office action dated Dec. 17, 2015 for U.S. Appl. No. 13/481,858.
Office action dated Dec. 17, 2015 for U.S. Appl. No. 14/835,070.
Office action dated Dec. 19, 2014 for U.S. Appl. No. 13/838,816.
Patolsky, et al. Electrical detection of single viruses. Proc Natl Acad Sci U S A. Sep. 28, 2004;101(39):14017-22. Epub Sep. 13, 2004.
Patolsky, et al. Fabrication of silicon nanowire devices for ultrasensitive, label-free, real-time detection of biological and chemical species. Nat Protoc. 2006;1(4):1711-24.
Piepenburg, et al. DNA detection using recombination proteins. PLoS Biol. Jul. 2006;4(7):e204.
Ren, et al. Rapid and sensitive detection of hepatitis B virus 1762T/1764A double mutation from hepatocellular carcinomas using LNA-mediated PCR clamping and hybridization probes. Journal of Virological Methods. 2009; 158(1-2):24-29.
Roosen-Runge, et al. Protein diffusion in crowded electrolyte solutions. Biochim Biophys Acta. Jan. 2010;1804(1):68-75. doi: 10.1016/j.bbapap.2009.07.003. Epub Jul. 17, 2009.
Sabounchi, et al. Sample concentration and impedance detection on a microfluidic polymer chip. Biomed Microdevices. Oct. 2008;10(5):661-70. doi: 10.1007/s10544-008-9177-4.
Safir, et al. Fabrication of an insulated probe on a self-assembled metallic nanowire for electrochemical probing in cells. IEEE 2006, pp. 898-900.
Senapati, et al. A nonmembrane-based nucleic acid sensing platform for portable diagnostics. Topics in Current Chemistry. Apr. 27, 2011; 304:153-169.
Sivamani, et al. Microneedles and transdermal applications. Expert Opin Drug Deliv. Jan. 2007;4(1):19-25.
Sosnowski, et al. Rapid determination of single base mismatch mutations in DNA hybrids by direct electric field control. Proc Natl Acad Sci U S A. Feb. 18, 1997; 94(4): 1119-1123.
Terns, et al. CRISPR-based adaptive immune systems. Curr Opin Microbiol. Jun. 2011;14(3):321-7.
Van Der Oost, et al. CRISPR-based adaptive and heritable immunity in prokaryotes. Trends Biochem Sci. Aug. 2009;34(8):401-7.
Voelkerding, et al. Next generation sequencing: from basic research to diagnostics. Clin. Chem. 2009; 55(4):641-658.
Wang, et al. Interaction of the Cas6 riboendonuclease with CRISPR RNAs: recognition and cleavage. Structure. Feb. 9, 2011;19(2):257-64.
Yazdanpanah, et al. Selective self-assembly at room temperature of individual freestanding Ag2Ga alloy nanoneedles. J. Appl. Phys. 98, pp. 073510-073517 (2005).
Zhang, et al. Dielectrophoresis for manipulation of micro/nano particles in microfluidic systems. Anal Bioanal Chem. Jan. 2010;396(1): 401-20.
Zheng, et al. Multiplexed electrical detection of cancer markers with nanowire sensor arrays. Nat Biotechnol. Oct. 2005;23(10):1294-301. Epub Sep. 18, 2005.
Betz et al. KlenTaq polymerase replicates unnatural base pairs by inducing a Watson-Crick geometry. Nat Chem Biol 8:612-614 (2012).
Co-pending U.S. Appl. No. 16/105,480, filed Aug. 20, 2018.
Co-pending U.S. Appl. No. 16/115,344, filed Aug. 28, 2018.
Co-pending U.S. Appl. No. 16/137,408, filed Sep. 20, 2018.
Co-pending U.S. Appl. No. 16/141,215, filed Sep. 25, 2018.
Co-pending U.S. Appl. No. 16/283,531, filed Feb. 22, 2019.
Co-pending U.S. Appl. No. 16/283,544, filed Feb. 22, 2019.
Park et al. Control of channel doping concentration for enhancing the sensitivity of "top-down" fabricated Si nanochannel FET biosensors. Nanotechnology 20(47):475501 (Oct. 26, 2009).
PCT/US2018/052072 International Search Report and Written Opinion dated Jan. 18, 2019.
U.S. Appl. No. 16/007,969 Notice of Allowance dated Nov. 26, 2018.
U.S. Appl. No. 14/361,902 Office Action dated Oct. 7, 2016.
U.S. Appl. No. 14/859,725 Notice of Allowance dated Sep. 11, 2018.
U.S. Appl. No. 15/183,406 Office Action dated Mar. 8, 2019.
U.S. Appl. No. 15/655,616 Office Action dated Feb. 26, 2019.
U.S. Appl. No. 15/726,193 Office Action dated Apr. 16, 2019.
U.S. Appl. No. 15/726,217 Office Action dated Mar. 19, 2019.
U.S. Appl. No. 16/007,829 Notice of Allowance dated Nov. 26, 2018.
U.S. Appl. No. 16/007,829 Office Action dated Sep. 17, 2018.
U.S. Appl. No. 14/859,725 Notice of Allowance dated Jun. 19, 2018.
U.S. Appl. No. 15/950,005 Office Action dated Jan. 28, 2019.
Sakata et al. DNA Sequencing Based on Intrinsic Molecular Charges. Angew Chem Int Ed 45:2225-2228 (2006).
U.S. Appl. No. 16/283,531 Office Action dated Jul. 18, 2019.
U.S. Appl. No. 16/283,544 Notice of Allowance dated Jul. 11, 2019.
U.S. Appl. No. 15/726,193 Notice of Allowance dated Aug. 29, 2019.
U.S. Appl. No. 15/950,005 Notice of Allowance dated Sep. 13, 2019.
U.S. Appl. No. 16/137,408 Office Action dated Aug. 9, 2019.

\* cited by examiner

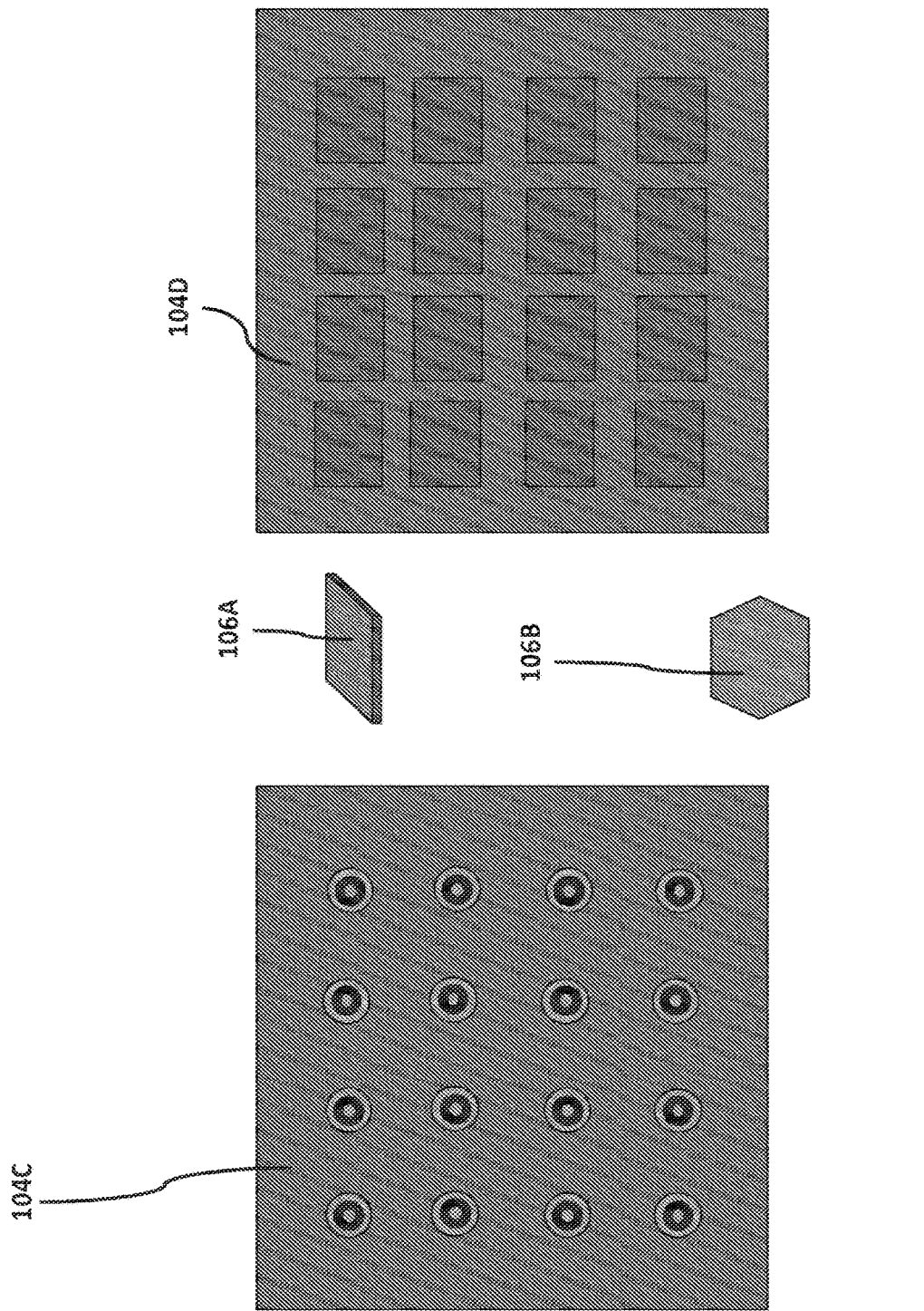

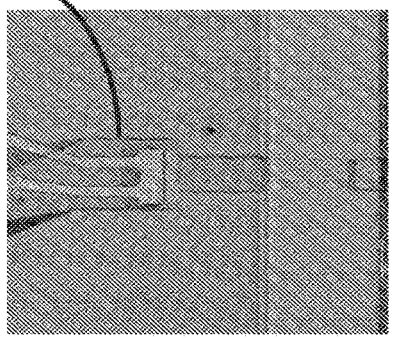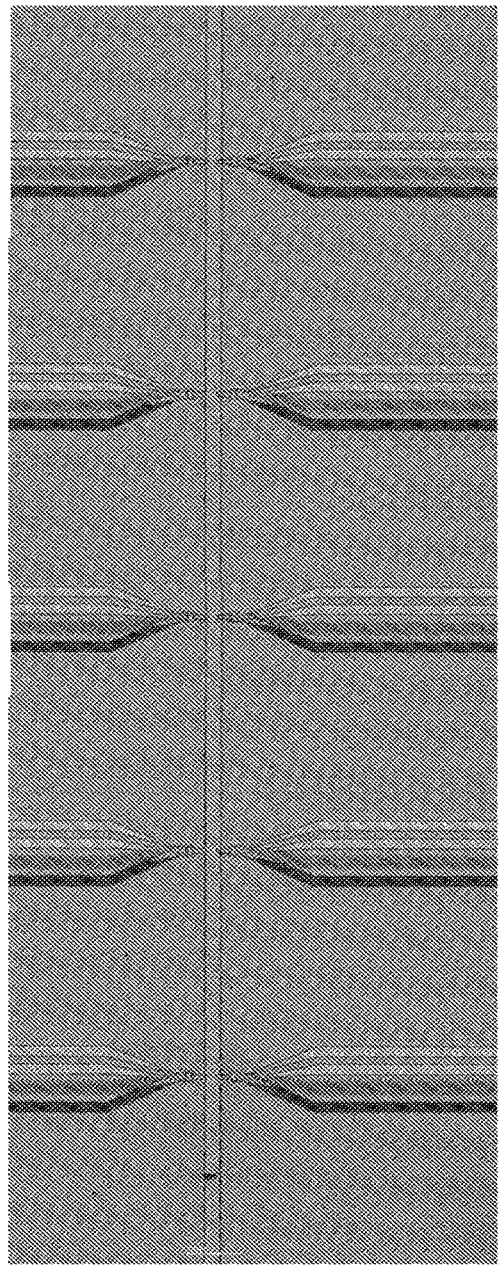
FIG. 8A

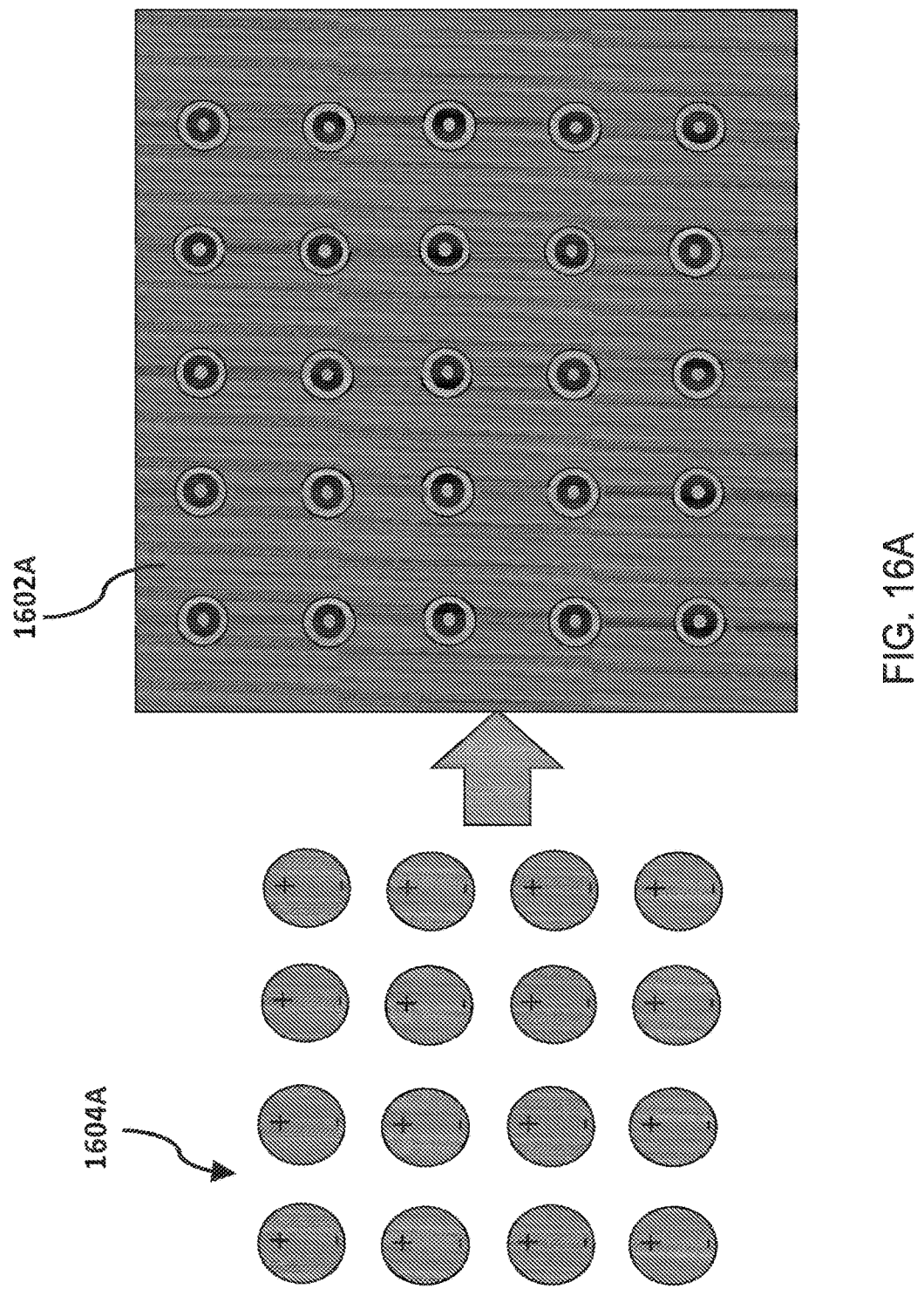

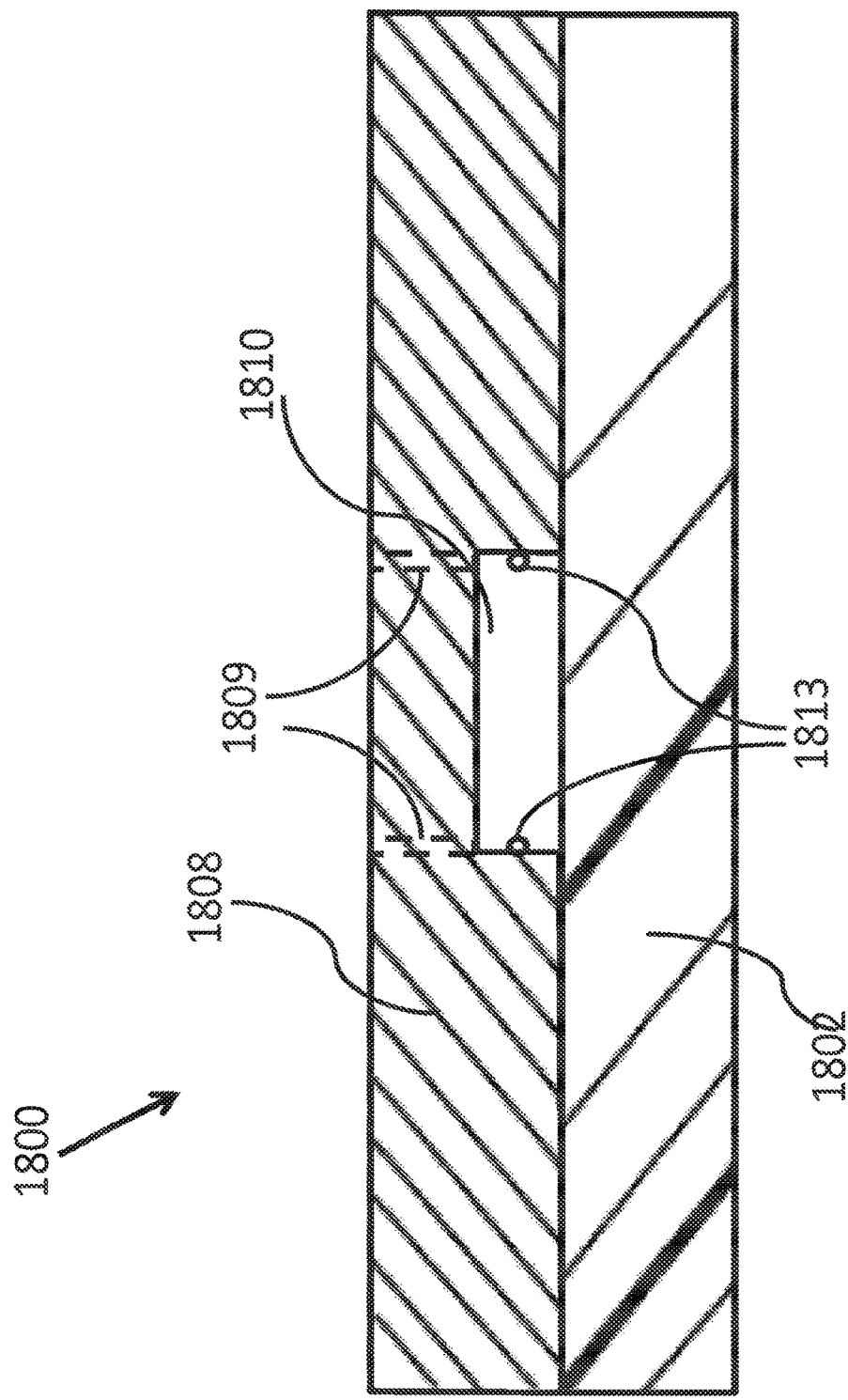

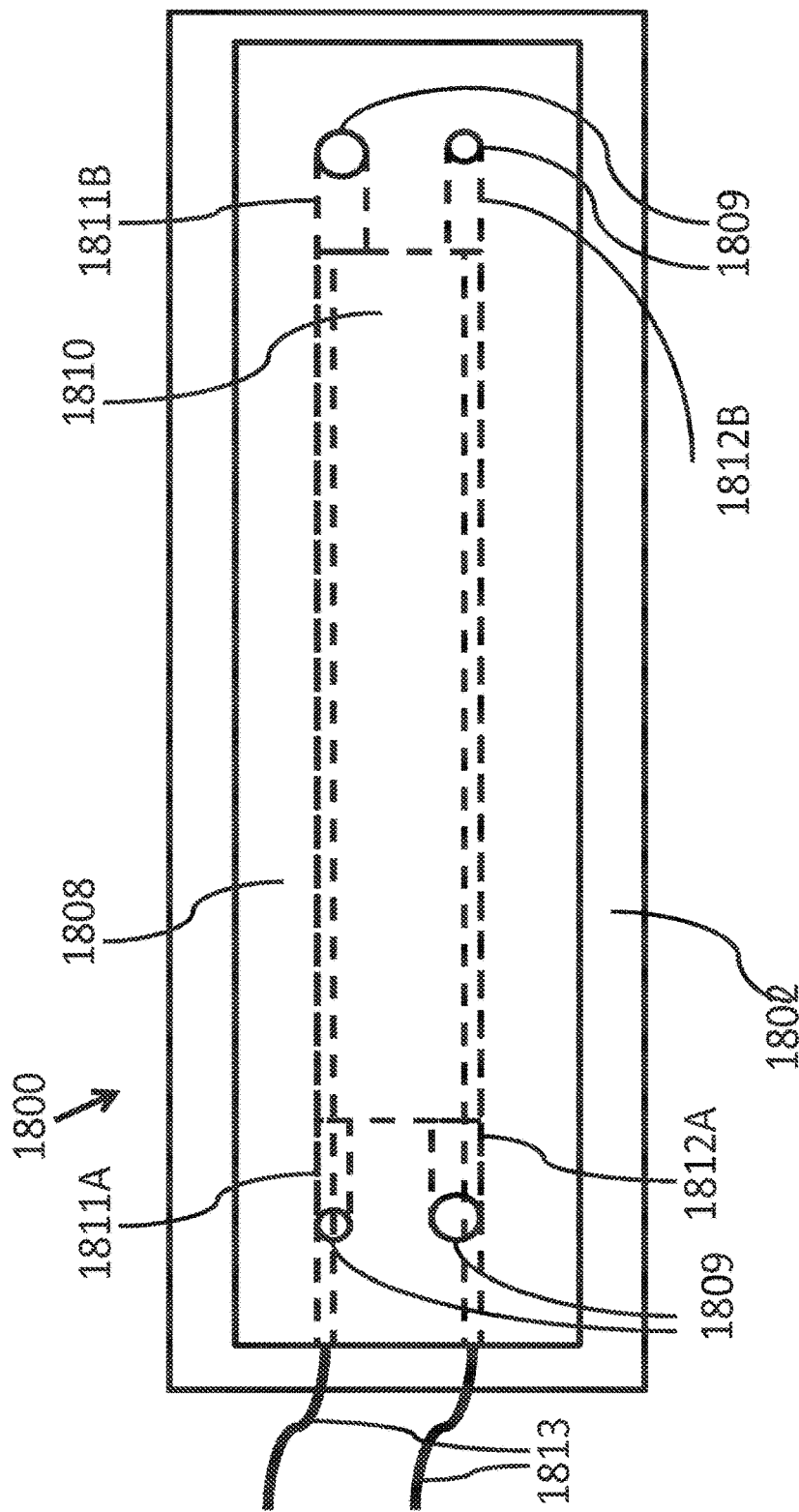

SYSTEMS AND METHODS FOR AUTOMATED REUSABLE PARALLEL BIOLOGICAL REACTIONS

CROSS-REFERENCE TO RELATED APPLICATIONS

This application is a continuation of U.S. patent application Ser. No. 14/835,070, filed on Aug. 25, 2015, which is a continuation of U.S. patent application Ser. No.: 14/596,111 (now U.S. Pat. No. 9,150,915), filed on Jan. 13, 2015, which is a continuation of U.S. patent application Ser. No. 13/632, 513 (now U.S. Pat. No. 8,969,002) filed on Oct. 1, 2012, which is a continuation of U.S. patent application Ser. No. 13/397,581 filed on Feb. 15, 2012, which is a continuation-in-part of PCT International Application No. PCT/US2011/054769 filed on Oct. 4, 2011, which claim priority to U.S. Provisional Patent Application No. 61/389,484 filed on Oct. 4, 2010, U.S. Provisional Patent Application No. 61/389,490 filed on Oct. 4, 2010, U.S. Provisional Patent Application No. 61/443,167 filed on Feb. 15, 2011 and U.S. Provisional Patent Application No. 61/491,081 filed on May 27, 2011, each of which is incorporated herein by reference in its entirety for all purposes.

STATEMENT REGARDING FEDERALLY SPONSORED RESEARCH AND DEVELOPMENT

This invention was made with government support under a Qualifying Therapeutic Discovery Grant awarded by the IRS, in conjunction with the Department of Health and Human Services. The U.S. government has certain rights in the invention.

BACKGROUND

Methods for quick and cost effective DNA sequencing (e.g. at high-throughput) remain an important aspect of advancing personalized medicine and diagnostic testing. Some known systems for DNA sequencing require that DNA samples be transferred between various subsystems between the nucleic acid isolation subsystem and the amplification subsystem), thus resulting in inefficiencies and potential contamination. Some known methods for DNA sequencing employ optical detection, which can be cumbersome, expensive, and can limit throughput. Other systems utilize some forms of electronic sensing, but the sensor and sequencing flow cell are one-time use disposables, which substantially increase the cost to the user, and limits the complexity of the sensor which may be cost effectively manufactured, as it will be thrown out after a single use. Some systems utilize amplification methods within the same flow cell, in which the sequencing is performed, binding the amplified directly to the flow cell, preventing reuse. Other systems utilize emulsion PCR, wherein beads and samples are mixed into small emulsions utilizing low concentrations. Due to Poisson distribution, most of the beads and sample do not come together in an emulsion with a single bead and a single sample, and are thus lost. The cost of the beads is a substantial portion of the cost of the sequencing, and most of that cost is thrown away without ever generating any useful data. The current system enables utilization of virtually all of the sample, and the reuse of the beads, thus reducing the cost to the user.

Current DNA sequencing systems typically need whole genome amplification in order to have sufficient sample, as the sample is very inefficiently utilized. Such whole genome amplification methods typically introduce significant amounts of bias in amplification in different portions of the genome, and require higher levels of coverage to overcome said bias. Methods for localizing samples, and reagents into a volume wherein a desired reaction or binding may occur is another aspect which is envisioned for the system, which may eliminate or reduce the need for whole genome amplification, and thus reduce the coverage needed.

Thus, a need exists for improved systems and methods for extracting, amplifying and sequencing polynucleotides

SUMMARY

The embodiments described herein relate to systems and methods for extracting, amplifying and sequencing polynucleotides. In some embodiments, the systems and methods can include a fully-automated, integrated platform, thereby reducing the cost, improving throughput and/or simplifying the methods of use.

In one aspect, the invention provides a method for isolating biological material, reactants, and/or reaction byproducts for a reaction, such as a nucleic acid amplification or sequencing reaction. The method comprises magnetically holding a bead carrying biological material (e.g., nucleic acid, which may be in the form of DNA fragments or amplified DNA) in a specific location of a substrate, and applying an electric field local to the bead to isolate the biological material or products or byproducts of reactions of the biological material. For example, the bead is isolated from other beads having associated biological material. The electric field in various embodiments concentrates reagents for an amplification or sequencing reaction, and/or concentrates and isolates detectable reaction by-products. For example, by isolating nucleic acids around individual beads, the electric field can allow for clonal amplification, as an alternative to emulsion PCR. In other embodiments, the electric field isolates a nanosensor proximate to the bead, to facilitate detection of at least one of local pH change, local conductivity change, local charge concentration change and local heat. The beads may be trapped in the form of an array of localized magnetic field regions, In another aspect, the invention provides a method for conducting nucleic acid amplification and/or sequencing. The method comprises applying an electric field for confinement of a biological material to an environment, and conducting nucleic acid amplification and/or nucleic acid sequencing on the biological material. The confinement of the environment from an external environment via the electric field has the effect of isolating the biological material into a plurality of regions. The confinement creates a virtual well facilitating amplification and/or detection, and preventing contamination between virtual wells. In various embodiments, the biological material is associated with a plurality of beads, and the beads are held in place by a localized magnetic field in each of the plurality of regions. In certain embodiments, amplification within the virtual wells generates a clonal population of DNA associated with each of the beads, or on the surface of a sensor.

In another aspect, the invention provides an automated method for separating a population of beads carrying amplified nucleic acids, from a population of beads not carrying amplified nucleic acids. The method comprises separating the populations of beads based on a charge associated with the beads. The separation may be implemented with electrophoresis. The bead separation may be based on a flow-through mechanism, and the beads may be reused in a subsequent amplification reaction, for example, by treating the beads so as to remove any amplified product and/or primer.

In still other aspects, the invention provides a method for purifying DNA fragments from a biological material. The method comprises applying an electric field in a fluidic environment, said fluidic environment at least partially containing a filter medium. In this aspect, the electric field is adapted to separate a DNA fragment from a biological material as the biological material is conveyed through the filter medium. In various embodiments, the filter medium is a porous membrane or a medium providing a different mobility of the DNA fragments compared to a remainder of the biological material. Once purified, the DNA fragments can be used for DNA library construction, DNA amplification, DNA enrichment, and/or DNA sequencing, for example, using the methods and systems described herein.

In yet another aspect, the invention provides a method for shearing DNA isolated from a biological material. The method comprises disposing a plurality of particles in a fluidic environment containing a population of DNA molecules, and causing flow of the particles in the fluidic environment to produce a shearing force on the DNA molecules in order to produce DNA fragments. In such embodiments, the shearing force produces blunt ends to aid in subsequent library construction.

In another aspect, the invention provides a system for nucleic acid amplification and/or sequencing. The system comprises a substantially planar substrate coupled to a moiety for binding a nucleic acid to the substrate, and a means for separating the nucleic acid from the substrate such that the system is reusable for at least one of nucleic acid amplification and nucleic acid sequencing. During amplification, the system generates nucleic acid clones on the surface of the substrate. Amplification may involve either heating cycles or by isothermal amplification. In various embodiments, the system further comprises an instrument for detecting incorporation of a nucleotide in a sequencing reaction. The detection may be based on at least one of local pH change, local heat detection, local capacitance change and a local charge concentration and local conductivity change.

In some aspects, the invention provides a system for detecting biological material or a biological reaction product or byproduct. The system comprises a substantially planar sensor array, the sensor array comprising a means for capturing a bead adjacent to each nanosensor in the array. The nanosensor is capable of detecting biological material or a biological reaction product or byproduct. The system further comprises a means for releasing a bead to facilitate reuse of the array, such as by magnetic, chemical, enzymatic means.

In some embodiments of the methods and systems described herein, an apparatus includes a substrate, a porous member and an electrode. The substrate defines a microfluidic channel configured to receive a sample. The porous member is disposed at least partially within the microfluidic channel. The electrode is configured to produce an electric field, and is coupled to the microfluidic channel such that at least a portion of the porous member may be disposed within the electric field. The porous member and the electric field may be cooperatively configured such that a nucleic acid may be separated from the sample when the sample is conveyed through the porous member.

In some embodiments, an apparatus includes a substrate, a plurality of particles and a flow mechanism. The substrate may define a microfluidic channel configured to receive a sample containing a plurality of DNA molecules. In other embodiments, the apparatus may be used as a probe and inserted into a well or other fluidic environment. The plurality of particles may be configured to be disposed within the microfluidic channel. The mechanism for producing the flow may be configured to produce a flow of the sample and the plurality of particles within the microfluidic channel such that the plurality of particles produces a shear force on the plurality of DNA molecules to produce a plurality of DNA fragments. In some embodiments, an on-chip peristaltic pump, made of multiple fluidic gates with orthogonal control and flow channels (Valve Technology), or an external pressure may generate the required flow in the channel.

The present invention provides magnetic arrays and methods of using the magnetic arrays for polynucleotide amplification and sequence analysis, thereby providing fast, convenient, and/or low-cost DNA sequencing.

BRIEF DESCRIPTION OF THE DRAWINGS

FIG. 1D shows a schematic of a sensor array used with a set of nonspherical magnetic particles.

FIG. 8A depicts an image of a portion of the sequencing system that includes the nanosensors.

FIG. 16A shows a set of beads with clonal DNA attached thereto and a sensor and magnetic array.

FIGS. 18A-B illustrate different views of one embodiment of a bead separation system

DETAILED DESCRIPTION

Figure 1A:
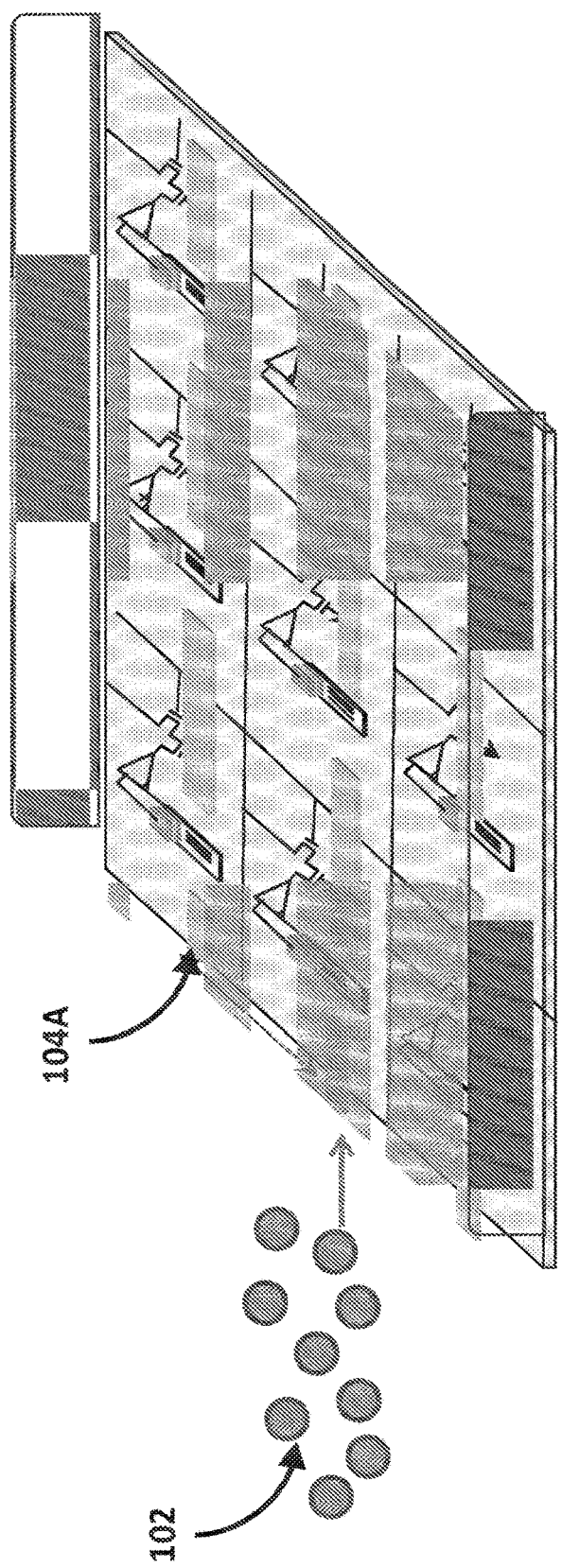
FIG. 1A shows beads and a magnetic array with sensors which may be used to capture the beads.
Figure 1B:
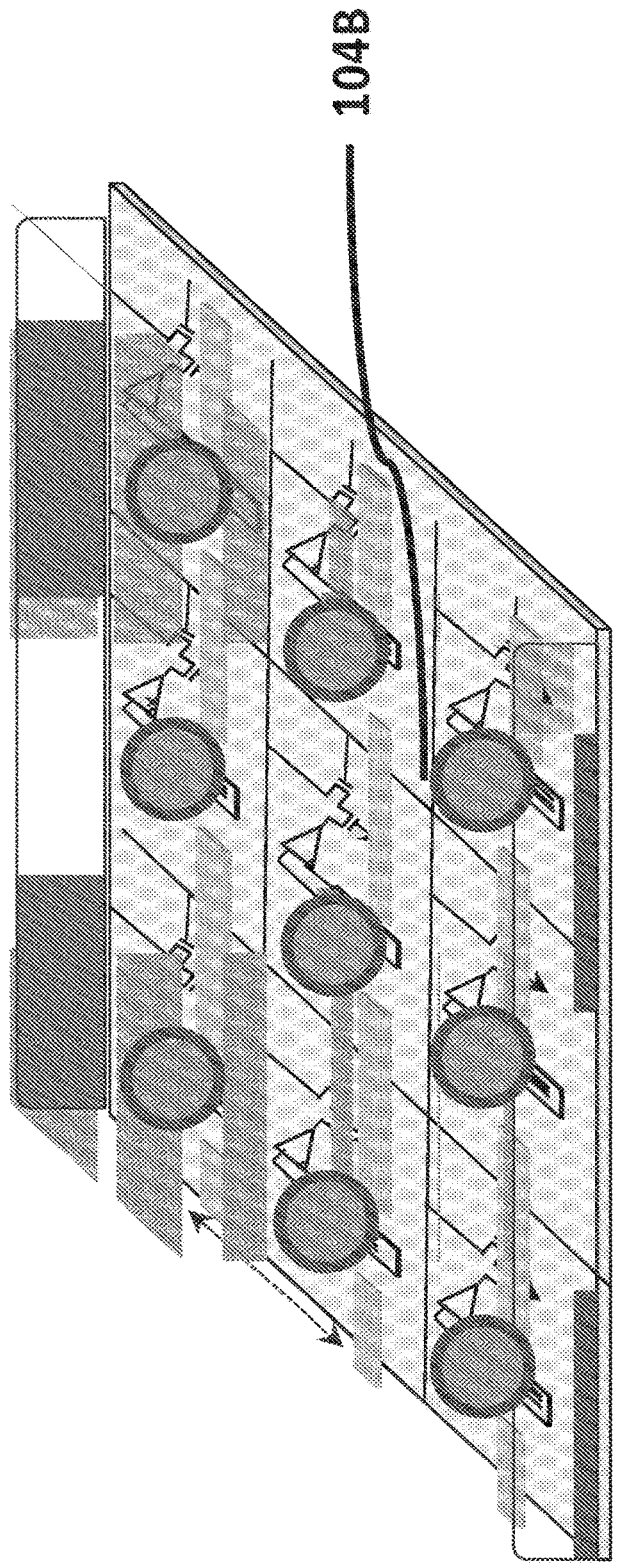
FIG. 1B shows the beads captured on the magnetic array in a one to one correspondence with the sensors.

As used herein, "bead capture features" may mean features that can temporarily hold a single bead in a fixed position relative to the sensor and can include local magnetic structures on the substrate, depressions which may utilize an external magnet, local magnetic structures. Van der Waals forces, or gravity as forces that fix the position of a bead. Optionally, the bead may be bound in place using covalent or non-covalent binding.

As used herein, "clonal" may mean that substantially all of the populations of a bead or particle are of the same nucleic acid sequence. In some embodiments there may be two populations associated with a single sample DNA fragment, as would be desired for "mate pairs," "paired ends", or other similar methodologies; the populations may be present in roughly similar numbers on the bead or particle, and may be randomly distributed over the bead or particle.

As used herein, "confinement" may mean when a molecule generated (such as DNA) at one bead or particle stays associated with the same bead or particle so as to substantially maintain the clonal nature of the beads or particles.

As used herein "isolate" may mean the prevention of migration, diffusion, flow, or other movement, from one virtual well to another virtual well as necessary to maintain the clonal nature of the beads or particles.

As used herein, "localized magnetic feature" may mean a magnetic feature created on a substantially planar substrate to hold individual beads on said substantially planar substrate.

As used herein, "localized magnetic field" may mean a magnetic field that substantially exists in the volume between the north pole of a first magnetic region and the south pole of a second magnetic region or substantially exists in the volume between the north and south poles of a single magnetic region.

As used herein, "localized electric field" may mean an electric field that substantially exists in the volume between at least two electrodes.

As used herein, "nanosensor" may mean a sensor designed to detect beads or particles less than one of 0.1, 1, 5, 10 or 20 micrometers as measured on the diameter or the long axis for non spherical beads or particles. Alternatively, the sensor may be sensitive to moieties associated with said beads or particles, or with reaction products or byproducts wherein the reaction includes a moiety associated with said bead or particle. Said moieties may include DNA fragments, hydrogen ions, or other ions which are counter ions and thus associated with said beads or particles or moieties bound or associated with said beads or particles.

Nanosensors can include "NanoBridge, "NanoNeedle, ISFET, ChemFET, nano-calorimeter or cantilever based pH sensors or combinations thereof.

As used herein, "particle" can mean a non spherical moiety such as a molecule, an aggregation of molecules, molecules bound to a solid particle, or particles, and other forms known in the art.

As used herein, "single phase liquid" is a liquid with relatively uniform physical properties throughout, including such properties as density, index of refraction, specific gravity, and can include aqueous, miscible aqueous and organic mixtures but does not include non miscible liquids such as oil and water. Among the physical properties not considered to potentially cause a liquid to not be considered a single phase liquid include local variations in pH, charge density, and ionic concentration or temperature.

As used herein, "Substantially planar" shall allow small pedestals, raised sections, holes, depressions, or asperity which does not exceed 50 μm relative to the local plane of the device. Variations due to warpage, twist, cupping or other planar distortions are not considered to constitute a portion of the permitted offset. Protrusions or depressions which are not essential for the uses as described herein but which exceed 50 μm do not preclude a device from being considered substantially planar. Fluidic channels and or structures to generate said fluidic channels which have dimensions of greater than 50 μm also do not preclude a device from being considered substantially planar.

As used herein, "virtual wells" refers to local electric field or local magnetic field confinement zones where the species or set of species of interest, typically DNA or beads, substantially does not migrate into neighboring "virtual wells" during a period of time necessary for a desired reaction or interaction.

Figure 3:
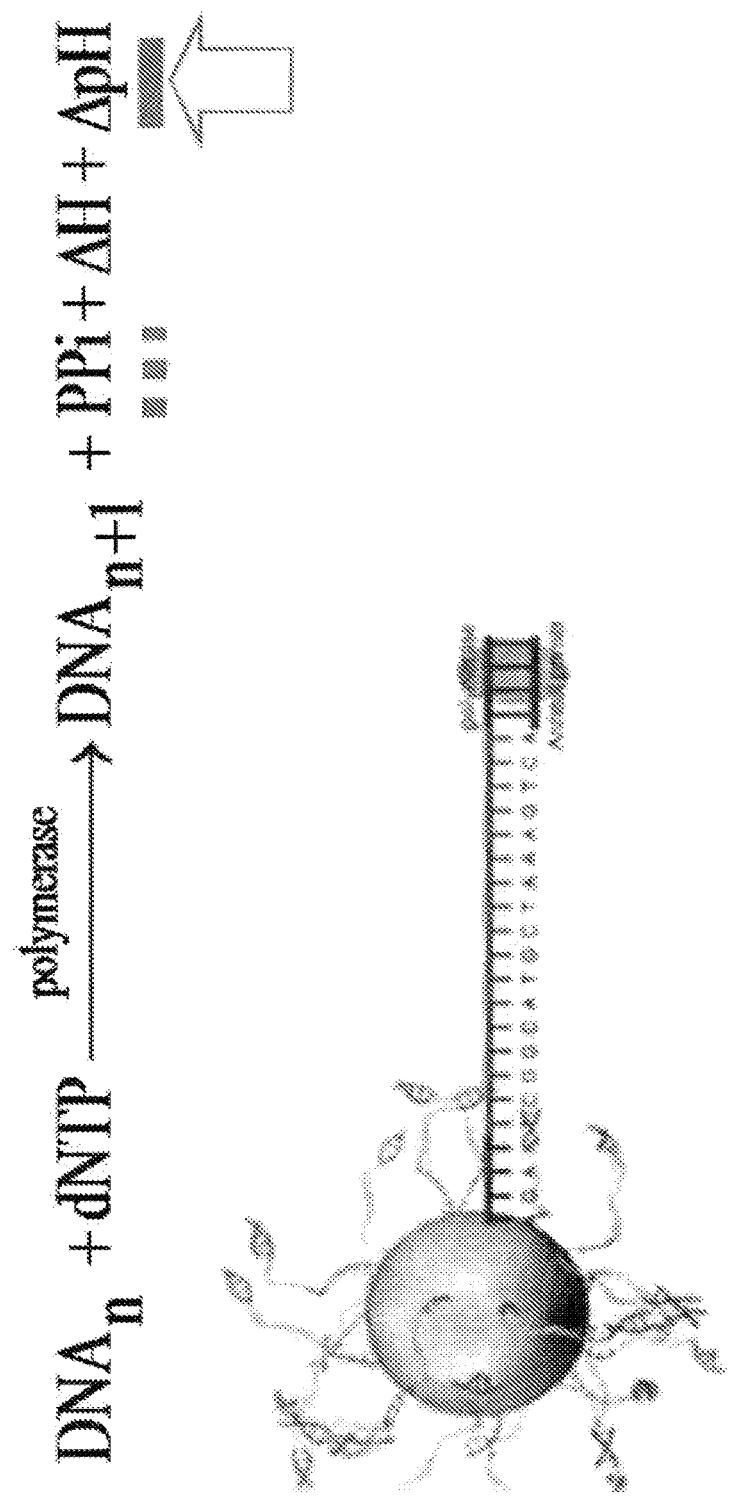
FIGS. 3 and 4 are schematic illustrations of the reaction involved in incorporating nucleotides into a growing DNA strand, showing the release of pyrophosphate and concomitant increase in pH and heat release.

In some embodiments of the current invention, the invention provides an automated reusable system for performing a sequencing chemistry. In some embodiments a chemistry method performed by the system may include sequencing by synthesis, which is schematically shown in FIG. 3, wherein dNTPs bind to a complex which may include a colony of DNA, complementary primers, and polymerase. The polymerase incorporates the dNTP to the growing extended primer, and creates as byproducts of said incorporation hydrogen ions, pyrophosphate and heat which can be detected by electronic sensors. By determining whether a base incorporation has occurred, or if multiple incorporations occurred, and knowing what reagents were delivered before such incorporation the sequence of the DNA can be determined Magnetic Array The present invention provides magnetic arrays and methods of using the magnetic arrays for polynucleotide amplification and sequence analysis, thereby providing fast, convenient, and/or low-cost DNA sequencing. The magnetic array may comprise a substrate having a plurality of magnetic regions thereon to form the array, the localized magnetic fields being sufficient for trapping magnetic beads as described herein. The localized magnetic features may be formed from a permanent magnetic material (e.g., ferromagnetic), or may be non-permanent and magnetized (and demagnetized) by an electric field.

The array may be formed from any of the known substrate materials, as described, for example, in U.S. Pat. No. 7,682,837, which is hereby incorporated by reference. In certain embodiments, the substrate material may include at least one of silicon, silicon-based material, glass, modified or functionalized glass, plastic, metal, ceramic plastics or a combination thereof. The substrate is generally a non-magnetic material.

The localized magnetic features may be created with permanent magnetic material (e.g., ferromagnetic), or may be non-permanent (e.g., electromagnetic-induced regions). In certain embodiments, the plurality of localized magnetic features may be formed from a magnetic material, and each region may be a substantially uniform size and shape, to thereby form an array (e.g., a grid-like pattern), and may thus form a plurality or array of localized magnetic features. In other embodiments, the magnetic features may be non-uniform. In exemplary embodiments, the magnetic features may be magnetic bars, which may be formed at least in part from a magnetic material comprising, for example, aluminum, cobalt, samarium, neodymium, boron, copper, zirconium, platinum, chromium, manganese, strontium, iron and/or nickel, and including alloys thereof, and may include other materials and elements. In a one embodiment, the magnetic features may be formed at least in part from an alloy of nickel and platinum (e.g., about 50%-50%) or an alloy of cobalt and platinum (80% Co 20% Pt) or an alloy of cobalt, chromium and platinum. The localized magnetic fields may be contained within wells on the substrate, or alternatively, the substrate does not contain wells, allowing amplification or sequencing reagents to flow freely over the substrate surface, thereby simplifying the sequential addition and control of reagents (e.g., sequential addition of NTPs for sequencing), which can directly improve dephasing and signal to noise ratio for long read sequencing.

In a further embodiment, well structures, depressions, protrusions, or other means of limiting the motion of a bead or particle may be utilized in combination with localized magnetic fields to retain a bead or particle in a fixed position, forming a bead capture feature.

Various methods of fabrication may be used for creating the localized magnetic features (e.g., magnetic bars). In certain embodiments, the localized magnetic features or bars have sharp edges, which may be fabricated by photolithography and then sputtering of the magnetic layer. In other embodiments, the localized magnetic features (e.g., bars) may be fabricated by sputtering/coating of a magnetic layer, followed by photolithography, and then ion-milling to etch off excess material and creating sharp or specific angle edges. In some embodiments, the fabrication may utilize multi-layer resist lithography.

The localized magnetic features may be configured to be in a single domain state. The localized magnetic features may be fabricated with a number of layers, alternating between a ferromagnetic material and an intermediate layer of another material such as chromium, in order to improve the coercivity of the multilayer magnetic structure. In addition to the alternating layers, there may be a seed layer and a protective layer of a material such as Tantalum, MgO or other appropriate materials as known in the art. There may be a number of alternating layers, for instance 2 to 40 layers, for example, 2 to 4 layers, 5 to 10 layers, 10 to 16 layers, or 16 to 30 layers, or 32 layers or more. The grain orientation may be parallel to the long axis on the localized magnetic features. The thickness of the layers may vary from 5 nm to 15 nm or more for each layer.

In some embodiments, the localized magnetic features may be rectangular prisms, with a length of about 20 microns, with a width of one to 2 microns, and gaps for holding a bead or particle may be 2 to 3.5 microns when the diameter of the bead is 4.5 microns. The lengths, widths, and gaps may all be scaled up or down as appropriate for a larger or smaller bead or particle. For example, for a 2.8 micron bead, the localized magnetic features may have a length of 10 microns, a width of 1 to 2 microns, and a gap for holding said bead or particle of from 1.25 to 2.5 microns.

The array may be a high density or low density array. The arrays generally contain at least 100 magnetic regions per $mm^2$, and in certain embodiments, contain at least 1,000 localized magnetic features per $mm^2$, and in certain embodiments contain at least 100,000 localized magnetic features per $mm^2$. The array may contain at least 1,000, 2000, 4,000, 5,000, 10,000, 100,000, 1,000,000, 10,000,000 or 100,000,000 or more localized magnetic features.

The localized magnetic fields may be sufficient for trapping (by magnetic force) magnetic particles having a size of 50 µm or less. In certain embodiments, the localized magnetic fields may be sufficient for trapping magnetic particles having a size of 20 µm or less, 5 µm or less, 500 nm or less, or 50 nm or less. In certain embodiments, the beads have a diameter of from about 3 µm to about 5 µm, and in other embodiments the beads have a diameter from about 0.5 µm to 3 µm. The magnetic particles may be ferromagnetic, paramagnetic, or superparamagnetic, and suitable materials are well known, as described in U.S. Pat. No. 7,682,837. The beads may be moved into the array by flow, for example, via a channel having a height of from about 5 to 50 µm, such as about 15 µm. The width of the channel may vary, but in some embodiments may be from about 500 µm to 1 mm, such as about 800 µm. In other embodiments the channel width may be from 1 mm to 20 mm or more. In some embodiments the channel may have supporting posts or ribs to better control the height. In other embodiments, parallel channels may be utilized, either to accommodate more array positions for a single sample, or to accommodate multiple samples.

In some embodiments of the current invention, wherein magnetic beads or particles are utilized without a magnetic array, said magnetic beads may self assemble into a monolayer with uniform spacing. In other embodiments the self assembling beads or particles may be nonmagnetic. In some embodiments depressions associated with the sensors can facilitate a one to one correspondence and may result in better alignment between the beads and the sensors permitting better detection. Slow translation or movement of the beads may be appropriate after conditions have been caused to be appropriate for binding, in order to enable alignment of the beads with the sensors. Such translation or movement may occur in multiple dimensions, which may include x, y, theta, and may have varying movements in time and distance to accommodate the spacing of the sensors and the size of the beads. In other embodiments, a circular fluidic movement may be used to ensure high rates of bead loading.

In designs with deep wells beads or particles may not be adequately accessible to fluid flow. In some embodiments, the beads or particles are more accessible to fluid flow, as they may protrude above the surface of the device. As a result, the beads may respond more quickly to introduction of reagents, permitting better, quick and more efficient washes and reactions.

Figure 1C:
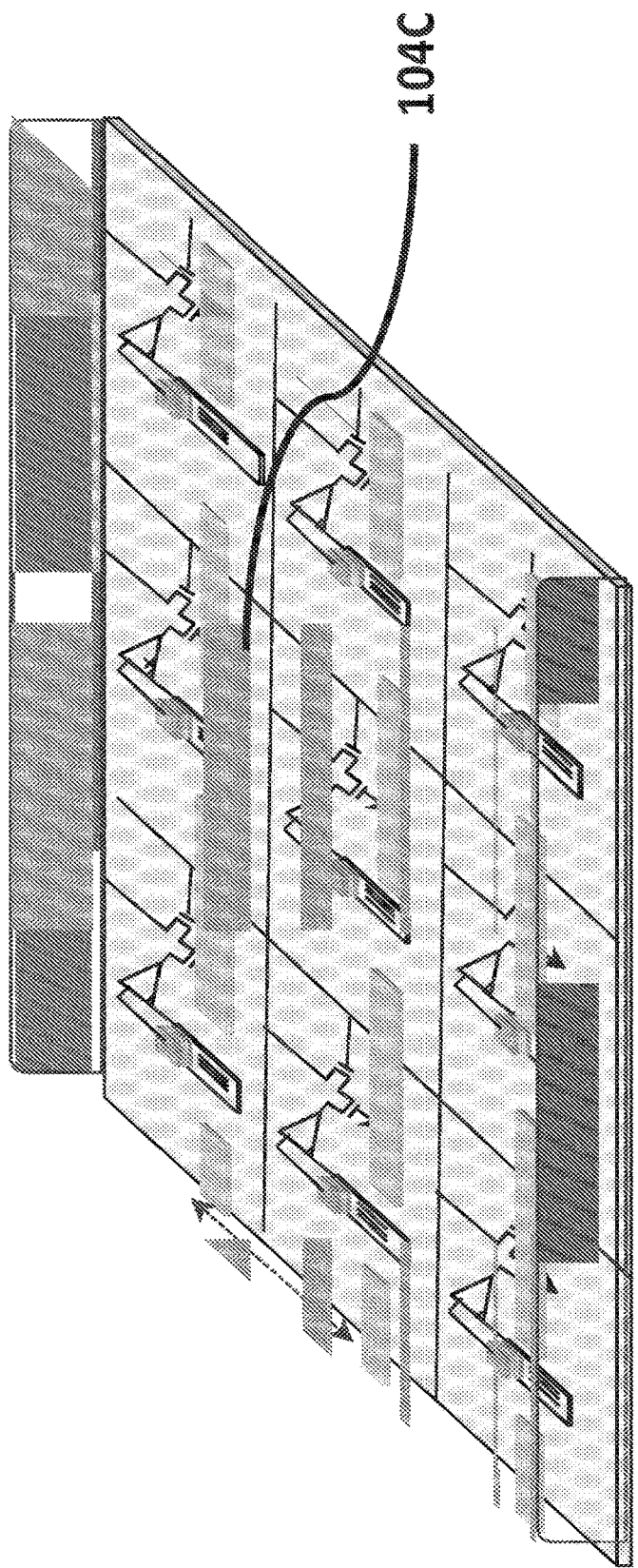
FIG. 1C shows the sensor array after the beads have been washed off ready for use for the next sample.

FIG. 1A schematically illustrates the addition of beads 102 to a magnetic array 104A. FIG. 18 schematically illustrates the positioning of said beads in a one to one correspondence with the retention regions on the array 104B. FIG. 1C shows the sensor array after the beads have been washed off ready for use for the next sample.

FIG. 1D illustrates various embodiments of the current invention wherein the magnetic, paramagnetic, non magnetic particles or a combination thereof may be of shapes other than spherical for use with either a sensor array 104C with magnetic retention, a sensor array with electrical confinement not shown or a sensor array with self assembled particles 104D. In one embodiment said particles may be substantially planar. The substantially planar particles may be round, rectangular 106A, star shaped, hexagonal 106B, or in another shape. In other embodiments, the particle may be dendritic including a dendritic structure formed by a self assembled 3D DNA network, enlarging the surface area of said particle. Said dendritic particle may be generally spherical, substantially planar, oval, or any other shape. In some embodiments, primers may be attached said dendritic particles. In other embodiments DNA nanoballs may be attached to dendritic particles or other types of particles or beads. In yet other embodiments, said particle may be porous or partially porous; if said particle is porous or partially porous, the pore size may be of sufficient size as to permit free movement of DNA, polymerase, dNTPs and other moieties necessary tor primer extension sequencing or other applications as appropriate in all places where the term bead is utilized, it may be assumed that it may be of any shape as described herein.

Figure 2A:
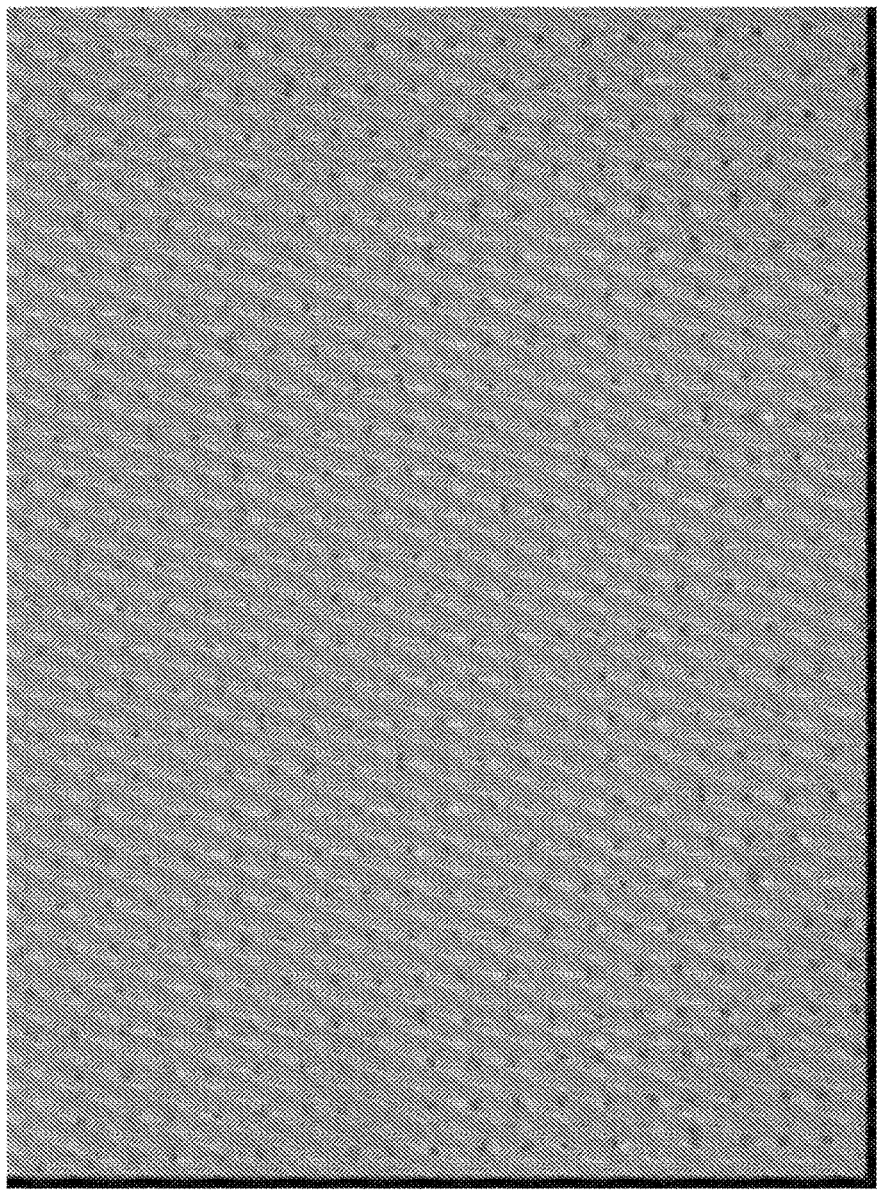
FIGS. 2A-2B Show a photomicrographs of a magnetic arrays according to an embodiment loaded with beads
Figure 2B:
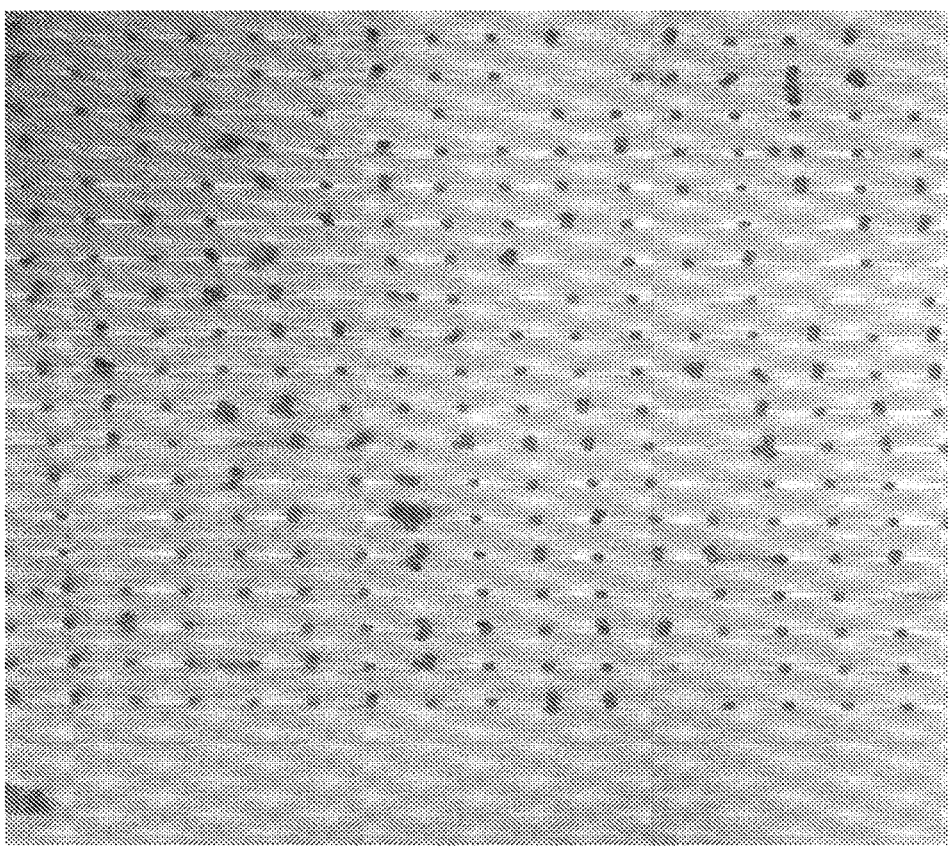

FIGS. 2A and 2B are micrographs of localized magnetic arrays filled with magnetic beads, as described in various embodiments herein, illustrating the routinely high occupancy level achievable and illustrating a further embodiment of the current invention, wherein a single magnetic or paramagnetic bead may be held in place in a single position in the magnetic array. Said beads may be sized such that there may be sufficient room for only one bead over each sensor, thus providing for a one to one correspondence between array positions and beads. Although there may be room for only one bead over each sensor, there can be an additional distance between beads when the beads may be aligned in proximity to the sensors, resulting in reduced cross-talk between sensors. For example, a set of beads may be 10 microns in diameter located over sensors which may be 8 microns across, and the sensors may be spaced 15 microns apart, resulting in a 5 micron space between the beads. The size of the sensors may be larger than the beads, if there is insufficient room for two beads to be retained above the sensor. The size of the beads, sensors, and spacing can vary. In other embodiments, beads may be greater in size than 10 microns, such as 15 microns, 20 microns, 25 microns, or larger. In further embodiments the beads may be smaller than 10 microns, such as 5 microns, 3 microns, 2 microns, 1 micron, or less than one micron. The sensors may be sized to align with the size of the beads, and thus may be larger, or smaller in size than 8 microns across, potentially ranging from less than one micron, to 1, 2, 3, 5, 10, 15, 20 or more microns across, The spacing between the sensors may also be greater than 15 microns, or may be less than 15 microns; the sensor spacing may range from less than one micron, to 1, 2, 3, 5, 10, 15, 20, 25 or more microns between sensors. The sensors can be arranged in a square, rectangular, hexagonal or other 2-D pattern. Although described herein primarily for DNA applications, including amplification, real-time PCR, sequencing, digital PCR, DNA hybridization probe array, the magnetic arrays may be utilized for other applications, such as applications or methods utilizing and or detecting antibodies or other proteins.

In some embodiments with 4.5 um diameter magnetic beads a flow rate of 0.07-0.14 mm/sec may be desirable for bead loading to allow capture by the localized magnetic fields. A flow rate of 1.4-4.2 nm/sec may be desirable for reagent delivery to prevent dislodging of the magnetic beads. A flow rate of >5.6 mm/sec may be desirable for bead removal. In other embodiments the use of air bubbles can be used to remove the beads. Larger and smaller beads may be used with higher and lower flow rates although the relationship may not be linear.

Other Reuse Methods

After a set of sequencing cycles has been completed, the primers may be removed and replaced. Buffer conditions can be changed to weaken a biotin streptavidin bond, such as high concentrations of GuHCl at low pH; alternatively the temperature can be raised to over 70 C to break the biotin streptavidin bond, Lower temperatures may also be used with low ion strength buffers, such as buffers with micro molar salt concentrations. Combinations of the above may also be utilized, such as higher temperatures and low ionic strength buffers. Thiol bonds can likewise be broken at elevated temperatures. Aggressive means may be utilized, as damage to the polymerase and DNA may be no longer consequential, as the sequencing reaction has already been completed. In one embodiment, organic reagents may be utilized to break the binding between the extended primer and the surface, such as a covalent binding. After the extended primers have been removed, new primers may be flowed into the volume above the sensors, enabling the device to be used again for another set of sequencing cycles on another set of DNA samples. Said new primers may be bound in a single phase liquid, Said new primers may also have additional reagents included in the fluid containing said primers which assist binding or associating of the primers to the sensors. The new primers may be utilized in an amplification reaction to generate a new clonal population for subsequent sequence analysis, as described herein. Said amplification may be PCR or isothermal amplification.

in a further embodiment, an amplification or sequencing array may be reused by the removal of beads. Said removal may be done, for example, by the application of an external magnet field, which may result from the movement of a permanent magnet or the activation of an electro magnet, to pull, move or dislodge beads or particles from wherein they are held in said amplification or sequencing array.

In an alternative embodiment, wherein said beads or particles are held in place with a Biotin Streptavidin binding, thiol binding, DNA, LNA, PNA, or other nucleic analog hybridization, or the like, the release of said binding may be achieved by changing the temperature and or fluidic environment proximate the bead or particle, so as to reversibly break the binding, so that new beads or particles may be subsequently bound or associated in the amplification or sequencing array.

Sequencing

Figure 4:
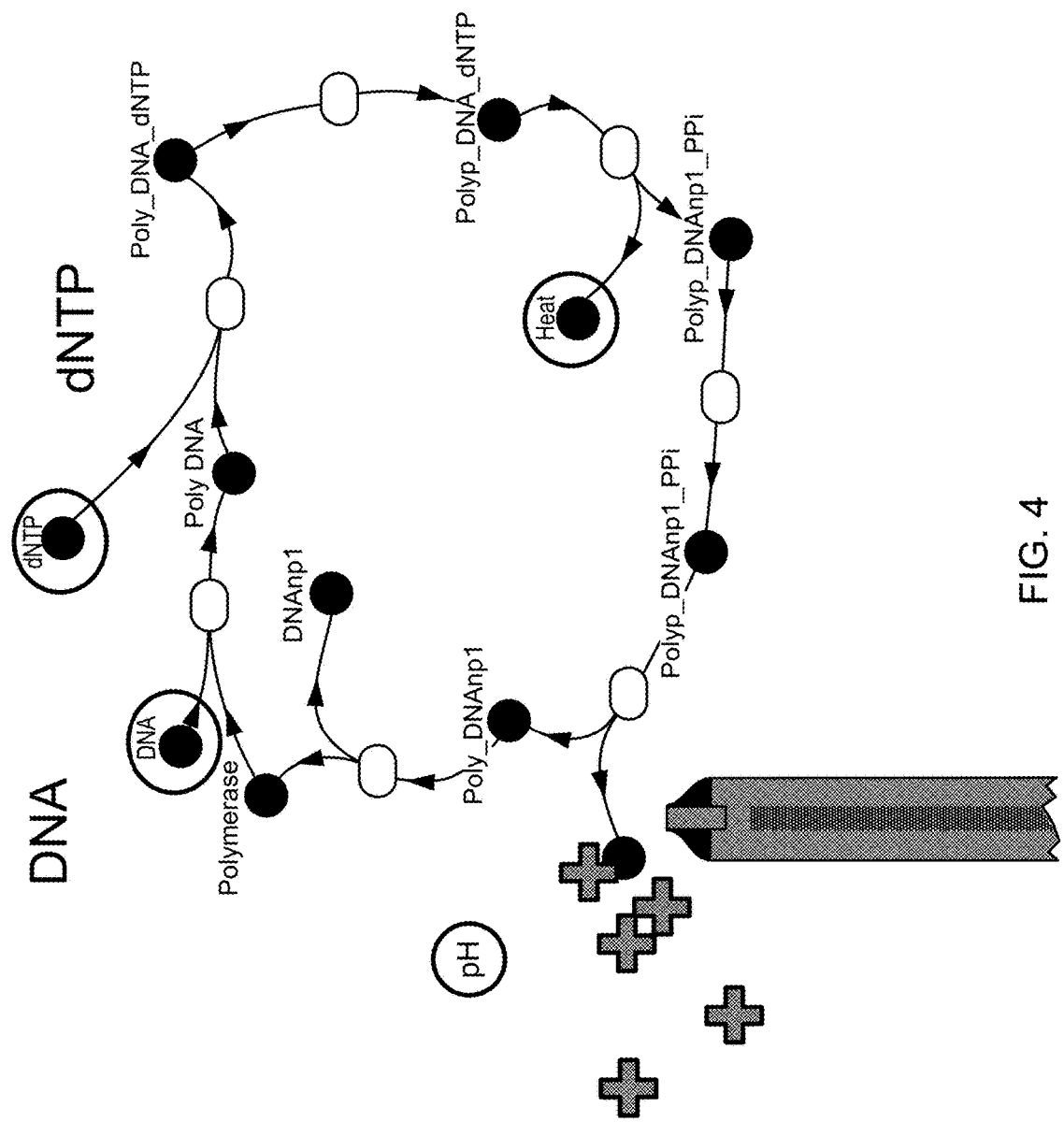

FIGS. 3 and 4 are schematic illustrations of the reaction involved in incorporating nucleotides into a growing DNA strand, showing the release of pyrophosphate and concomitant increase in pH. As described herein, the integrated sequencing platform may include an electronic sensing subsystem configured to electronically detect the change in pH or charge concentration or mobility to "electrically sequence" the DNA. In other embodiments, an electronic sensing subsystem can be configured to electronically detect the change in temperature resulting from this reaction to "electrically sequence" the DNA.

Figure 5A:
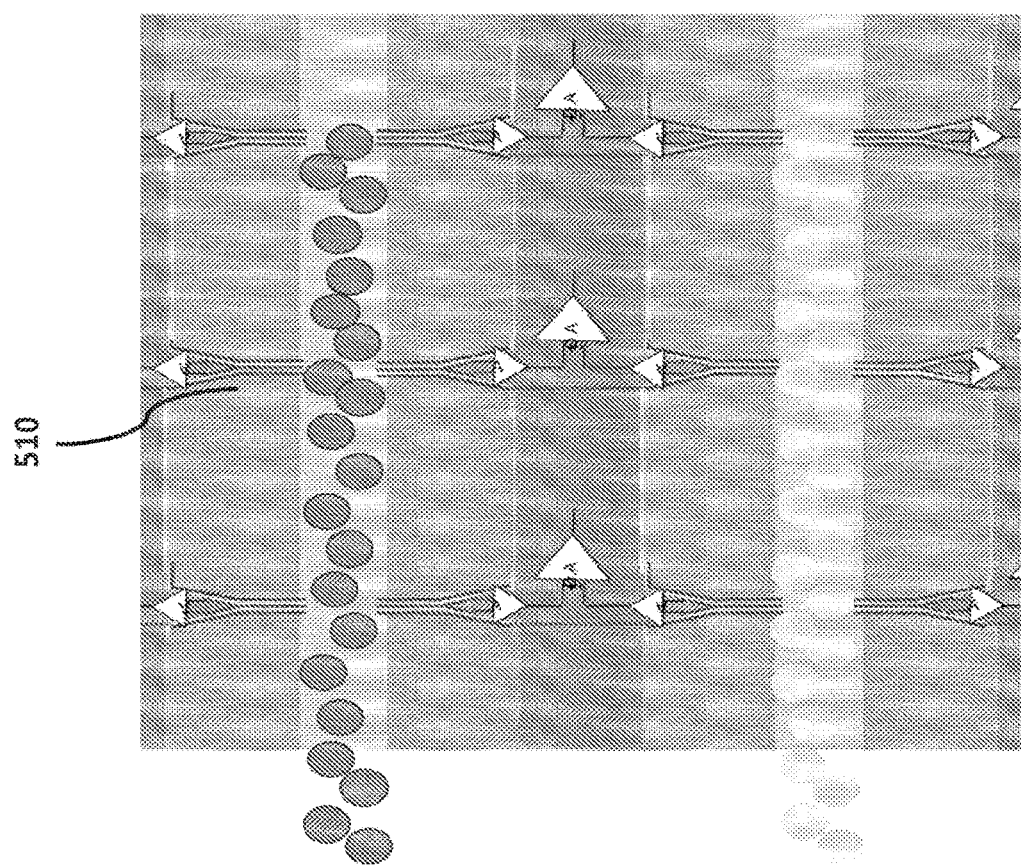
FIG. 5A shows a schematic illustration of a series of nanosensors in electrical communication with the microfluidic channels of the sequencing system.
Figure 5B:
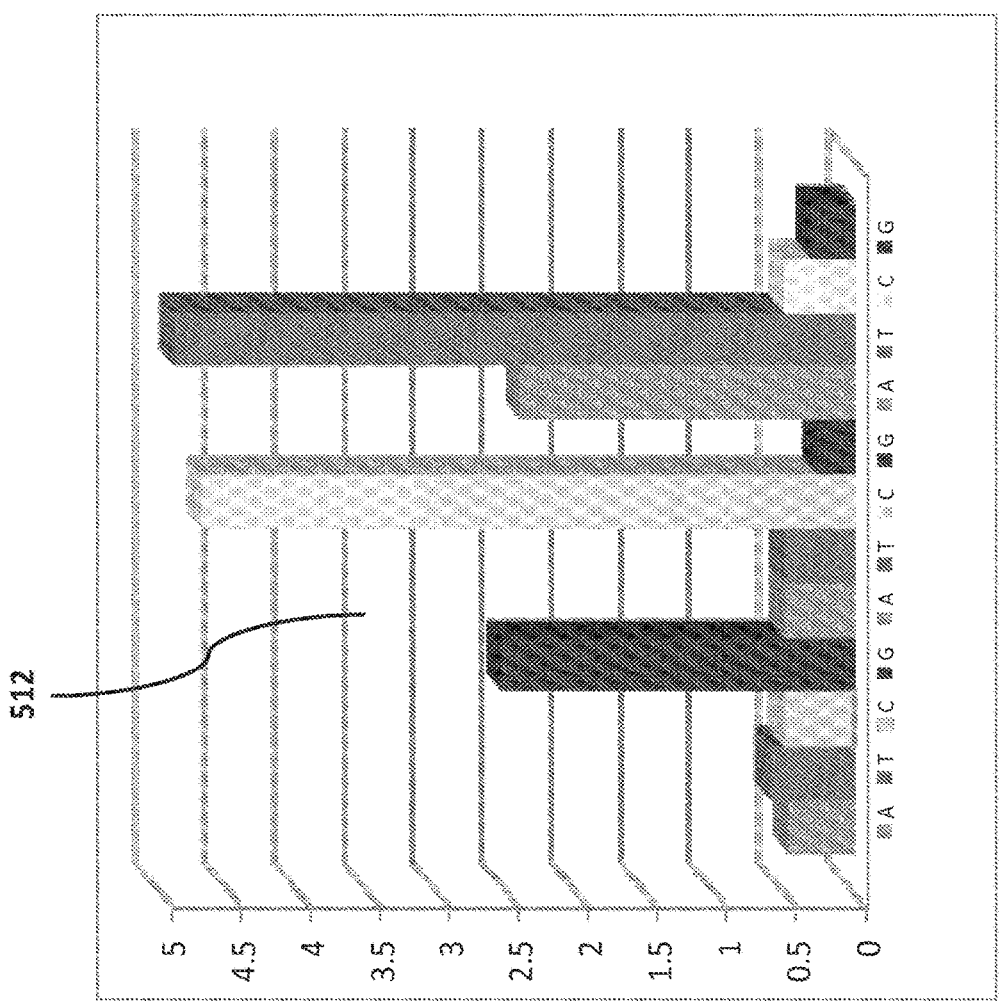
FIG. 5B depicts a graph showing output of a sequencing operation performed via a sequencing apparatus.

FIG. 5A depicts two sets of beads, one with clonal sets of DNA bound or attached thereto, and a set without clonal sets of DNA bound or attached thereto. This system permits utilization of the beads without clonal DNA bound or associated thereto to be used as a reference, removing offset, nucleotide and other reagent charge, temperature, fluidic flow and pressure, buffer concentration changes and other systematic variables to be removed. As shown in FIG. 5A, in schematic system 510, said removal of system variables may be done at least in hardware, using an analog subtraction. In other embodiments, the removal of systematic variables may be performed is in software and or external hardware. In yet other embodiments, a combination of local hardware and software and or external hardware may be utilized. FIG. 5B depicts resultant data, wherein most putative incorporation reactions result in signal levels indicative that a reaction did not occur, while some putative incorporation reactions result in signal levels indicative of a single incorporation event, and other putative incorporation reactions result in signal levels indicative of multiple incorporation events in a homopolymer region of the clonal DNA.

In a further embodiment, an electronic sensing subsystem may detect a change in conductivity, either in a bulk solution, across the surface of the sensor (either from moieties bound to the sensor or from moieties within the Debye length of the surface of the sensor), across the surface of a bead or particle (either from moieties bound to the bead or particle or from moieties within the Debye length of the surface of the bead or particle), or a combination thereof. In a yet further embodiment, an electronic sensing subsystem may detect a change in charge near or on the surface of the sensor, near or on the surface of a bead or particle. For example, the electronic sensing subsystem may detect charge changes within the Debye length of the surface of the sensor, or bead or particle, or of moieties bound to the surface or bead or particle.

Figure 6:
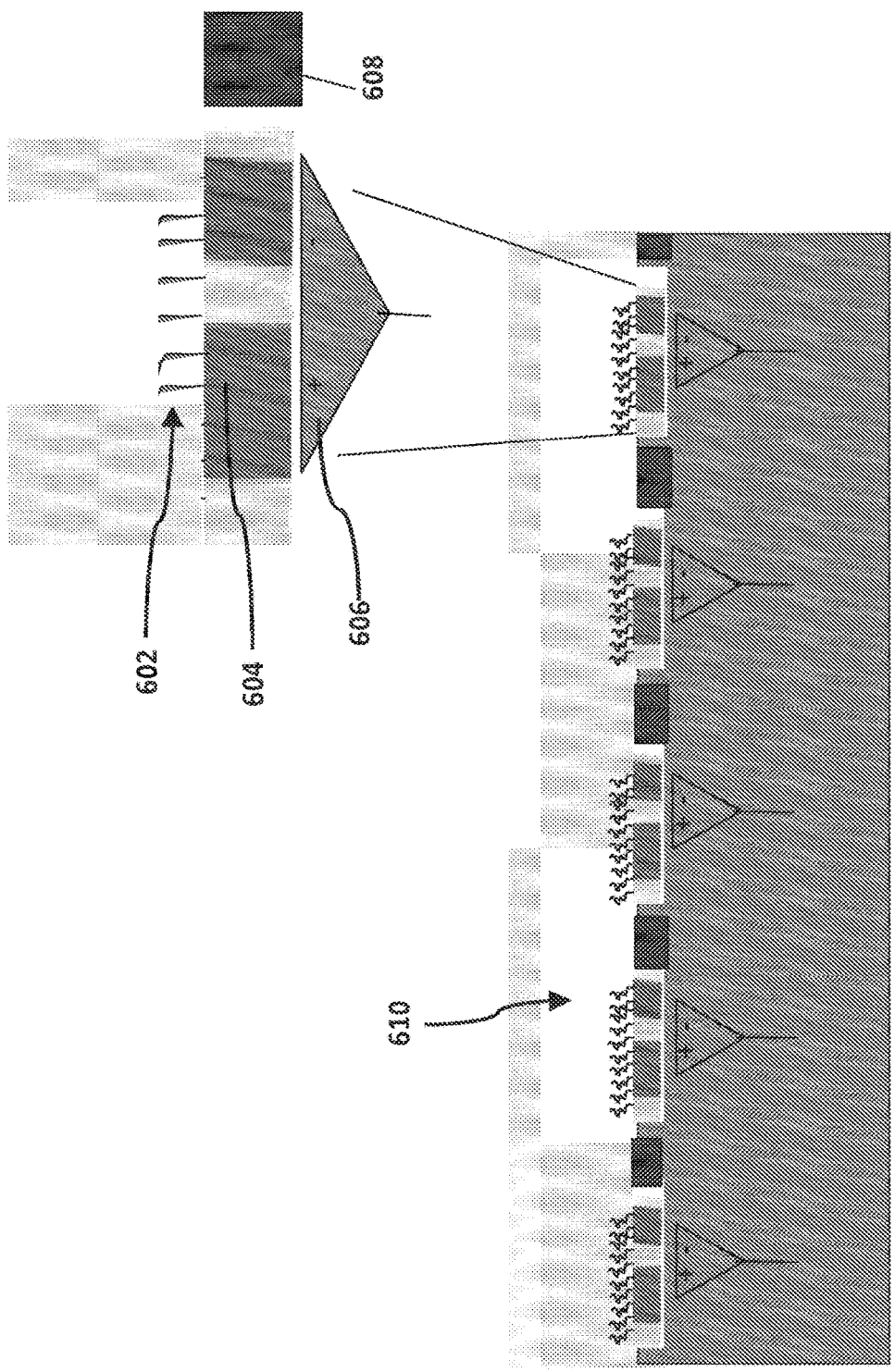
FIG. 6 shows an array of electronic sensors with a set of electrodes used for concentration or confinement of multiple charged moieties above the sensors.

FIG. 6 includes a schematic illustration of a nanosensor 604 and a series of nanosensors 610 associated with the microfluidic channels in electrical communication with the sequencing system. The nanosensors may have clonal DNA 602 bound or associated directly thereto, and may have electrodes or magnetic elements 608 associated with each nanosensor. In other embodiments the sensor may detect changes in the charge of the clonal DNA on the bead, changes in the counter ions associated with said clonal DNA, or byproducts which result from an incorporation. The nanosensor 604 may further include a signal amplifier 606 for on-chip signal amplification. The nanosensors 604 may further include any of the known insulator materials, such as $SiO_2$, $Al_2O^3$, SiN, and $TaO_2$ In certain embodiments, the nanosensors may comprise coaxial and/or parallel conductive layers, separated by an insulator layer. The conductive layers may be formed from any suitable material, such as gold, platinum, aluminum, carbon, or polysilicon.

Figure 7:
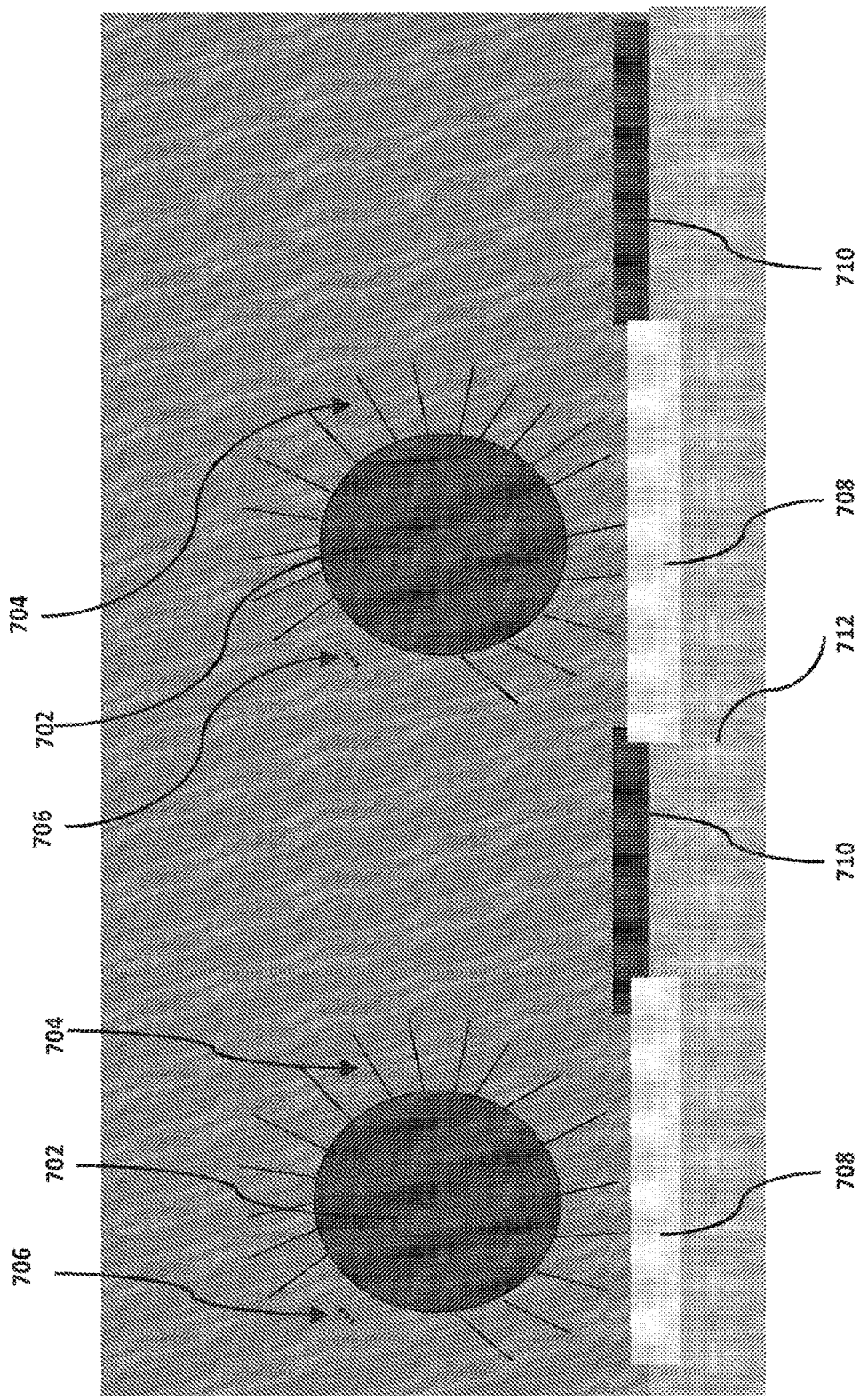
FIG. 7 shows magnetic or electric or electromagnetic retention of a clonal bead held in place for sequencing over a sensor.

The (magnetic) beads and DNA fragments may be conveyed into the sequencing system. As shown in FIG. 7, the sequencing system may include a series of nanosensors 708 in communication with the microfluidic channels defined within the sequencing system. The beads or particles 702 may be positioned over said sensors 708 by magnetic or electrode elements 710, which may form localized magnetic fields in some embodiments and may form localized electric fields in other embodiments, wherein both the sensors 708 and magnetic elements may be configured in association with a substrate 712. The beads or particles 702 may have clonal DNA 704 bound or associated thereto. Reagents, which may include nucleotides, primers, magnesium and polymerase 706 may then be provided to initiate a sequencing reaction. In other embodiments, when magnetic or electrode elements 710 are magnetic elements, they may be either permanent magnetic elements or electromagnetic elements.

In other aspects, the invention provides a method for sequencing a polynucleotide, using a magnetic array, forming an array of localized magnetic features as described herein. The method comprises contacting the magnetic array with a plurality of magnetic beads, the magnetic beads each having attached thereto a clonally amplified DNA segment, which may be single stranded, partially double stranded or double stranded. Whether single stranded, partially double stranded, or double stranded, the template DNA may be converted to single-stranded DNA by denaturation and a sequencing primer may be hybridized to the single-stranded DNA to prepare for sequencing.

After base-calling, the recorded sequence at each location on the array may be assembled. For example, by using a shot-gun sequencing method, wherein the identities of the fragments at each position of the array may be unknown, or a polynucleotide sequence may be assembled based upon a reference sequence (e.g., a wild-type sequence).

The clonal DNA sequences may each have a single-stranded region, acting as a template for nucleotide incorporation. The single stranded region may be at least 10 bases in length, or in some embodiments, may be at least 300 bases in length, or in other embodiments, at least 1 kb in length. The invention thereby provides for long, accurate, and cost effective reads. There may be more than one amplified populations of polynucleotides in one clonal population as defined herein, wherein the different amplified populations of polynucleotides may have different primers, so that separate sequencing reactions may be performed for each of the amplified populations within a single clonal population.

In another aspect, the magnetic array comprises an adjacent nanosensor for determining a change in pH of a microenvironment, the microenvironment including the environment in the vicinity of the bead held by the localized magnetic field. In this aspect, the microarray may be useful for electronic sequencing of DNA. Methods for sequencing by detecting a change in pH are generally described in U.S. Patent Publication No. 2008/0166727, which is hereby incorporated by reference in its entirety. Alternative methods of detecting incorporation of polynucleotides may be used, including thermal sequencing (e.g., as described in U.S. Patent Publication No. 2008/0166727), detection of charge concentration, mobility of charged species and byproducts, and known optical detection methods.

The magnetic array comprises a substrate having a plurality of localized magnetic features thereon to form the array, the localized magnetic fields being sufficient for trapping magnetic beads as described herein. The localized magnetic features may be formed from a permanent magnetic material (e.g., ferromagnetic), or may be nonpermanent and magnetized (and demagnetized) by an electric field.

In other embodiment, an electric field may be used to hold or retain a bead or particle in a location as will be described later herein.

Detector

A magnetic or paramagnetic bead or particle may be held in place over or proximate a sensing region by a magnetic array, forming an array of localized magnetic fields. Retained magnetic or paramagnetic beads may have monoclonal populations of DNA. Said beads may be sized such that there may be sufficient room for only one bead over each sensor, thus providing for a one to one correspondence between sensors and beads. Although there may be room for only one bead over each sensor, there can be an additional distance between beads when the beads may be aligned over the sensors, resulting in reduced cross-talk between sensors.

The magnetic sequencing array comprises a plurality of nanosensors, with at least one or two nanosensors in the vicinity (microenvironment) of each of the localized magnetic fields. The nanosensors have a high sensitivity for detecting slight changes in pH or charge concentration in each microenvironment (e.g., the vicinity of each localized magnetic field). For example, an array may comprise 1000 nanosensors or more, 2000 nanosensors or more, 4000 nanosensors or more, 10,000 nanosensors or more, 100,000 nanosensors or more, 1,000,000 nanosensors or more. 10,000,000 nanosensors or more or 100,000,000 nanosensors or more. The nanosensors may comprise measuring electrodes having two terminals, sufficient to determine an increase in the ionic ($H^+$) concentration, or an increase in the counter ions associated with DNA in the corresponding microenvironment or the occurrence of the polymerization reaction.

The nanosensors may include at least one pair of measuring electrodes having positive and negative terminals, sufficiently spaced apart (e.g., a spacing of between 20 and 30 nm) and constructed to detect a change in the ionic concentration of the corresponding microenvironment. In other embodiments the spacing between the electrodes can be 100 nm to 500 nm or 1000 nm to 5000 nm. More particularly, the nanosensor can detect a change in the impedance of the fluid within the microenvironment caused by a change in the ionic concentration of the corresponding microenvironment as a result on an incorporation event or a chemical reaction of the biological material on the beads and another material. In an alternative embodiment, the sensor can be a resistive semiconductor element as described in U.S. Provisional patent Application No. 61/389,590 entitled "Biosensor Devices, Systems and Methods Therefore." In yet another embodiment, the nanosensor may be a ChemFET or ISFET, as described in U.S. Pat. No. 7,695,907 "Gene detection field-effect device and method of analyzing gene polymorphism therewith", U.S. Pat. No. 7,948,015 entitled "Methods and Apparatus for Measuring Analytes Using Large Scale FET Arrays," U.S. Patent Application No. 2011/0171655 entitled "pH Measurement for Sequencing of DNA" and U.S. patent application Ser. No. 13/118,044 entitled "Nano-Sensor Array," each of which is hereby incorporated by reference in its entirety. Whenever the term nanosensor is utilized herein, it may be considered to be a set of electrodes as described above, or may be a resistive semiconductor element, or may be an ISFET or ChemFET or combination of the abovementioned sensors.

In some embodiments of the current invention, a combination of different sensing methods may be utilized, for example, a NanoNeedle and a NanoBridge, or an ISFET and a NanoNeedle. In some embodiments, the different sensors may sense different properties associated with the target moieties. For example, a NanoNeedle may detect the conductivity of moieties bound or associated with the target moieties, while a NanoBridge may detect charge bound or associated with the target moieties.

Figure 8B:
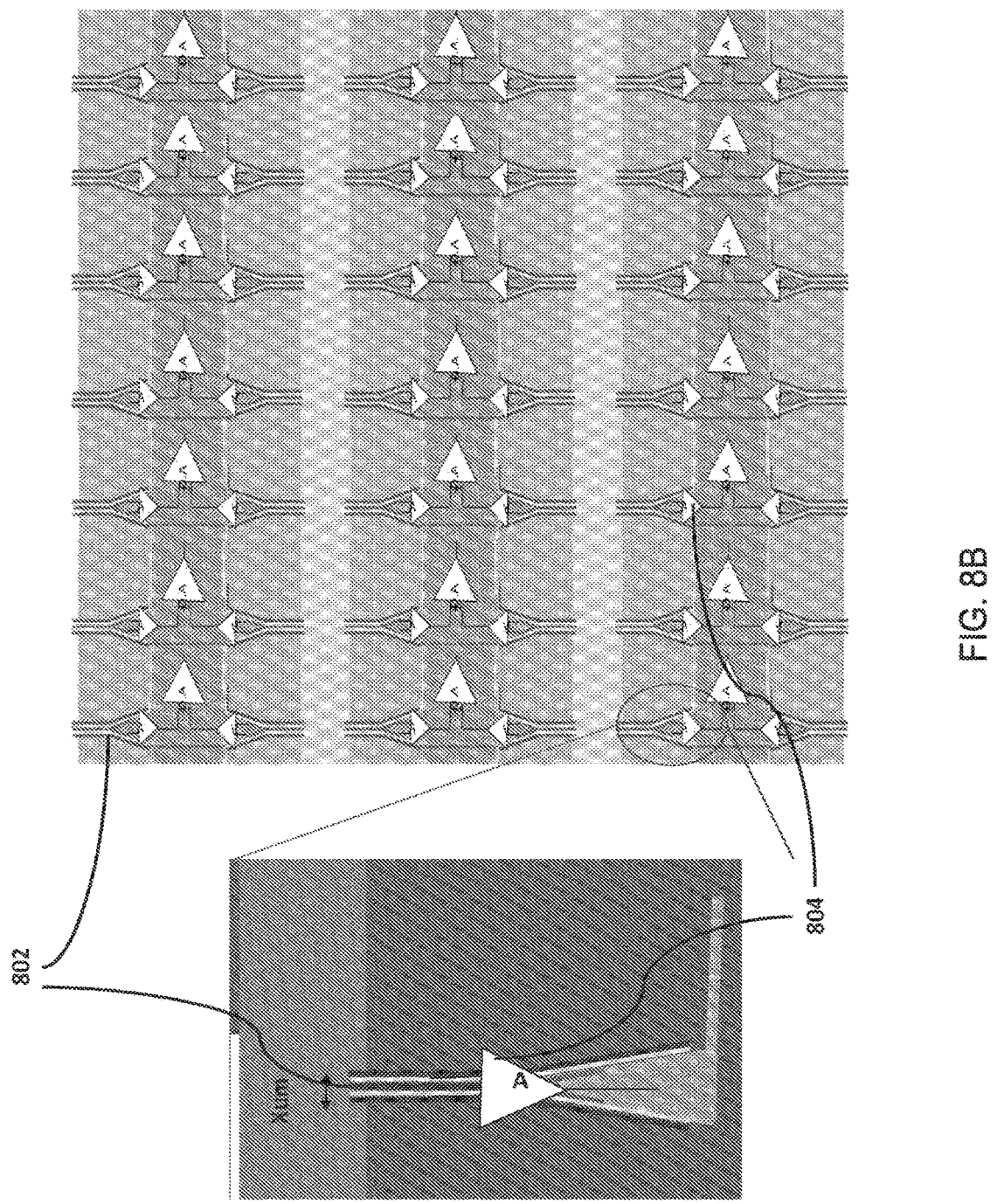
FIG. 8B shows a schematic illustration of a nanosensor, and a series of nanosensors in electrical communication with the microfluidic channels of the sequencing system.

FIG. 8A shows a photomicrograph of an array of nanosensors, and a zoomed in view of a single nanosensor 802. Impedance measurements may be used by such a nanosensor for detecting incorporated nucleotides. The impedance measurement detects the release of H+ ion pyrophospate or local change in charge resulting from the polymerization reaction. Generally, the frequency of operation may be selected for maximum change in the impedance over the course of the reaction relative to the impedance at the beginning of the reaction. For example, for some geometries, the frequency may be around 0.1 to 9 KHz. In alternative geometries, the frequency may be 10 KHz or greater. In some embodiments, the nanosensor may be implemented with a single pair of electrodes with or without a pH-sensitive material (e.g., redox sensitive material) to detect the H+ ion release or pH change of the reaction. The impedance measurement may be taken, as an example, by determining the current while sweeping from −A to +A volt or the reverse, with periodic sub-signals. A pulse wave with smaller amplitude than A, and a frequency of about 25 Hz or above, can be applied. A measurement of the current during a voltage sweep may indicate a change of pH in the solution proximate the nanosensor. FIG. 8B shows a schematic illustration of an array of said nanosensors 802, wherein an on chip amplifier 804 may be associated with each nanosensor.

Figure 9:
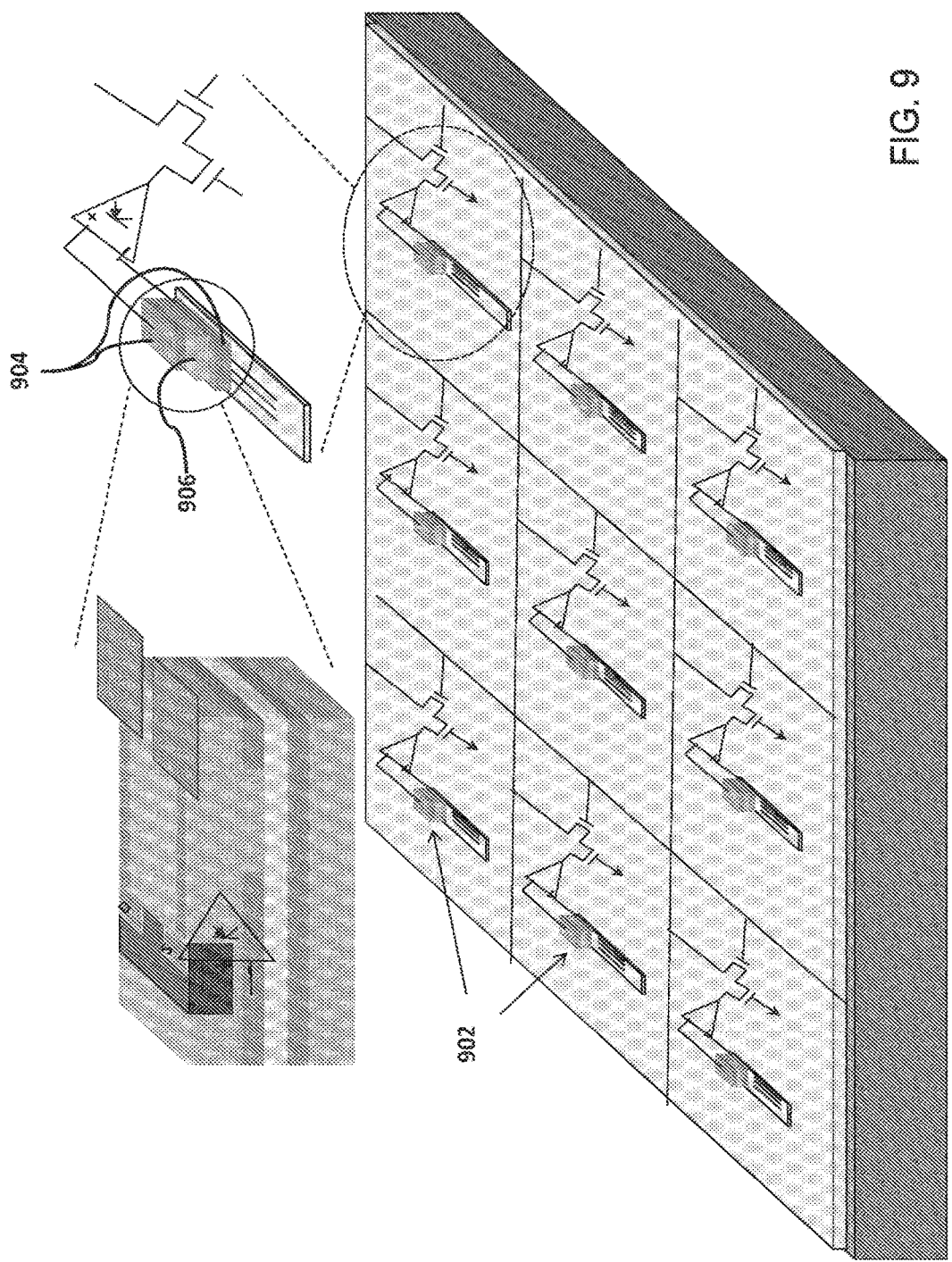
FIG. 9 shows a schematic illustration of an array of nanosensors within sequencing system. The on-chip amplification is optional.

FIG. 9 is a schematic illustration of an array of nanosensors 902 within the sequencing system. The nanosensor may comprise two electrodes 904, separated by a dielectric 906. Although shown in FIG. 9 as including an array of nanosensors, in other embodiments, the measurement can be done with a single electrode pair to detect the change of ionic construction or pH through impedance, charge, or current measurement.

The system may be calibrated for sequence analysis as follows. To reduce the common noise and signals from various environmental sources (e.g., thermal noise, mixing or fluidic noise, or the effect of nucleotide charges or other reagents), one or a plurality of beads(s) without DNA may be located in a similar environment as the DNA-coated beads. A differential measurement between the recorded signals from the two sensors (detecting the microenvironment of a DNA-coated-bead and bead-without-DNA or sensor without bead) dramatically reduces the noise, and results in an improved signal-to-noise ratio during detection. In some embodiments multiple local reference sensors can be combined to create a local average reference. In other embodiments magnetic features can be left off creating sensor positions with no beads. In some embodiments, the differential measurement may be done by comparing a neighboring DNA bead with no reaction in a cycle with the bead of interest for the same cycle. In other embodiments, the neighboring beads for differential measurement may be chosen from the region that receive the fluidic flow at substantially the same time, or beads without DNA or with DNA and without a reaction in that cycle. In other embodiments, averaging of the background signal over more than a single cycle may be used. Differential measurement of the sensor with another sensor which is shielded from contact or interaction with the fluid or target moieties.

In some embodiments, the integrated sequencing platform can produce a better signal to noise ratio, reduce the noise level from the proton (H+ ion) and OH− effect in sequencing detection and/or produce better isolation in virtual wells, than may be currently possible using known systems and methods. More particularly, in some embodiments, systems and methods can employ a buffer media configured to improve the performance, as stated above. The buffer can have different mobility and diffusion coefficients for H+ (proton) ions than the coefficients would be in water. The buffer can also have different changes in the coefficients for H+ and OH−. In some embodiments, a buffer media can be a material very similar to water, but with different mobility of H+, such as Deuterium oxide (D$_2$O or heavy water) or any common material having this functionality. The difference in mobility can slow the movement of H+ ion released in polymerization reaction. In another aspect, the buffer media can include material having different mobility for H+ ions and/or different materials e.g. DNA, nucleotides, primers or other moieties, and can be a gel-type material. A gel-type material would result in different mobility and diffusion for H+ ions released within the gel-type material, and facilitates easier detection, resulting to a better signal to noise ratio.

To calibrate the system for sequencing, and to ensure that the recorded signals from individual sensors may be appropriate and correct, a common sequence of nucleotides may be embedded in all template DNA strands being sequenced. This common sequence may be introduced during the amplification stage by design of the amplification primer. For example, a sequence of AATCGA may be incorporated, at the front end of all sequences, and may be utilized to calibrate the system, allowing known readouts of each of the nucleotide incorporations, also permitting calibration of a single base incorporation as opposed to a two or more base incorporation. Any combination of bases could be utilized, which could utilize all four of the bases, three of the bases, two of the bases, or a single base, and could include single base incorporations, two base incorporation, or any number of bases, up to and including eight base incorporations or more. Different primers may also be used as a means for encoding different samples.

Electrical Confinement and Retention

Figure 10:
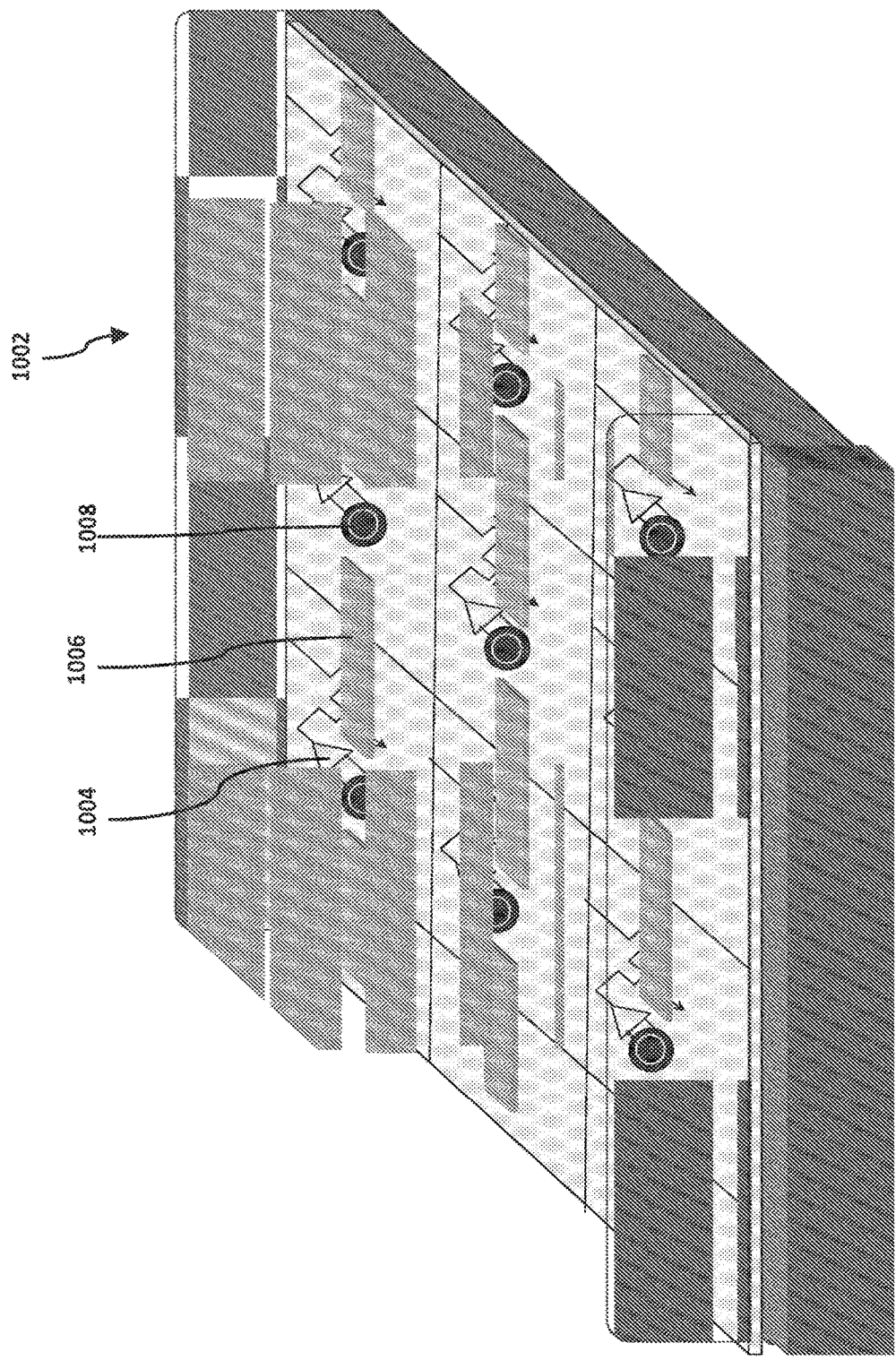
FIG. 10 depicts components of an exemplary sequencing chip.

In one embodiment, a magnetic array may comprise electrodes positioned to create an electric field around each of the localized magnetic fields, to thereby concentrate template DNA, polynucleotides and dNTPs around the localized magnetic fields (e.g., by electroosmostic, electrophoretic or dielectrophoresis force) to thereby enhance a polynucleotide amplification or polymerization reaction. The electric fields can create isolation between the regions of the array during the PCR or sequencing process, conduct DNA strands and/or nucleotides or other charged molecules toward the beads for clonal PCR, and/or conduct nucleotides toward the DNA-coated beads for sequencing. For example, electrodes may be positioned under the bead capture positions and in several positions surrounding the bead capture regions, such as in a circular or square arrangement, so as to enhance the polymerization reaction. The magnetic array for sequencing analysis may be created on a non-magnetic substrate as described. The read-out circuitry and on-chip amplifiers, which may be in pixelated structure, may be implemented above the substrate. Subsequently, the individual nanosensors may be fabricated, which may be in contact, directly or indirectly, with the microenvironment of the reaction as shown in FIG. 10. The magnetic bar array 1006 generates localized magnetic fields to associate the beads in the proximity of the sensors 1008. Optional associated amplifiers 1004 may be fabricated above or below the sensor layer as shown in FIG. 10 as part of an integrated device 1002. Microfluidic channels may be embedded in the structure. The chip may be operably connected with a data acquisition unit. In other embodiments, bead retention in bead capture features may occur utilizing a localized electrical field. In some embodiment the bead or particles can be nonmagnetic. Yet further embodiments may comprise electrodes positioned to create an electric field around each of the bead capture feature, sensors or other desired locations, to thereby concentrate template DNA, polynucleotides and dNTPs (e.g., by electroosmostic, electrophoretic or dielectrophoresis force) to thereby enhance a polynucleotide amplification or polymerization reaction. The electric fields can create isolation between the regions of the array during the PCR or sequencing process, conduct DNA strands and/or nucleotides or other charged molecules toward the beads for clonal PCR, and/or conduct nucleotides toward the DNA-coated beads for sequencing.

Figure 11:
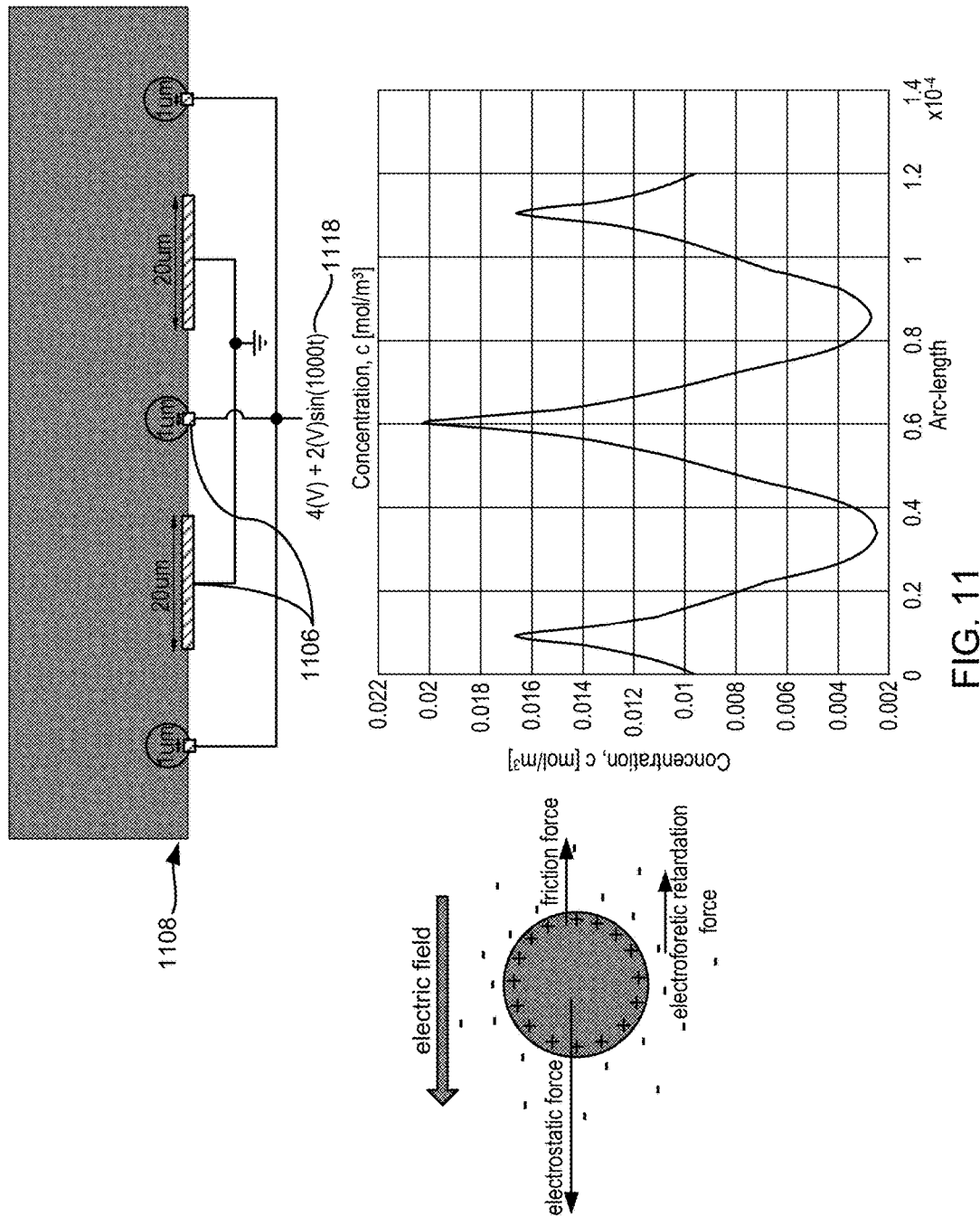
FIG. 11 shows the electric forces, a schematic embodiment and a concentration diagram from a simulation.

FIG. 11 schematically illustrates some of the forces which combine to localize the charged moieties with lower diffusion constants in a desired volume, including the electrophoretic flow which may result from an impressed electric field, frictional force, electrostatic force, and electrophoretic force. The schematic 1108 shows a voltage source 1118 generating a voltage impressed on the electrodes 1106, to generate a localized electric field.

The localized electric field may comprise AC and or DC components, and may utilize non-sinusoidal waveforms. Said non-sinusoidal waveforms may comprise triangle waves, square waves, or waves of any shape. Said non-sinusoidal waveforms may comprise a "dead spot" in, for example the peak of a sinusoidal waveform, in order to allow hybridization binding, enzymatic binding, other binding, and enzymatic activities to occur without the presence of a potentially interfering electric field. Other "dead spots" could be utilized for example, in a square wave, wherein the voltage could be raised to level of A volts for a period of time, and then be reduced to zero volts for a period of time. The voltage could then be raised to A volts again, followed by an amplitude of negative A volts. The "dead spot" need not be zero volts, but can be reduced sufficiently so that a desired interaction between different moieties influenced by the electric field may occur. The result of localized electric field on the charged molecule concentration 1109 shows the substantial gradient which results from the electric field and may provide substantial isolation.

Although described herein primarily for DNA applications, electrical confinement as described above may be utilized for other applications, such as applications or methods utilizing and or detecting antibodies or other proteins or chemical metabolites. In some embodiments, other reactions other than sequencing or amplification may be performed in a set of virtual wells. For practical usage in such an application, the moieties which need to be isolated need to be charged or associated with other charged moieties.

Figure 12:
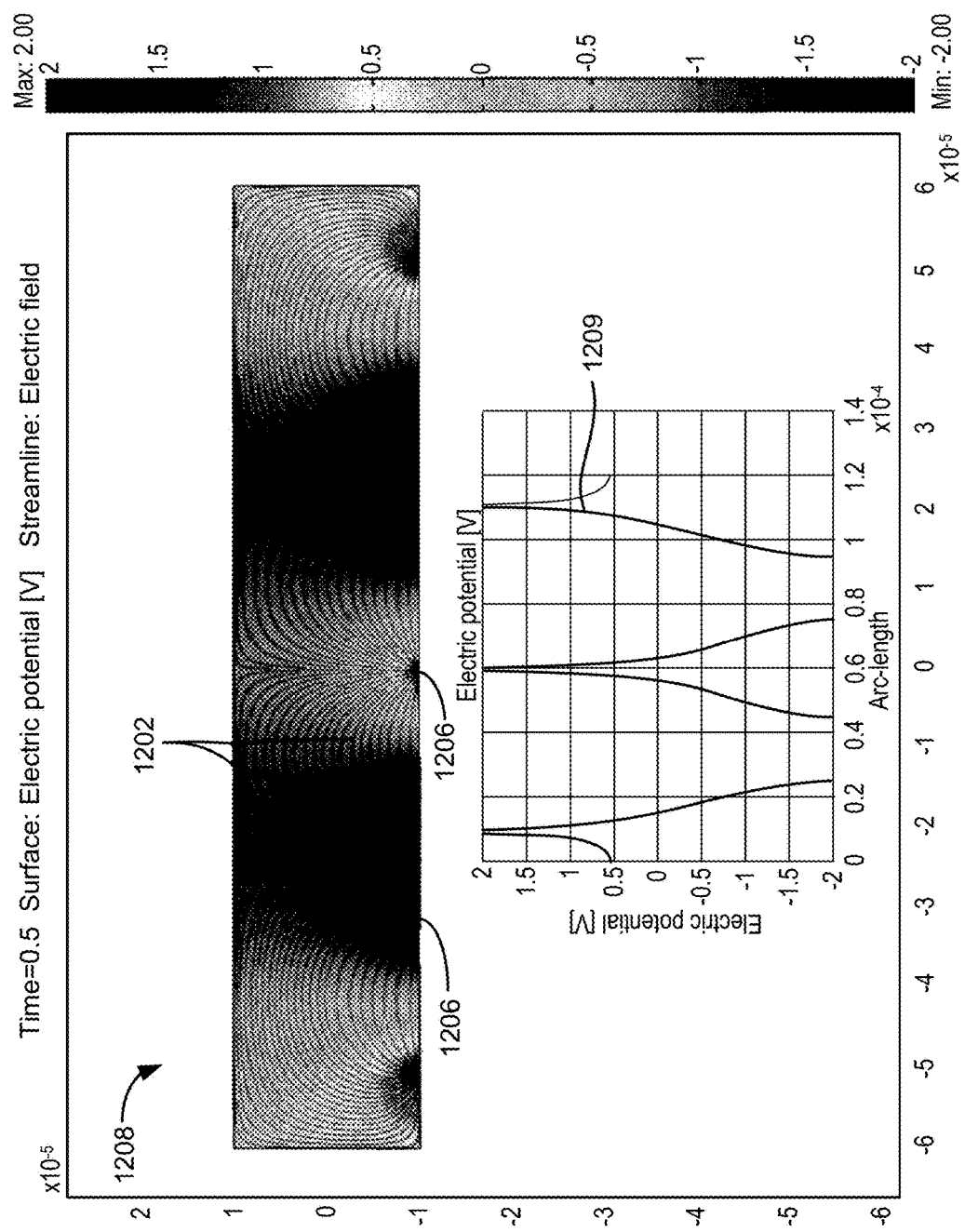
FIG. 12 shows the stream line electric field and the electric potential at a horizontal cross line above the electrodes from a simulation.

FIG. 12 shows electric potential at a horizontal cross line 1209 above the electrodes from a simulation 1208 which results from an electrical field being applied to the electrodes 1206. The stream line electric field 1202 and electrical potential due to the DC voltage which may be used for capturing charged moieties, including DNA amplicons near beads and preventing them from migrating toward the next bead. This simulation was performed for dNTP migration.

Amplification

In one embodiment of the current invention, the magnetic bar and electrode array provides for an emulsion-free method of clonally amplifying DNA fragments on magnetic beads, by isolating regions of the array by magnetic and or electric fields. Clonal amplification on beads has been generally described in U.S. Pat. No. 7,323,305, which is hereby incorporated by reference in its entirety. The invention may employ bridge amplification, which immobilizes the DNA strands on a surface of a bead, particle or sensor during amplification, thereby further preventing diffusion of DNA strands to other beads, particles, or sensors.

Figure 13:
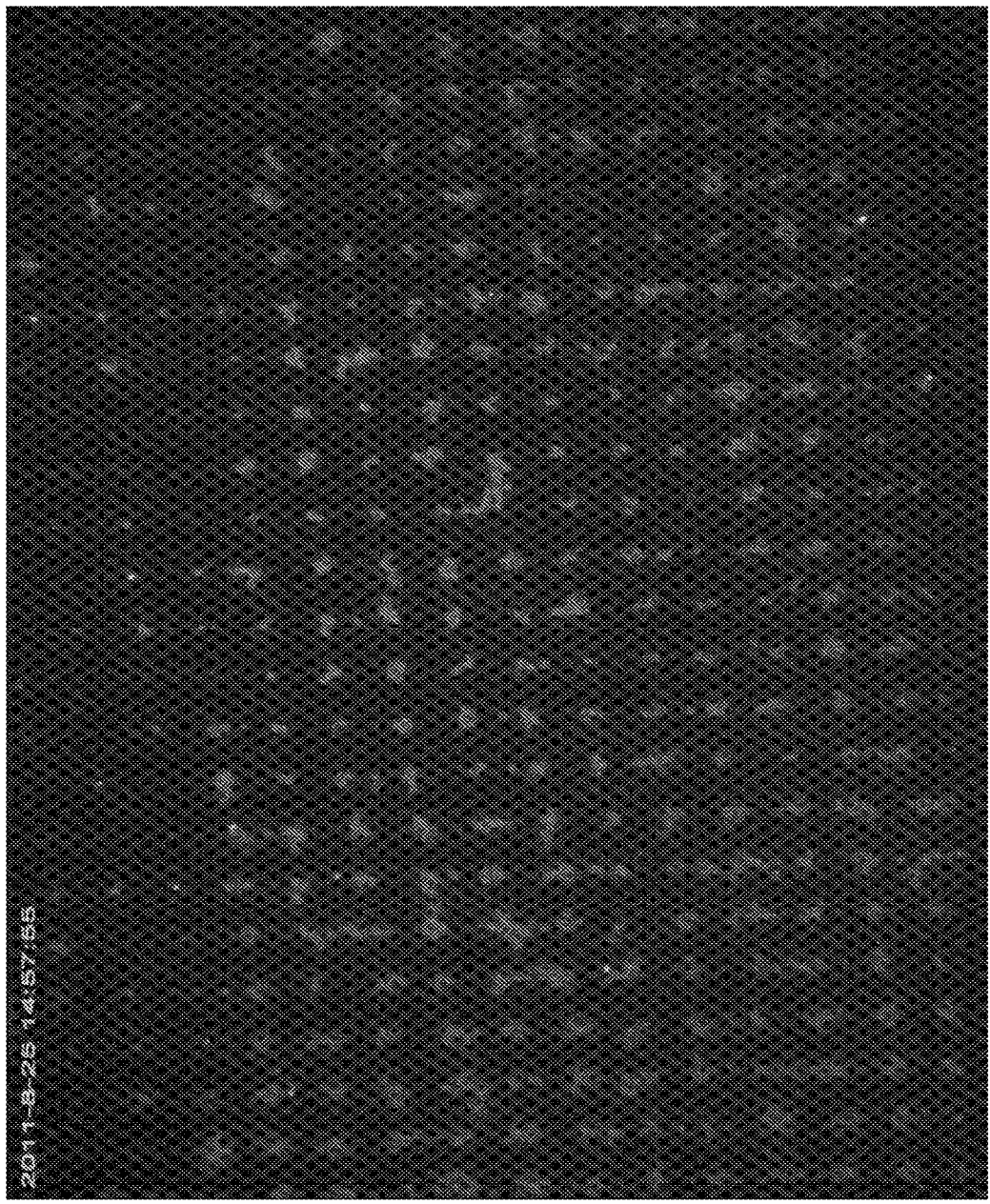
FIG. 13 shows a fluorescent micrograph of DNA on beads held by a magnetic array.

In an exemplary method for amplifying DNA fragments, magnetic beads may be injected onto the magnetic bar array having electrodes forming an electric field, DNA strand templates (double-stranded or single stranded) may be injected into the chamber to go over the beads in a concentration targeted for a desired DNA-strand per bead distribution, thereby allowing for clonal amplification. In certain embodiments, to insure that polyclonal regions are not generated, the concentration of input DNA needs to be low enough that most sensor regions have one or zero sample DNA molecules. dNTPs and DNA polymerase may then be injected into the chamber, and may be concentrated around the beads by virtue of an electric field as described. DNA primers for amplification may be provided at any step, such as when adding dNTPs and/or polymerase, or provided with the DNA templates. The DNA fragments immobilized on the beads may be amplified by PCR or isothermal amplification. Where double stranded DNA is the starting material, the first step of the amplification process creates single-stranded templates by "melting" the double stranded fragments, followed by primer annealing and extension steps, and repeated heating cooling cycles if PCR is utilized, or by a continuous controlled temperature for an isothermal amplification. FIG. 13 shows a fluorescent photomicrograph of clonal beads with double stranded DNA held in an array as described herein.

Figure 14:
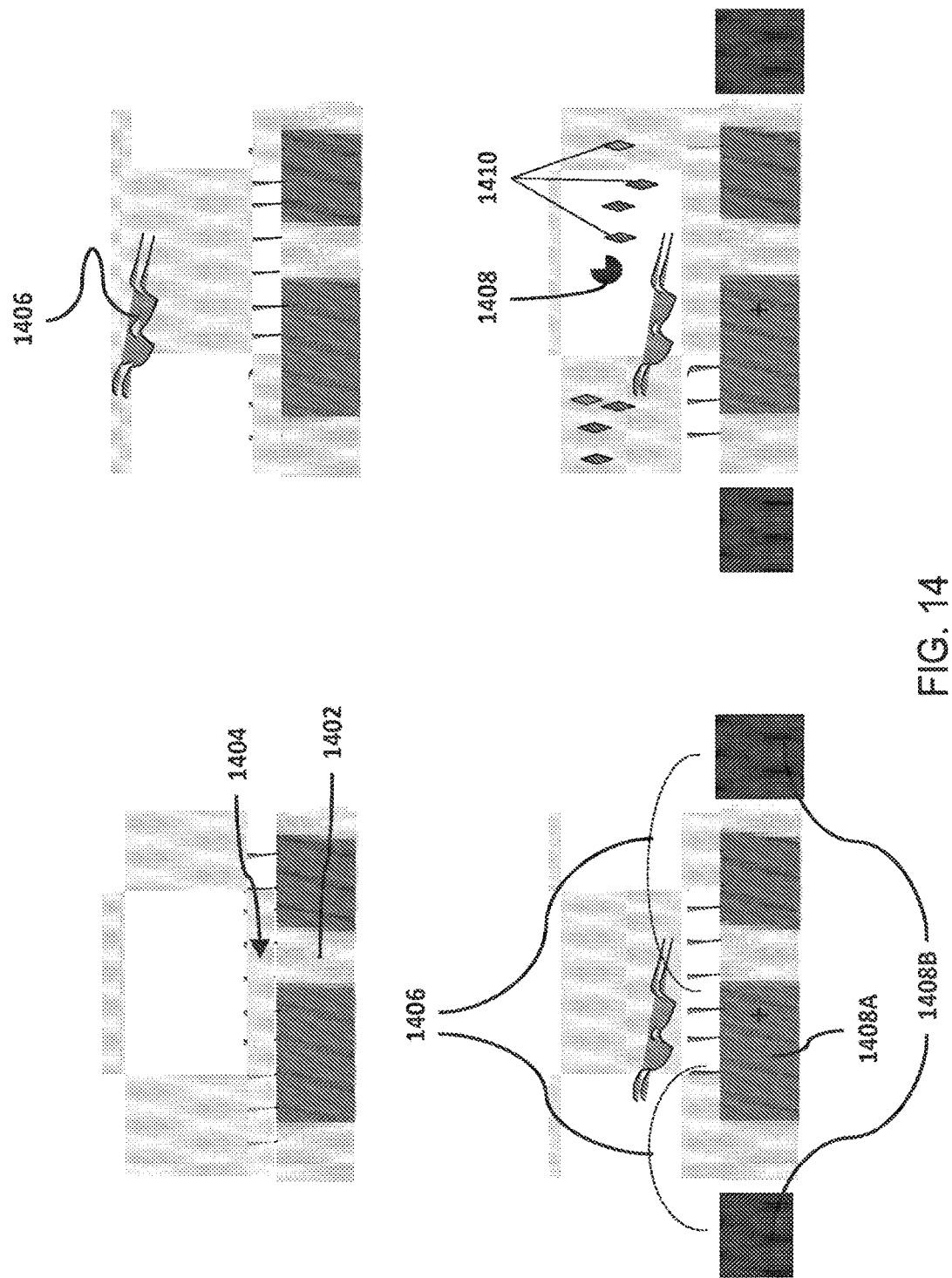
FIG. 14 shows a sensor with electrodes For creating electrophoretic concentration/confinement fields for attracting a sample molecule and confining the amplification reaction, and its use in an amplification reaction.

During the amplification process, dielectrophoresis forces may also aid in preventing cross contamination between different sensor regions undergoing amplification by retaining amplicons. In the embodiment illustrated in FIG. 15 the additional electrodes are shown as having the same voltage relative to voltage level of the sensors. In an alternative embodiment as shown in FIG. 14 electrodes on either side of a sensor may have voltages of opposite sign or the same sign with different values relative to each other.

In addition, a gel-type material can act as an isolating material in and or between different regions during amplification or sequencing with a magnetic array. The use of such a gel-type buffer media can result in minimal diffusion of DNA strands from one localized magnetic field to the neighbor (or adjacent) localized magnetic field, because the nucleotides (dNTPs), Mg2+ and other materials may be introduced during cyclic injection and can be transported through the gel-type or spongy media. The gel-type material can be any suitable material, such as agarose or acrylamide or other cross linking materials, in which cross linking may be initiated through physical or chemical triggers. One example of such triggers is a change of temperature (as a physical trigger), or the addition of a substance (to produce a chemical change to the material to make the media into the gel-type phase).

A "gel-like" or "spongy" material can also help confine the DNA strands in the volume near the beads, or help confine the DNA strands in or near the localized magnetic fields and/or reduce the diffusion of the polynucleotides. In such embodiments, the nucleotides and other materials may be allowed to diffuse more readily, but DNA strands, particularly sample or amplicon fragments may be impeded from freely diffusing.

In some embodiments, this method may reduce the diffusion of the DNA in the amplification portion of the system.

FIG. 14 depicts an alternative embodiment, wherein a clonal population may be generated in the area, or on individual sensors 1402 in a sensor array. The sensors may be NanoNeedles or NanoBridges or other sensors to detect the event of polymerization. In one embodiment, primers 1404 may be preferentially bound, associated with or attached to the surface of the sensors. Said primers 1404 may be preferentially attached as a result of a difference in materials, wherein the material of the sensor may be more advantageous for attachment then the areas between the sensors of the sensor array. In an alternative embodiment, a mask may be applied to areas between the sensors of the sensor array, and a surface modification may then be performed. Subsequently, the mask may be removed; leaving an area between the sensors of the sensor array wherein the surface modification has not been performed. The surface modification may include attachment of biotin, applying a layer of gold and various other methods as are known in the art.

Primers 1404 may then be preferentially applied to the areas on the surfaces of the sensors 1402 in the sensor array. In one embodiment, the primers could be attached as a result of a biotin streptavidin binding, wherein the biotin or streptavidin may be attached to the 5' end of the primers. In another embodiment, a thiol group may be attached to the 5' end of the primers, which can then bind to the gold layer previously applied above the sensor, forming an Au—S bond. If a PCR reaction is desired, the primers may be modified with DTPA such that two thiol gold bonds may be formed, preventing the dissolution which may otherwise occur from the 60 to 95 C temperatures routinely used in PCR. Target DNA 1406 may be concentrated in the area of the primers 1404 by electric fields 1406 generated by electrodes 1408A and 1408B. Primers, dNTPs 1410, and polymerase 1408 may be introduced and optionally concentrated by electric fields generated by electrodes 1408A and 1408B.

In some embodiments, amplification may be a solid phase amplification, wherein one primer may be on the surface of the bead, and a second primer may be in solution. In other embodiments, the amplification may be solid phase wherein all primers are on the bead, or the amplification may be performed whereby both primers are present in solution, and one primer or both primers may be also present on the bead. In a further embodiment, the amplification may be performed whereby one primer is present in solution, and one primer or both primers are also present on the bead.

Figure 15:
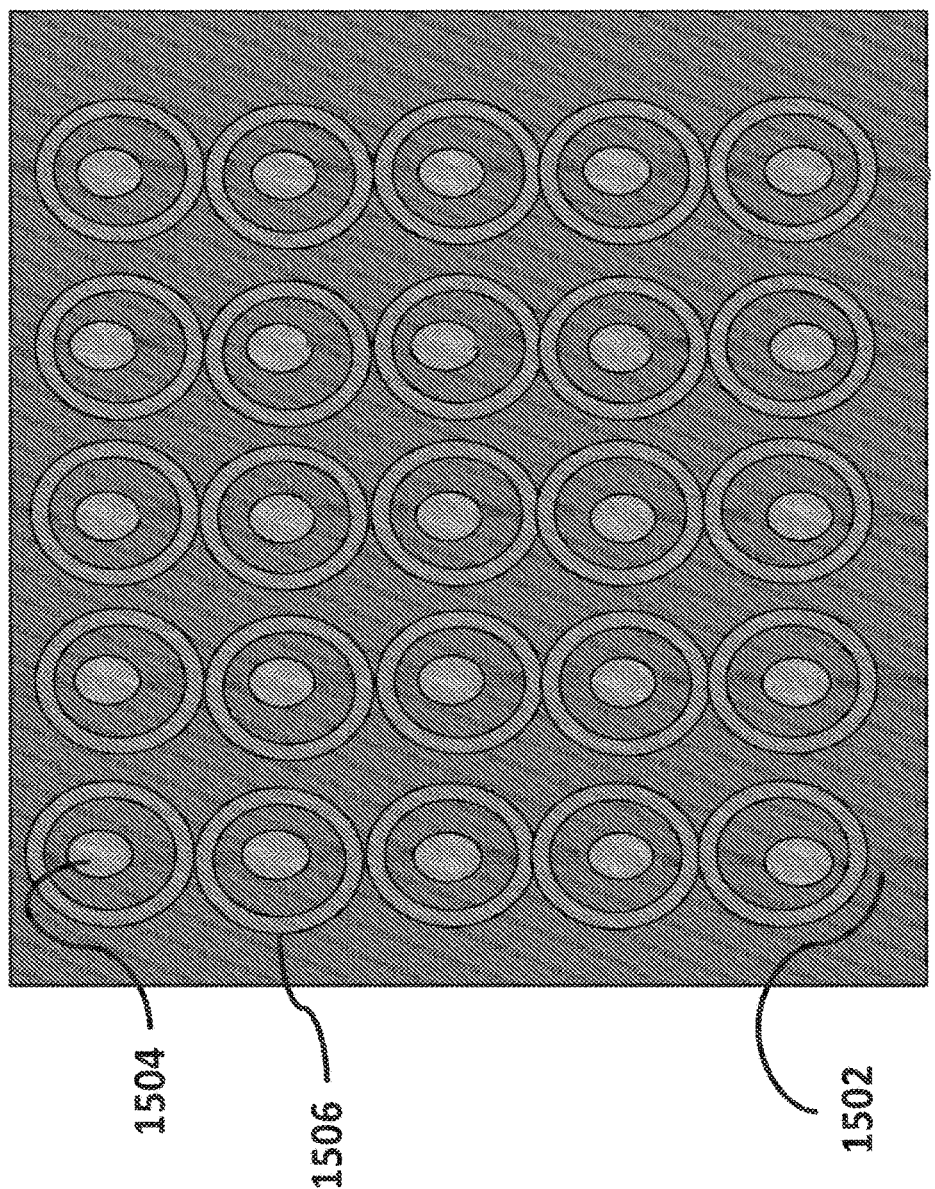
FIG. 15 shows an array of electrical confinement electrodes and sensors in a one to one correspondence.

The electrode configuration may take various different forms, including a substantially planar electrode on one or both major planes of the flow cell, or there may be an electrode on the surface opposite the beads, and a set of smaller electrodes associated with each sensor, or bead capture region FIG. 15 schematically illustrates one embodiment, wherein a set of sensors 1502 may be located associated with electrode structures 1504 and 1506, wherein the electrode structure may have an electrode 1504 located in immediate proximity to the bead capture feature, and a larger electrode structure 1506 may encircle the bead capture feature and the smaller electrode 1504. The bead capture feature may be in proximity to the sensor active area when the embodiment used for sequencing or detection. The larger electrode is illustrated as a circle, but it may me a square, a rectangle, an oval or other shape, and need not completely encircle the smaller electrode 1504.

The substantially planar structure may include depressions or wells for better alignment or field focusing, or pedestals for better fluid flow characteristics.

Prior to amplification the beads may be associated, in some embodiments, with a single DNA fragment in order to create monoclonal beads. Typically the DNA concentration may be determined and then the DNA may be introduced to beads in a dilute form so that on average less than 1 fragment may bind to each bead. Many beads have zero DNA fragments, fewer have a single fragment and a small number have 2 or more fragments. The steps needed for quantitation often require a separate instrument and separate processing.

Frequently quantitation may be done utilizing real time PCR, or determination of the absorption at 260 nm.

If three or more electrodes are utilized, different voltages may be utilized for any set of the electrodes.

A polymer may be utilized in conjunction with an AC field which has one phase with a higher voltage and shorter duration in order to provide directed mobility of the target molecules.

In one embodiment the sample could be made very dilute and/or a small volume of sample reagent may be utilized and loaded onto beads. DNA would bind to some of the beads and then be amplified in the virtual wells creating beads with DNA. The sequencing primer could be made shorter than the complement ligated to the sample DNA. Since the sequence is known, the correct dNTPs could be added and detected. In one embodiment multiple dNPTs could be simultaneously added. For example, if all dNTPs are added the polymerase would extend to the end of the fragment generating a large signal. Said large signal could be generated as a part of the amplification process. This would allow the detection and counting of the number of beads that have DNA even if the beads had minimal amplification. Knowing how many beads have signal would allow calculation of the proper dilution to generate the ideal number of monoclonal beads. The signal may be electrical, optical or any other type of the detection signal known in then art.

In some embodiments, electric confinement of amplicons, polymerase or other moieties may be utilized with a device which does not have any physical well structure. In other embodiments, the device may be a substantially planar surface, wherein depressions or protrusions exist. In yet other embodiments, the device may have well structures.

Electrical Concentration

As illustrated in FIGS. 6 and 12, the sensor array may be provided with an additional array of electrodes, which may be utilized to perform dielectrophoretic concentration. Dielectrophoretic concentration may be initially performed to attract sample DNA 1206 dNTPs 1210, primers, and polymerase 1208, to each sensor or amplification region, permitting lower concentrations of each said moiety to be utilized. Amplification can then commence in the region of each sensor where a sample DNA molecule may be located. The electric field generated virtual well can prevent amplicons from leaving one virtual well and traveling to another virtual well, generating cross contamination. In a similar manner, the fields used to localize the amplicons may also concentrate the amplicons, primers, and polymerase to the region of the sensor or amplification region.

In another embodiment the sample may be concentrated in the amplification region using the existing electrodes of the emulsion free nano-well. In one embodiment electrodes may be established on a single plane. In another embodiment electrodes may be added to a second plane parallel to the plane of the virtual wells. In other embodiments mixtures of AC and or DC voltage inputs are anticipated.

In another embodiment dielectrophoresis could be used to concentrate DNA. During or after concentration the electrical current could be measured to determine the DNA concentration. In another embodiment the concentrated DNA could be quantitated by the use of intercalating dyes as described below.

The isolating field electrodes may also be utilized for concentration. In some embodiments the same electrodes and field may be utilized. In other embodiments, fewer or more electrodes may be utilized to generate the concentration field, relative to those used for generating an isolating field.

Concentration may be utilized to maximize utilization of sample, for example, directing or pulling DNA sample to virtual wells for subsequent amplification. Concentration may also be utilized to direct or pull polymerase to a virtual well for amplification, or to a clonal set of DNA which may be associated with a bead or sensor, and said polymerase may be utilized in a sequencing reaction. In a similar manner, other moieties such as dNTPs, primers, other enzymes, and other biological or other charged moieties may be concentrated for use in a reaction, or use in a subsequent reaction.

Significant amplification of sample DNA is often performed to ensure sufficient DNA sample is available at a high enough concentration for the desired protocol. This amplification can introduce bias and may be an additional cost in time and resources. The ability to reduce or eliminate the need to amplify the sample may be desirable. In one embodiment the beads to be loaded may be enclosed in a packed bed and sample may be pumped across it. In some embodiments the sample can be pumped through the area with the beads multiple times to provide additional opportunities for the sample to bind. The high surface area to volume should allow minimal sample to be used. The beads can subsequently be moved into a flow cell whereby they may be held in place by a magnetic array, and local colonies may be created on the beads by PCR or isothermal amplification.

Multiple Samples

Since many projects do not require the full use of the chip it may be desirable to load multiple samples in a single chip. In one embodiment, samples may be directed into separate zones separated by walls on the chip using valves integrated into the chip assembly. Such valves could be polydimethylsiloxane PDMS valves integrated into the fluidic path. In another embodiment, samples may be directed into separate zones separated by walls on the chip using valves separated from the chip assembly with multiple inputs on chip assembly. In another embodiment there may be separate zones with separate inputs and outputs. In another embodiment samples may be directed into separate zones on a chip or flow cell using a local electric field. A positive field may be applied to attract DNA or DNA-coated beads to desired regions, while a negative field may be applied to repel DNA or DNA-coated beads from undesired regions. In another embodiment samples may be directed into separate zones using electromagnets to separate magnetic or paramagnetic beads. In another embodiment samples can be delivered into individual lanes using self sealing ports. Self seating ports can include rubber septa and needles.

In another embodiment samples can be injected at different time points and new beads can be distinguished due to signal from previously empty bead locations.

In some embodiments of the current invention, as a part of the sample preparation process, "barcodes" may be associated with each sample. In this process, short oligos are added to primers, wherein each different sample utilizes a different oligo in addition to primer. The primers and barcodes are ligated to each sample as part of the library generation process. Thus during the amplification process associated with generating each colony, the primer and the short oligo are also amplified. As the association of the barcode is done as part of the library preparation process, it is possible to utilize more than one library, and thus more than one sample, in generating the clonal populations, permitting determination of which bead and colony originates with which sample, by sequencing the short oligo along with the sample sequence.

Sample separation methods can be used in conjunction with sample identifiers. For example a chip could have 4 separate channels and use 4 different barcodes to allow the simultaneous running of 16 different samples. This permits the use of shorter barcodes while still providing unambiguous sample identification.

Figure 16B:
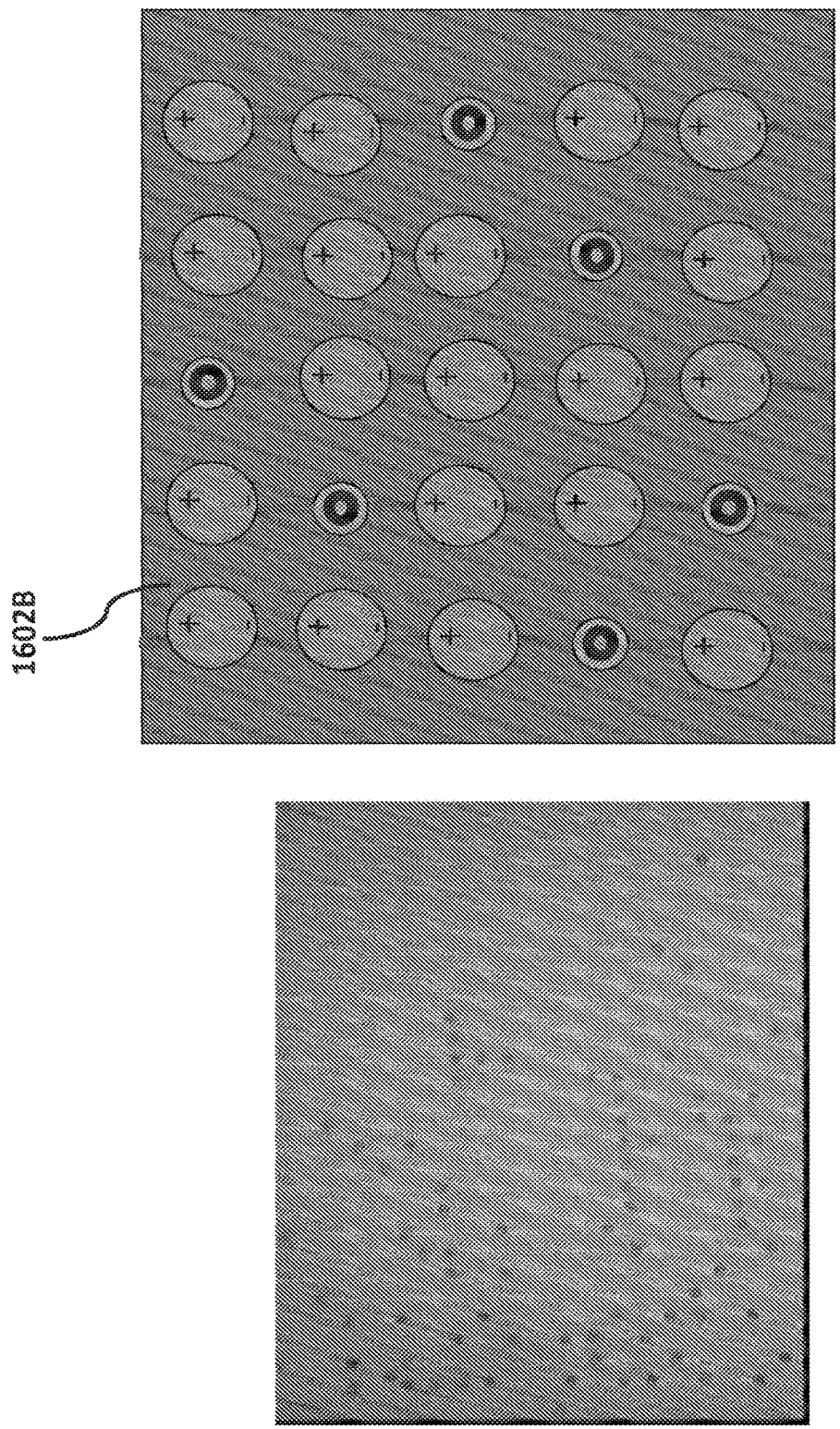
FIG. 16B shows the set of beads captured wherein each captured DNA covered bead is held in place over a sensor.
Figure 16C:
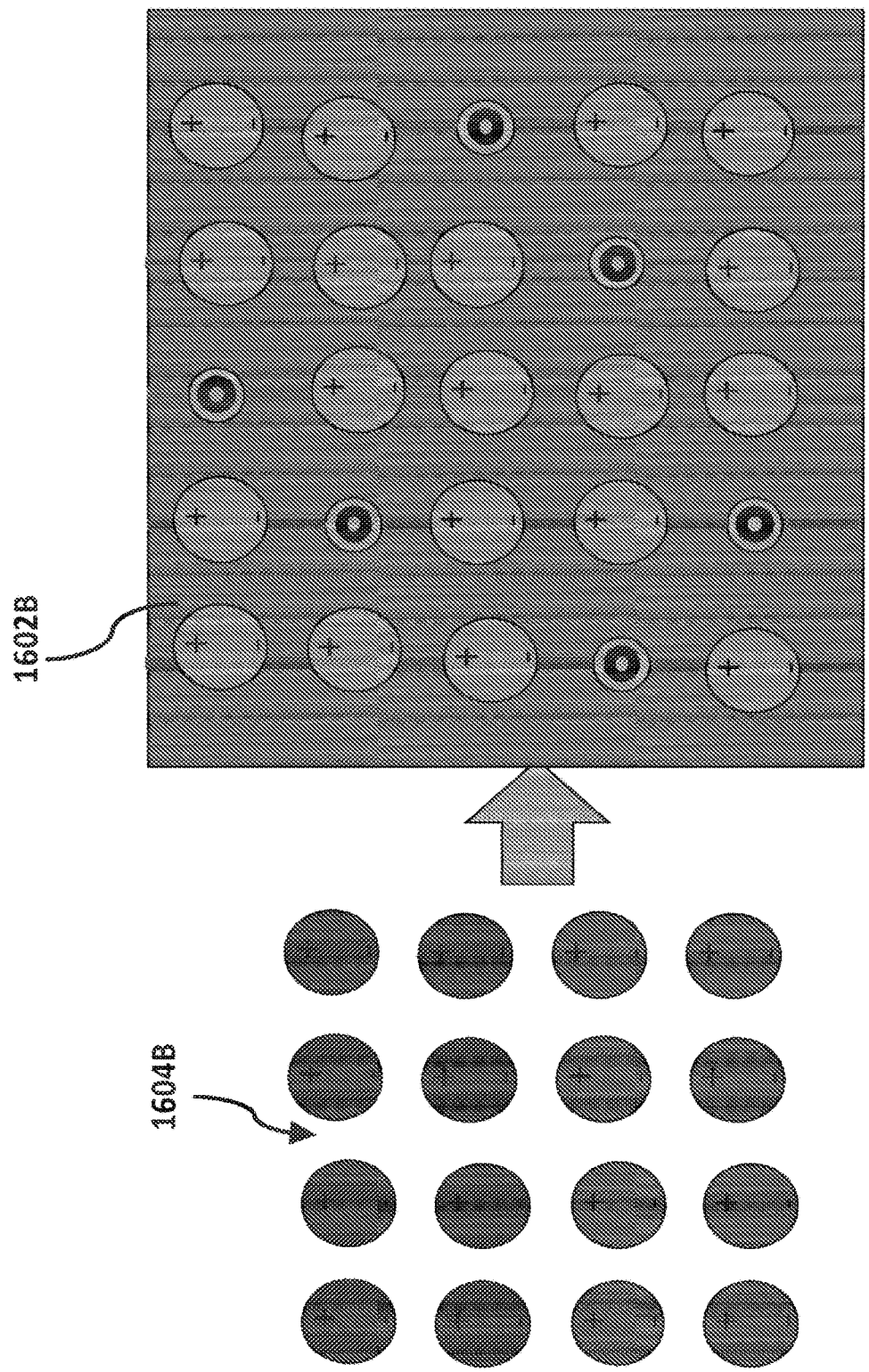
FIG. 16C shows a second set of beads and a sensor and magnetic confinement array which are partially populated with beads.
Figure 16D:
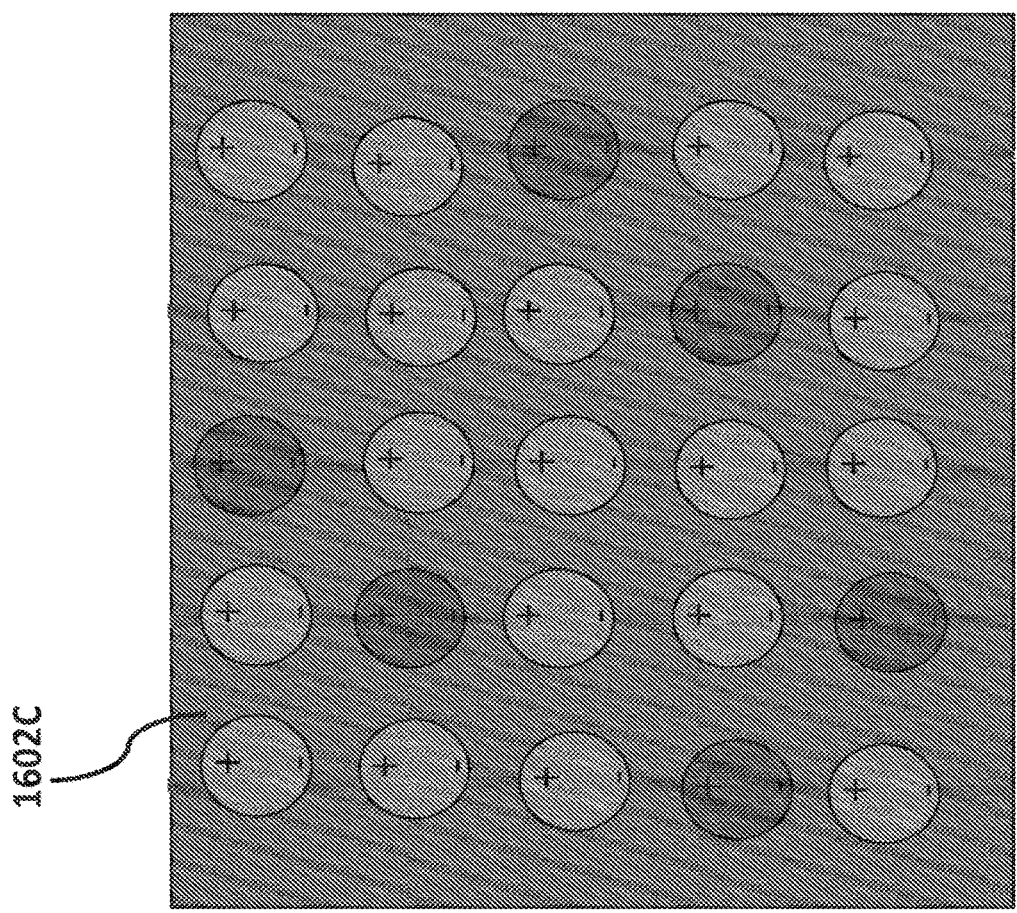
FIG. 16D shows two sets of beads captured by a sensor and the magnetic confinement array of FIG. 16C.

In an alternative embodiment as shown in FIGS. 16 A-D, samples may be brought into a system which may have a magnetic array and associated sensor array. Alternatively the system may have a combined amplification and detection array, wherein each element of the array may have a sensor and a set of electrodes configured to create a virtual well. A DNA sample set 1604A which is configured to occupy only a portion of said array 1602A, may be introduced to said array 1602A, resulting in a portion of the available areas to have an associate sample. Such samples may then be detected by the sensors associated with each virtual well, resulting in an array 1602B as shown in FIG. 16B, or may be amplified and then detected. FIG. 16B also shows a photomicrograph of a partially filled magnetic array. FIG. 16C shows a further sample set 1604B, which may then be introduced to the magnetic and sensor array 1602B, resulting in a more completely filled array 1602C as shown in FIG. 16D.

Combined Electrical Confinement and Sequencing

Figure 17:
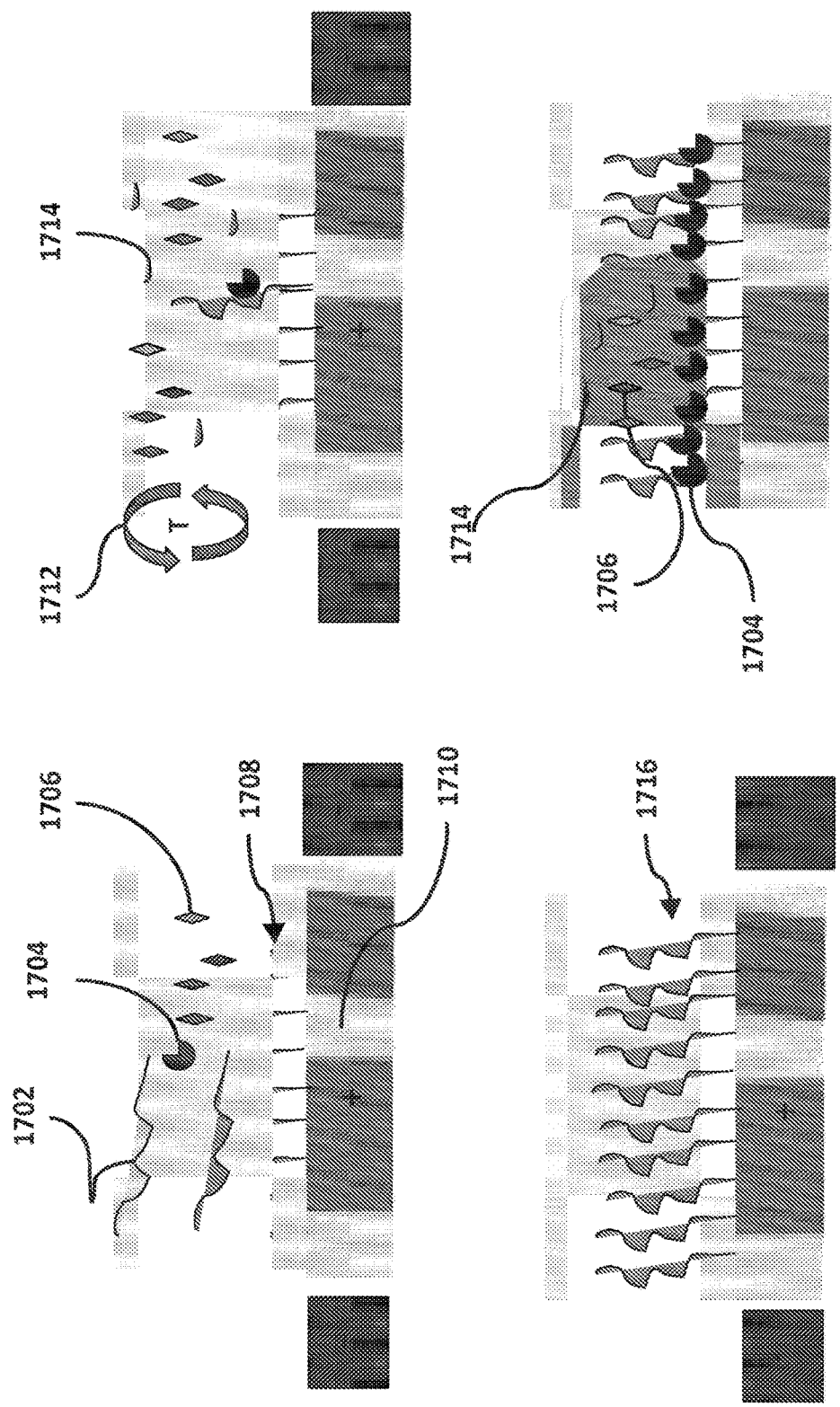
FIG. 17 shows a sensor with electrodes for creating electrophoretic concentration/confinement fields used for amplification and sequencing reactions

FIG. 17 illustrates the use of the amplified regions above the sensors in the array of sensors which may be used in a sequencing reaction. DNA sample 1702 may be brought into the array system 1710, wherein the array may be configured either with pre-localized beads, or with primers 1708 which may be attached, bound or associated with sensor regions 1710. Polymerase 1704, dNTPs 1706 and additional primers may be simultaneously, previously, or subsequently introduced to the array. After the amplification reaction 1712 has been completed, the volume above the sensor array may be washed, removing amplicons, polymerases, and dNTPs, resulting in locally bound associated or attached clonal sets being associate with array positions. Polymerase 1718, primers 1714, and individual dNTPs 1706 may then be flowed into the volume above the sensor array, permitting binding, incorporation, and detection of the incorporation events, resulting in the determination of the sequence of the different amplified sample DNA molecules. Polymerase 1718 used for the sequencing reaction, may be the same type of polymerase 1704 as used for the amplification reaction, or may be a different type of polymerase.

Separation of Clonal Beads

Figure 19:
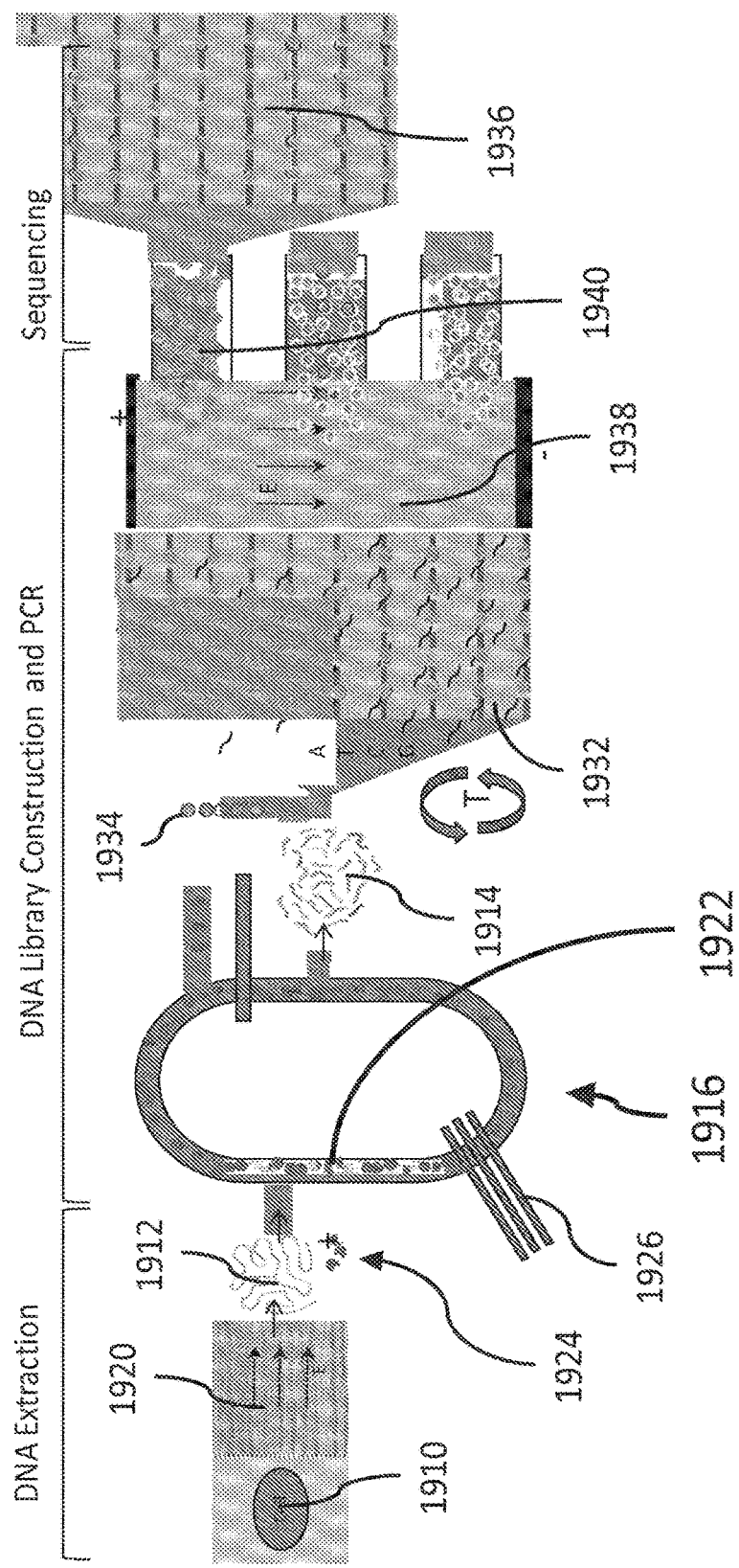
FIG. 19 is a schematic illustration of an integrated platform for extracting, amplifying and sequencing polynucleotides according to an embodiment.

Part of FIG. 19 shows a schematic illustration of a system which may separate magnetic or paramagnetic beads with clonal DNA from magnetic or paramagnetic beads which have not had amplification product associated thereto and/or have incomplete amplification and/or short clonal. The magnetic beads 1934 may then be separated such that magnetic or paramagnetic beads 1934 having a clonally amplified DNA segment bound thereto may be conveyed into the sequencing system, and magnetic or paramagnetic beads 1934 that are largely devoid of amplified DNA may be conveyed to a waste chamber and/or retained within the PCR and enrichment system. The separation or "enrichment" may be produced by applying an electric field across a portion of the PCR and enrichment system to induce electrophoretic flow. Thus, the magnetic or paramagnetic beads 1934 having amplified DNA, which is highly charged, may be efficiently separated from those magnetic paramagnetic beads 1934 largely devoid of amplified DNA. In this manner, the sample delivered to the sequencing system can include substantially only those beads having amplified DNA with a desired length of DNA strands for sequencing. Similarly stated, the sample delivered to the sequencing system can include a percentage of clonal beads approaching 100%. The separation of clonal beads may be non-magnetic beads or any other type of the beads, with or without the surface being coated with charged molecules.

When generating clonal beads a large percentage of the beads may have no DNA template. In addition others may have poor amplification. These beads do not provide useful sequencing so it may be desirable to remove these beads for better efficiency. In some embodiments of the current invention an enrichment module may be used which separates the beads with no or minimal amounts of template using an electric field.

Beads fully loaded with templates have a higher charge, and so may move farther in an electric field than beads with only primers or few templates. In one embodiment as shown in FIG. 18A-B this separation may be done in a flow through module 1800. A first fluidic input 1811A allows the injection of mixed beads. A second inlet 1812A allows the injection of a buffer solution without beads. A first outlet 1811B may be downstream from the first inlet 1811A. A second outlet 1812B may be downstream from the second inlet 1812A. Fluids may be brought into or out of the module through ports 1809. The fluidic system may have a substrate 1802, and a channel 1810 formed in a layer of PDMS 1808 glass or other material.

The fluidic flow rates can be set by fluidic resistance or pumping speed such that more liquid flows in the second inlet. In one embodiment the inlet and outlet widths may be varied to create different fluidic resistances but other methods of modifying the fluidic resistance such as different length, height are anticipated. Similarly the fluidic resistance of the first outlet 1811B and second outlet can be modified so more liquid flows out the first outlet 1811B. In such a setup beads without a small velocity perpendicular to the flow may exit the first outlet port 1811B. Additional output channels can be added to facilitate separation of beads with medium levels of template.

A pair of electrodes 1813 may be provided which enable generation of an electric field perpendicular to the fluid flow such that the template loaded beads migrate out of the flow path towards second outlet 1812B. Fluidic ports 1809 allow connection to the system plumbing.

The electrodes could be made of any electrode material compatible with electrophoresis. In some embodiments discrete metal wires may be used but metal traces are also anticipated. Metals such as platinum, platinum/iridium, gold and other noble metals or alloys are anticipated as well as corrosion resistant materials such as stainless steel. Non metal electrodes such as carbon are also anticipated.

The flow through enrichment module chamber can be constructed of non conducting materials such as molded plastic, glass, ceramic or moldable polymers such as PDMS. Fluidic components can be fused or bonded to create a flow chamber.

The voltage applied to the electrodes can be reduced or even reversed periodically if necessary should beads stick to the electrodes. The voltages used should be greater than that required for electrolysis (1.23V at 25 C at pH 7). Higher voltages and narrower gaps provide a higher field strength and more force on the beads. The voltage on the system can be calibrated by flowing beads without or with limited template and adjusting the voltage or flow rate such that these beads may not be moved far enough to enter the second outlet while beads with template may be directed into the second outlet.

Non flow-through enrichment modules are also anticipated but these may not be as easily automated as flow through systems. In one embodiment beads may be introduced to a chamber and a magnetic field or gravity pull the beads down. An electric field may be established pulling the beads with template up. In some embodiments a capture membrane or filter can be added in front of the positive electrode to facilitate concentration of the beads.

In some embodiments, beads or particles which do not have amplified DNA (clonal beads), and or beads or particles which have insufficiently amplified DNA, or beads and or beads or particles which have amplified DNA fragments which are too short, may be recycled and reused for a subsequent amplification reaction in order to generate well amplified clonal beads or particles. Beads or particles may also be recycled after said beads or particles have been utilized for sequencing. Said beads or particles may be recycled automatically within a single system.

In some embodiments, beads or particles which do not have amplified DNA may be directly reused or recycled without further processing of the beads or particles to prevent contamination from sample to sample. This may be advantageous, for example, when a single sample is utilized for several amplification reactions, rendering any cross contamination irrelevant, as the sample is in fact the same. In other embodiments, the amount of cross contamination which may result may be considered inconsequential, as the amount of cross contamination is sufficiently low.

In other embodiments, the beads may be treated to prevent cross contamination. Said treatment may, for example, comprise removal and replacement of all primers from said beads or particles wherein said primers may be associated or bound to the beads or particles using, for example, streptavidin binding, thiol binding, or the like, wherein the binding may be broken and another moiety bound. The primer which is bound to the beads or particles may be the same primer as was previously utilized, or may be a different primer, having for example, a different barcode included as part of the primer.

In other embodiments, cross contamination may be prevented by utilizing primers with an unusual nick site, wherein the primer may be nicked, washed, a splint oligo provided. and the primer restored by ligation of an oligo wherein the original sequence, or another desired sequence for the oligo is regenerated or generated.

Integrated System

FIG. 19 is a schematic illustration of the integrated sequencing platform. The integrated sequencing platform may include a DNA extraction system, a library construction system, an amplification system an enrichment system, and a sequencing system (which may include the electrical detection system or "sensing unit" described herein). Although shown schematically as separate systems, the integrated sequencing platform can include all of these systems within a single microfluidic/microelectronic device (or "chip"). Each of the systems is described in more detail below.

The DNA extraction system includes an inlet chamber 1910 for receiving the biological sample (e.g. blood) to be analyzed. The inlet chamber can include a solution to promote lysing of the cells contained within the biological sample. Such solutions are well known in the art and are typically called lysis buffers. In some embodiments, the lysis solution can be injected into the inlet chamber and mixed with the biological sample. The DNA may be extracted from the biological sample via an on-chip extraction element 1920. The extraction element 1920 can be disposed within a flow channel of the microfluidic device, and includes a filter media constructed from a porous member. The extraction element 1920 may also include one or more electrodes configured to produce an electrical field across the filter media. Thus, the combination of the filter media and the electrical field causes separation of the highly charged DNA (identified by reference character DNA) from the other portions of the biological sample. Moreover, the extraction element 1920 can be configured to separate DNA 1912 from other nucleic acids (i.e., RNA).

In some embodiments, the electrodes can be controlled to tailor the characteristics of the electric field, thus optimizing the separation characteristics of the extraction element. For example, the electrodes can be controlled to adjust the strength, polarity, spatial variability and/or transient characteristics of the electric field. In some embodiments, the extraction element 1920 can include two electrodes: the first being disposed under the porous filter media, and the second being disposed above and diagonally from the first.

As shown in FIG. 19, the library construction system may include a DNA fragmentation and/or size selection element 1916. The fragmentation and/or size selection element 1916 can be configured to produce double-stranded DNA fragments having blunted ends via the elements and methods described below. The fragmentation element 1920 includes one or more microfluidic channels 1922 within which the separated DNA may be disposed along with a set of fragmentation beads 1924. More particularly, the separated DNA produced by the DNA extraction system can be conveyed or "injected" into the DNA fragmentation and/or size selection element 1916 by any suitable mechanism (e.g., pressurized injection, electrophoretic movement, gravity feed, heat-induced movement, ultrasonic movement and/or the like). Similarly, the fragmentation beads 1924 can be conveyed into the DNA fragmentation and/or size selection element 1916 by any suitable mechanism.

The fragmentation and/or size selection element 1916 may include a pump 1926 to produce movement of the solution of DNA and fragmentation beads 1924 within the microfluidic channel 1922. The pump 1926 can be, for example, a peristaltic pump. In some embodiments, the pump 1926 can include one or more microfluidic elements in fluid communication with the microfluidic channel 1922, and having a flexible side-wall that, when deformed, produces a flow within the microfluidic channel 1922. In other embodiments, however, any suitable mechanism can be used to produce movement of the solution of DNA and fragmentation beads 1924 within the microfluidic channel 1922 (e.g., via selective heating and cooling of the solution, pneumatic pressurization of the microfluidic channel, electrophoretic motion, or the like.)

Figure 24:
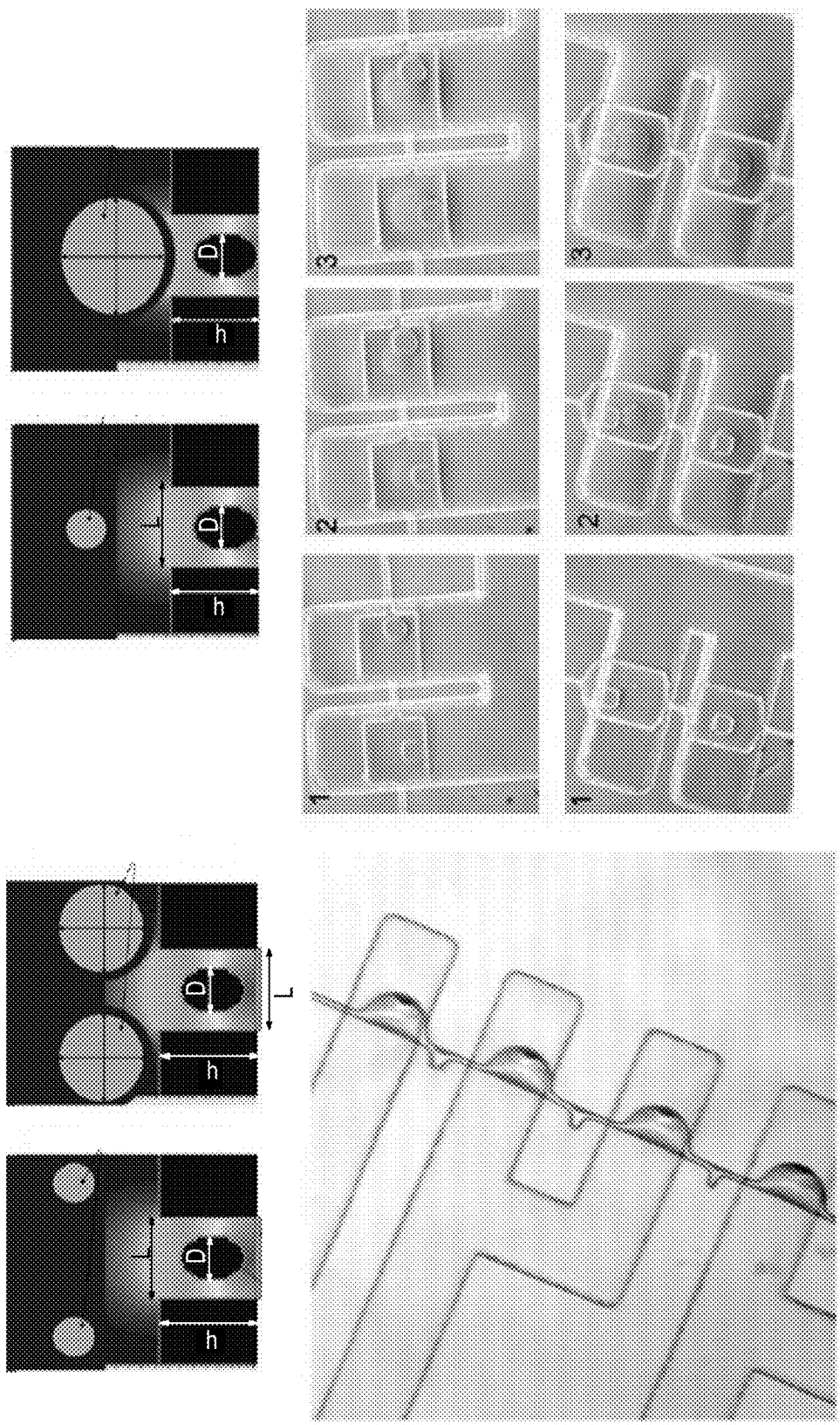

The fragmentation beads 1924 can be constructed from any material suitable for separating, cutting and/or otherwise dividing the DNA into DNA fragments (identified by reference character DNA-SEG). In some embodiments, the fragmentation beads 1924 can be constructed from glass, polydimethylsiloxane (PDMS), ceramic or the like. Moreover, the fragmentation beads 1924 can have any suitable size and/or geometry such that the fragmentation element 1920 produces DNA fragments having the desired characteristics (e.g., length, strand characteristics or the like). Moreover, the size and/or geometry of the microfluidic channel 1922 (e.g., cross-sectional shape, aspect ratio or the like) can be selected such that the movement of the DNA within the microfluidic channel 1922 and in contact with the fragmentation beads 1924 produces the desired shearing of the DNA. For example, in some embodiments, the fragmentation beads 1924 can be substantially spherical and can have a diameter of 50 nm or less. In other embodiments, the fragmentation beads 1924 can have a diameter of 500 nm or less, or any diameter between 50 µm and 500 nm. In some embodiments, the microfluidic channel 1922 may be in the range of 1 to 500 µm in hydraulic diameter (i.e., as shown in FIG. 24, the cross-sectional area of the microfluidic channel 1922 can be substantially rectangular, thus the size can be represented as a hydraulic diameter). In other embodiments, the hydraulic diameter of the microfluidic channel 1922 can be in the range of 10 to 200 µm. In yet other embodiments, the hydraulic diameter of the microfluidic channel 1922 can be in the range of 500 nm or less. Moreover, although shown in FIG. 24 as being substantially rectangular, in other embodiments the microfluidic channel can have any suitable shape, such as semi-circular, oval, tapered or the like. In some embodiments enzymatic polishing of the sheared DNA ends can be done to insure the ends are blunt ends.

In other embodiments, an enzymatic solution can be conveyed into the microfluidic channel 1922 to, at least partially, produce enzymatic fragmentation of the DNA.

Upon completion of the fragmentation, the DNA fragments may be separated from the fragmentation beads 1924. The DNA fragments can be separated from the fragmentation beads 1924 by any suitable mechanism, such as, for example, by a filter, by gravitational (or centripetal) separation, by an electrical field, or the like. In some embodiments, for example, the DNA fragments can be separated from the fragmentation. beads 1924 by the actuation of one or more control lines or control channels, as described below with reference to FIG. 20. In particular, the control channels may be channels that are fluidically isolated from, but adjacent and usually perpendicular to the microfluidic channel 1922. The control channels can, for example, be defined by a side wall that also defines a portion of the microfluidic channel. In this manner, when the pressure of a fluid within the control channel may be increased, the common side wall can deform, thereby changing the flow area of a portion of the microfluidic channel 1922. To separate the DNA fragments from the fragmentation beads 1924, a pressure can be selectively applied to the control channel such that the flow area of the microfluidic channel may be small enough to retain the fragmentation beads, but large enough to allow the DNA fragments to pass therethrough. Said another way, in some embodiments, the valves in the channel can be partially closed creating a leaky "sieve valve" to separate the DNA fragments from the fragmentation beads 1924.

In some embodiments, the fragmentation and/or size selection element may comprise an electrophoretic device which may further comprise a set of electrodes embedded in a microfluidic channel and may further include a means for introducing an entangled polymer, buffers and wash solutions.

As further shown in FIG. 19, the DNA fragments may then be conveyed into the amplification and enrichment systems. The amplification and enrichment systems can be configured to produce clonally amplified DNA from the fragmented DNA that can be sequenced as described below. The PCR and enrichment system may include an array of microfluidic channels 1932 within which the DNA fragments may be associated with a series of magnetic beads 1934. The DNA fragments and magnetic or paramagnetic beads 1934 may be positioned within the microfluidic channels via a corresponding magnetic array. In this manner, the DNA fragments and magnetic or paramagnetic beads 1934 can be maintained in the desired position to promote accurate and efficient sample amplification. For example, the DNA fragments and magnetic or paramagnetic beads 1934 can be maintained in the desired position within the "flow-through" microfluidic channels 1932, and the desired reagents can be conveyed within the microfluidic channels 1932 and into contact with the DNA fragments to promote amplification of the DNA fragments.

After amplification of the target DNA onto beads, the beads may be sorted in an electrophoretic sorter 1938 as previously described, and beads with appropriate amounts of amplified product 1940 may be moved into a sequencing module 1936.

As described above, the integrated sequencing platform can include all of the systems described herein within a single microfluidic/microelectronic device (or "chip") or may be modular devices in one system. FIGS. 20-24 show embodiments of the microfluidic portions of the integrated platform for extracting, amplifying and sequencing polynucleotides.

Figure 20:
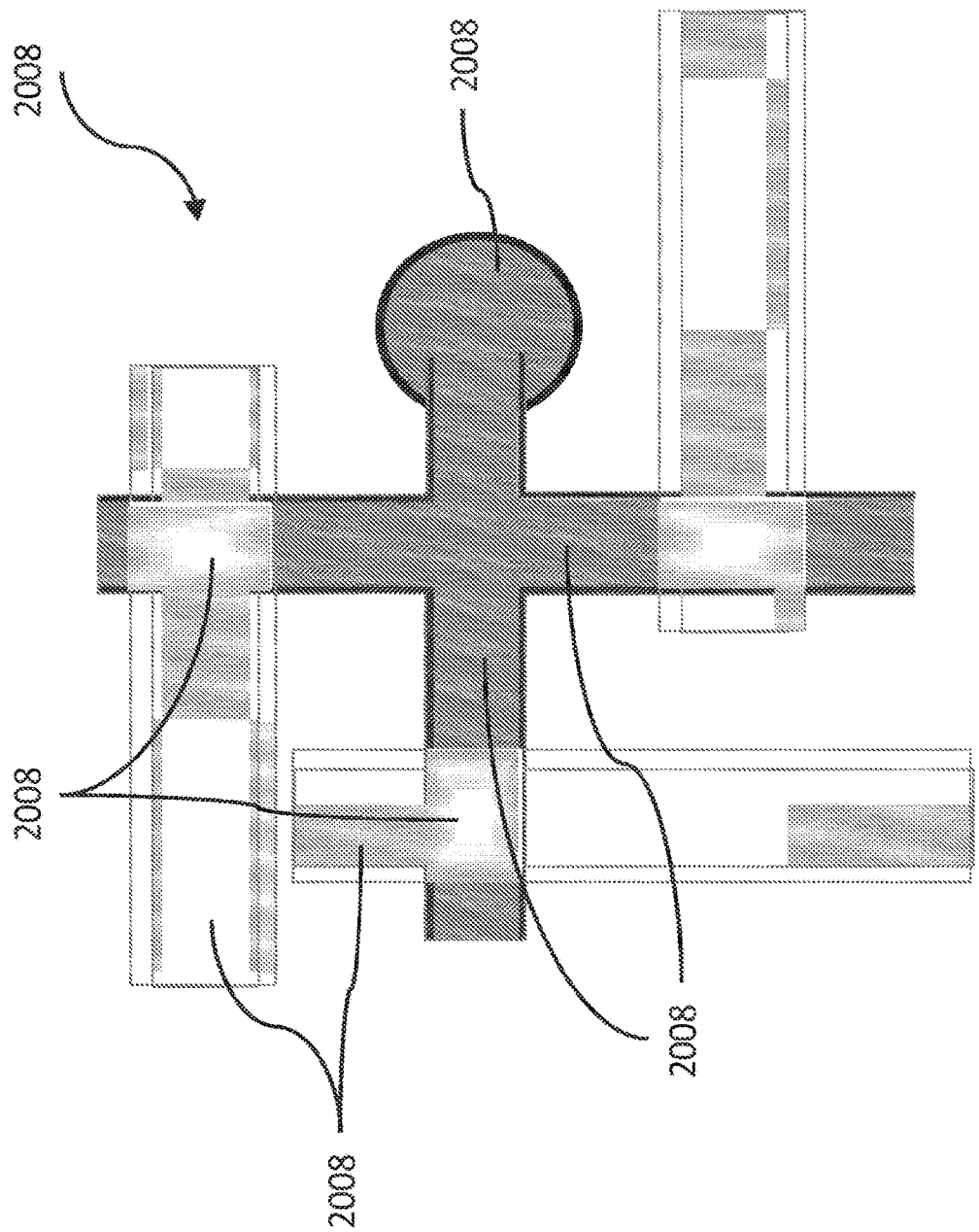
FIGS. 20-24 show embodiments of the microfluidic portions of the integrated platform for extracting, amplifying and sequencing polynucleotides.
Figure 21:
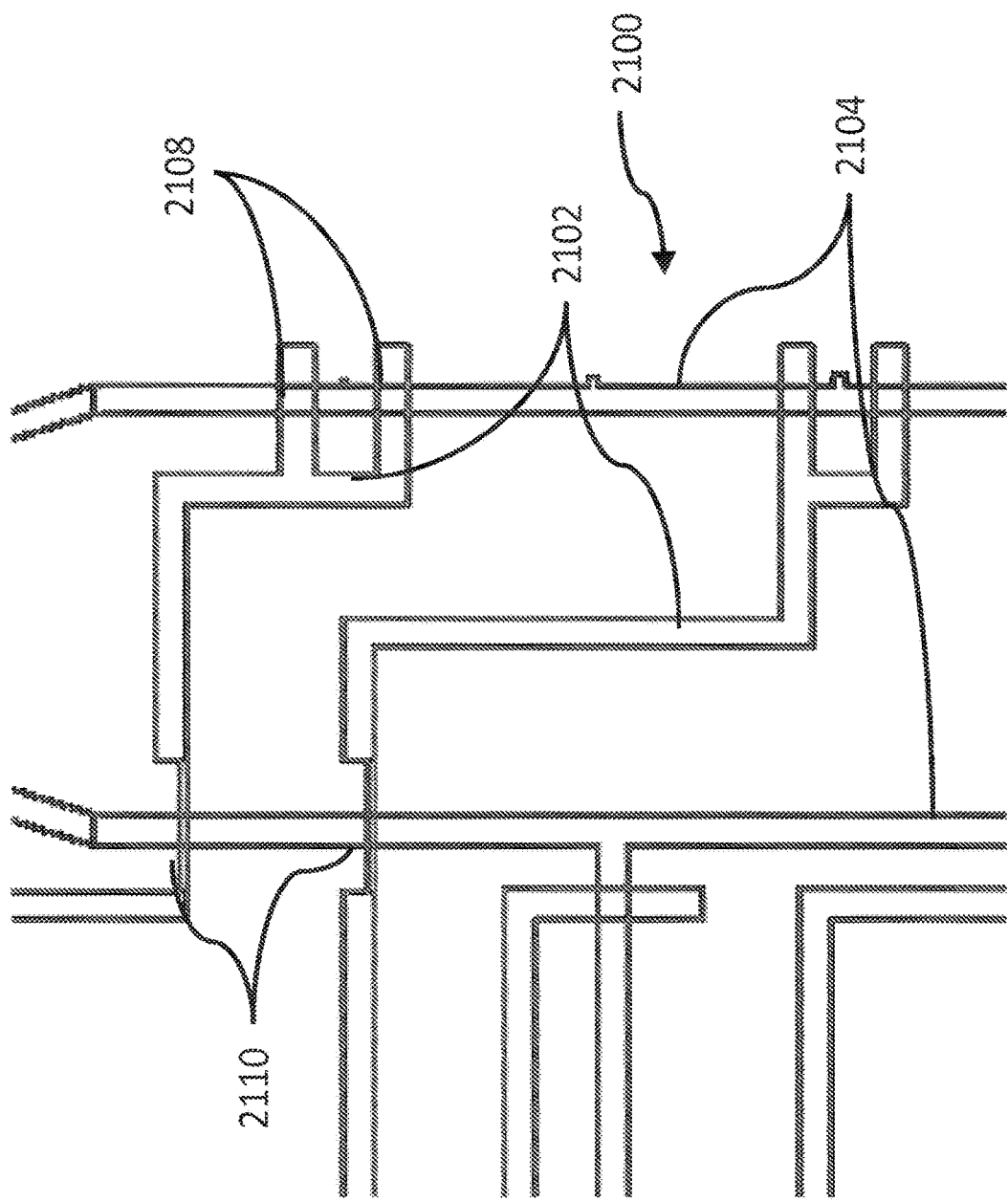
Figure 22:
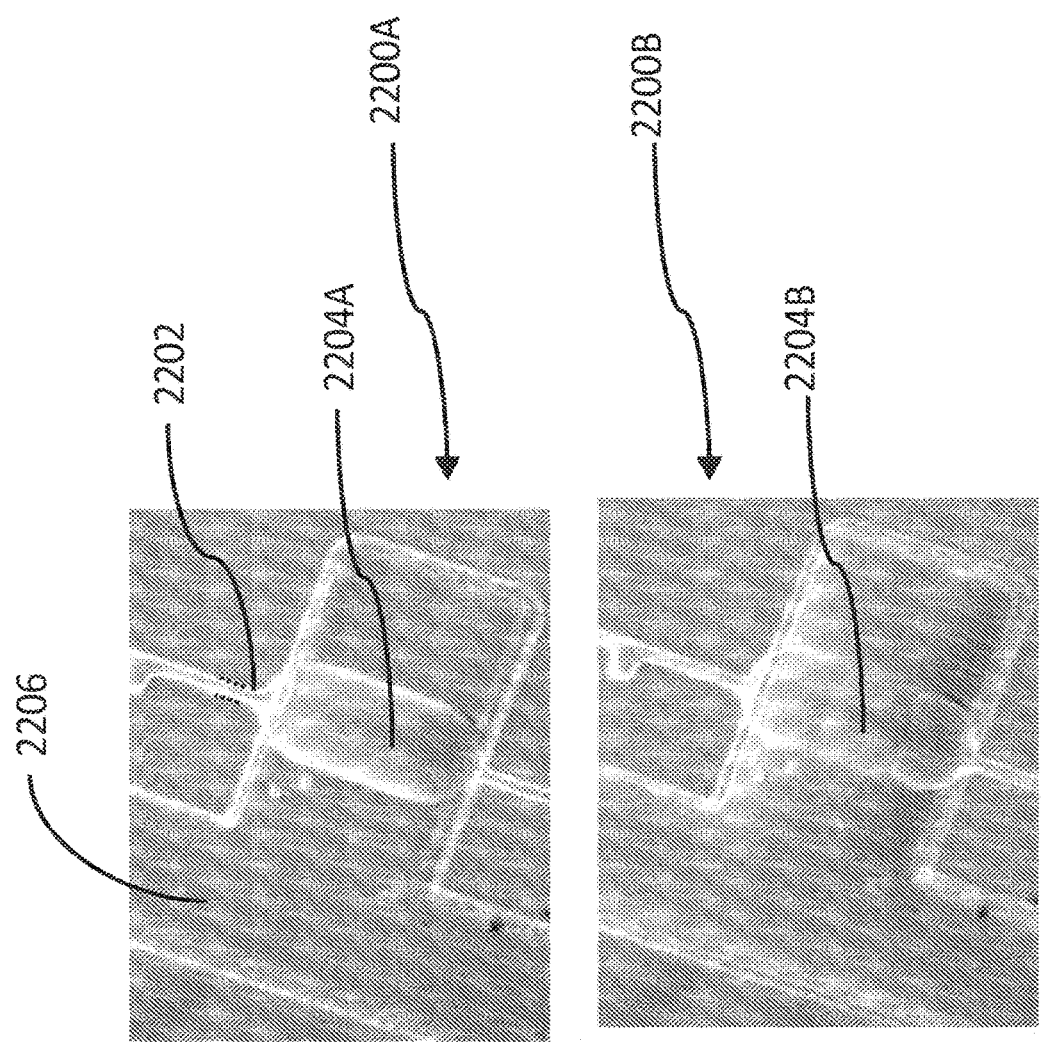
Figure 23:
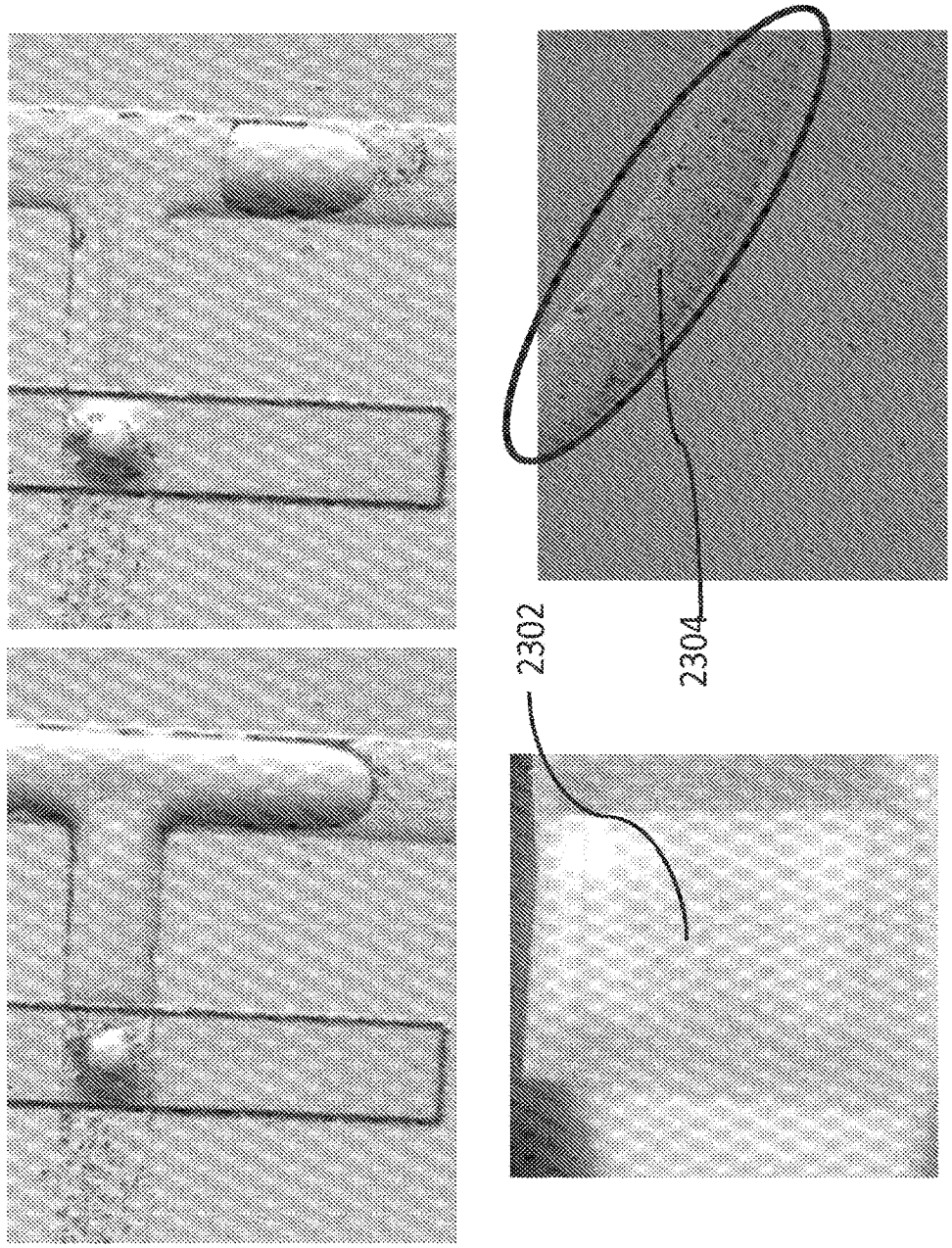

As in FIG. 20, a microfluidic device 2000 may have one or more input or output ports 2006. Fluids may be introduced through said ports 2006 to fluidic channels 2004. Control lines 2002 may control the flow of fluids through the activation of valves 2008. Pressurizing the control lines 2002, deforms a wall between the control lines 2002 and the fluidic channels 2004, pinching off the fluidic channel and closing the valve 2008. FIG. 21 shows a further embodiment of the fluidics system, with similar control lines 2102, fluidic channels 2104 and valves 2108, but with additional crossovers 2110, wherein the control line is narrowed too much to be able to fully deform to the point wherein the fluidic channel 2102 is sealed, preventing the crossover 2110 from acting as a valve 2108. FIG. 22 shows microphotographs of a portion of a device 2200A and 2200 B with enlarged fluidic channels 2204, permitting visualization of the activation of control line 2202. If the view of the device 2200A, the control line is not activated, and the valve 2208 can be seen to be open. After activation of the control line 2202, one can see that in device 2200B that the valve 2208B has deformed and sealed the fluidic channel 2204. FIG. 23 shows several views of a PDMS valving device 2302, including photomicrographs of paramagnetic beads 2304 in a channel, and view with a wherein flow is occurring, and where a valve has been activated and no flow occurs. The microfluidic device can control the "injection" or flow of the beads, reagents and/or samples described herein by a series of control fines that intersect with and/or impede upon the microfluidic channels described herein. As shown in FIG. 24 and described above, the control lines can be expanded to retain the solution and/or beads within a predetermined portion of the device.

For injecting picoliter amounts of amplification or sequencing reagents into the fluidic system, e.g., for incorporation of dNTPs onto bead-immobilized DNA primers, the magnetic array may utilize a micro-fluidics system. For example, the microfluidic platform may contain lines for injecting/delivering reactants to the localized magnetic fields. For sequencing embodiments, the microfluidic system controls sequential injections of nucleotide triphosphates to the substrate or to localized magnetic fields. The microfluidic channels may be in the range of 1 to 100 µm in diameter, or in certain embodiments, in the range of 10 to 20 µm in diameter. Materials and methods for fabricating the micro-fluidics system are known. For example, the microfluidics system may be fabricated with polydimethyl siloxane (PDMS), molded or machined plastic or glass.

The invention therefore provides in certain aspects, a magnetic array, as described herein, having a magnetic bead or particle trapped by magnetic force at a plurality of the localized magnetic features, each magnetic bead or particle having bound thereto a clonally amplified DNA segment for sequence analysis. The DNA segment may be clonally amplified, for example, using the magnetic array, optionally having an electric field, as described herein.

The amplification and sequencing arrays may be placed in sequential order in an integrated platform. For example, after amplification on a magnetic array, the beads may be enriched based on a DNA electrophoretic force. Specifically, the beads with amplified DNA, and with the adequate length, may have the minimum required charge to be pulled off to an exit integrated with a DNA sequencer. The null beads, as well as beads with incomplete amplification or overly short DNA amplicons, may be separated through another outlet.

It may be desirable to process multiple samples in a single chip, since many projects do not require the full capacity of a chip. Other projects may have a single sample that would exceed the capacity of the chip. In some embodiments one or more samples could be introduced into the instrument in individual tubes, tube strips, 96-well plates, 384-well plates, etc. In some embodiments the sample wells could be sealed to prolong life on the instrument. In other embodiments the plates may be cooled to increase sample life. In other embodiments the samples could be accessed in a software selectable manner by a robotic pipettor. The system could divide the samples over multiple fluidic channels or chips if they are too large, or combine the samples if they are combinable (for example using sequence barcoded samples). In some embodiments sample may be loaded at different times in the same sequencing device in different channels, enabling samples to be run when they become available. In some embodiments samples provided to the instrument would be ready for sequencing. In other embodiments samples could be processed by the instrument to generate sequencing ready samples.

In one embodiment a target concentration may be created by a hybridization based pullout. A solid support such as pull-out beads could be functionalized with a controlled number of binding sites. In some embodiments these could be DNA primer compliments. The unamplified sample may have known primers ligated on each end. In some embodiments the primers would hybridize to the DNA on the pull-out beads. After the sites are exhausted, residual DNA would be washed away, and the DNA bound to the beads would subsequently be denatured releasing a known quantity of DNA.

In another embodiment the primers ligated to each DNA fragment could be beyond to the primer compliment and detected using fluorescence detection of an intercalating dye. Since the primers may be of a known length, the signal level may be proportional to the number of fragments. In another embodiment polymerase and associated dNTPs could be introduced creating full length double stranded DNA. When combined with the information from the primer signal the full length intercalating dye signal level would then allow determination of the mean fragment length.

Although various embodiments have been described, as having particular features and/or combinations of components, other embodiments are possible having a combination of any features and/or components from any of embodiments as discussed above.

While various embodiments have been described above, it should be understood that they have been presented by way of example only, and not limitation. Where methods and/or schematics described above indicate certain events and/or flow patterns occurring in certain order, the ordering of certain events and/or flow patterns may be modified. While the embodiments have been particularly shown and described, it will be understood that various changes in form and details may be made. While the embodiments have been particularly shown and described for nucleic acid detection or DNA sequencing, it will be understood that the system may be configured or used for various other biochemical reactions and detection thereof.

What is claimed is:

1. A system for identifying at least a portion of a biological material, comprising:
    a container configured to retain a solution containing or suspected of containing said biological material;
    a sensor adjacent to said container, wherein said sensor comprises at least two electrodes configured to (i) couple to a double layer associated with said biological material and (ii) detect one or more signals indicative of a change of charge or conductivity within said double layer, wherein during use, said at least two electrodes are exposed to said solution containing or suspected of containing said biological material; and
    a detection module operatively coupled to said sensor, wherein said detection module is configured to use said one or more signals detected by said sensor to identify said at least said portion of said biological material.

2. The system of claim 1, wherein said sensor comprises more than two electrodes.

3. The system of claim 1, wherein said at least two electrodes are separated by a dielectric.

4. The system of claim 1, wherein said sensor is configured to detect said one or more signals within said double layer associated with said biological material when said biological material is coupled to a support adjacent to said sensor.

5. The system of claim 4, wherein said at least two electrodes are electrically isolated in the absence of said support.

6. The system of claim 4, wherein said support is a particle, and wherein during use, said biological material is coupled to said particle.

7. The system of claim 6, wherein, during use, said particle is positioned adjacent to said sensor such that said double layer is in electrical communication with said particle and said sensor.

8. The system of claim 6, wherein said container is a well that aids in limiting motion of said particle while detecting said at least said portion of said biological material.

9. The system of claim 6, further comprising a magnet that, during use, provides a magnetic force that immobilizes said particle adjacent to said sensor.

10. The system of claim 1, further comprising a confinement unit that is configured to attract said biological material or one or more reagents to said container, which one or more reagents are for conducting one or more reactions on said biological material.

11. The system of claim 10, wherein said confinement unit is configured to selectively attract charged species in said solution to reduce contamination of said biological material or said one or more reagents in said container.

12. The system of claim 10, wherein said confinement unit comprises a plurality of electrodes that is configured to direct said biological material or said one or more reagents to said container.

13. The system of claim 1, further comprising read-out circuitry that receives said one or more signals from said sensor.

14. The system of claim 1, wherein said biological material is a nucleic acid molecule.

15. The system of claim 14, wherein said detection module is configured to identify at least a portion of a sequence of said nucleic acid molecule.

16. The system of claim 1, wherein said biological material is a protein.

17. The system of claim 1, further comprising a plurality of sensors, which plurality of sensors comprises said sensor.

18. The system of claim 17, wherein said container encloses said plurality of sensors.

19. The system of claim 1, wherein said biological material is coupled to a surface of said sensor.

20. The system of claim 19, wherein said surface of said sensor is substantially planar.

21. The system of claim 1, wherein said one or more signals are indicative of said change of conductivity.

* * * * *

UNITED STATES PATENT AND TRADEMARK OFFICE
CERTIFICATE OF CORRECTION

PATENT NO. : 10,472,674 B2
APPLICATION NO. : 15/360369
DATED : November 12, 2019
INVENTOR(S) : Hesaam Esfandyarpour et al.

Page 1 of 1

It is certified that error appears in the above-identified patent and that said Letters Patent is hereby corrected as shown below:

In the Specification

At Column 1, Line 26, please delete:
"STATEMENT REGARDING FEDERALLY SPONSORED RESEARCH AND DEVELOPMENT
This invention was made with government support under a Qualifying Therapeutic Discovery Grant awarded be the IRS, in conjunction with the Department of Health and Human Services. The U.S. Government has certain rights in the invention."

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*